(12) United States Patent
Ledesma et al.

(10) Patent No.: US 12,023,332 B2
(45) Date of Patent: Jul. 2, 2024

(54) COMPOSITIONS AND METHODS FOR ACTIVATING SIGNALING THROUGH THE CB1 CANNABINOID RECEPTOR FOR TREATING AND PREVENTING DISEASES AND DISORDERS CHARACTERIZED BY ABNORMAL CELLULAR ACCUMULATION OF SPHINGOLIPIDS SUCH AS SPHINGOMYELIN

(71) Applicant: Wylder Nation Foundation, Scottsdale, AZ (US)

(72) Inventors: Maria Dolores Ledesma, Scottsdale, AZ (US); Adrian Bartoll, Scottsdale, AZ (US); Edward H. Schuchman, Scottsdale, AZ (US)

(73) Assignee: Wylder Nation Foundation, Scottsdale, AZ (US)

( * ) Notice: Subject to any disclaimer, the term of this patent is extended or adjusted under 35 U.S.C. 154(b) by 958 days.

(21) Appl. No.: 16/977,772

(22) PCT Filed: Mar. 5, 2019

(86) PCT No.: PCT/US2019/020828
§ 371 (c)(1),
(2) Date: Sep. 2, 2020

(87) PCT Pub. No.: WO2019/173394
PCT Pub. Date: Sep. 12, 2019

(65) Prior Publication Data
US 2021/0085678 A1    Mar. 25, 2021

Related U.S. Application Data

(60) Provisional application No. 62/638,837, filed on Mar. 5, 2018.

(51) Int. Cl.
| | |
|---|---|
| A61K 31/501 | (2006.01) |
| A61K 9/00 | (2006.01) |
| A61K 31/16 | (2006.01) |
| A61K 31/164 | (2006.01) |
| A61K 31/232 | (2006.01) |
| A61K 31/325 | (2006.01) |
| A61K 31/415 | (2006.01) |
| A61K 31/4164 | (2006.01) |
| A61K 31/4545 | (2006.01) |
| A61K 31/496 | (2006.01) |
| A61K 31/573 | (2006.01) |
| A61K 35/28 | (2015.01) |
| A61K 45/06 | (2006.01) |
| A61P 1/00 | (2006.01) |
| A61P 25/28 | (2006.01) |
| C12N 9/16 | (2006.01) |

(52) U.S. Cl.
CPC .......... *A61K 31/501* (2013.01); *A61K 9/0085* (2013.01); *A61K 31/16* (2013.01); *A61K 31/164* (2013.01); *A61K 31/232* (2013.01); *A61K 31/325* (2013.01); *A61K 31/415* (2013.01); *A61K 31/4164* (2013.01); *A61K 31/4545* (2013.01); *A61K 31/496* (2013.01); *A61K 31/573* (2013.01); *A61K 35/28* (2013.01); *A61K 45/06* (2013.01); *A61P 1/00* (2018.01); *A61P 25/28* (2018.01); *C12N 9/16* (2013.01); *C12Y 301/04012* (2013.01)

(58) Field of Classification Search
CPC .................................................. A61K 31/501
See application file for complete search history.

(56) References Cited

U.S. PATENT DOCUMENTS

| | | | |
|---|---|---|---|
| 5,262,564 A | 11/1993 | Kun et al. | |
| 8,541,581 B2* | 9/2013 | Castro | ..................... A61P 37/00 546/13 |
| 9,271,962 B2* | 3/2016 | Makriyannis | ............. A61P 3/00 |
| 2009/0099131 A1 | 4/2009 | Adams et al. | |
| 2010/0267733 A1 | 10/2010 | Shytle et al. | |

(Continued)

FOREIGN PATENT DOCUMENTS

| | | |
|---|---|---|
| WO | WO 2007/130361 A1 | 11/2007 |
| WO | WO 2008/001369 A1 | 1/2008 |
| WO | WO 2008/150492 A1 | 12/2008 |

(Continued)

OTHER PUBLICATIONS

Ahn, et al., "Mechanistic and Pharmacological Characterization of PF-04457845: A Highly Potent and Selective Fatty Acid Amide Hydrolase Inhibitor that Reduces Inflammatory and Noninflammatory Pain," The Journal of Pharmacology and Experimental Therapeutics, 2011, 338(1), 114-124.

(Continued)

*Primary Examiner* — Golam M Shameem
(74) *Attorney, Agent, or Firm* — COOLEY LLP

(57) ABSTRACT

The present invention provides, inter alia, compositions and methods for using CB1 cannabinoid receptor agonists, or other compounds capable of increasing endocannabinoids or endocannabinoid signaling, for treating and preventing lysosomal storage disorders in which lipid storage occurs (including, e.g., disorders associated with sphingomyelin accumulation). In particular embodiments, the present invention provides compositions and methods for treating such lysosomal storage disorders with one or more fatty acid amide hydrolase inhibitor alone or in combination with one or more additional agent.

12 Claims, 39 Drawing Sheets

(56) References Cited

U.S. PATENT DOCUMENTS

2023/0181540 A1    6/2023    Schuchman et al.

FOREIGN PATENT DOCUMENTS

| WO | WO 2010/005572 A2 | 1/2010 |
|---|---|---|
| WO | WO 2011/085216 A2 | 7/2011 |
| WO | WO 2019/173394 A1 | 9/2019 |

OTHER PUBLICATIONS

Alayoubi, et al., "Systemic ceramide accumulation leads to severe and varied pathological consequences," EMBO Mol. Med., 2013, 5, 827-842.
Arfi, et al., "Neuroinflammatory and oxidative stress phenomena in MPS IIIA mouse model: The positive effect of long-term aspirin treatment," Molecular Genetics and Metabolism, 2011, 103, 18-25.
Arroyo, et al., "Pharmacological reversion of sphingomyelin-induced dendritic spine anomalies in a Niemann Pick disease type A mouse model," EMBO Mol Med., 2014, 6, 398-413.
Ashton, et al., "The Cannabinoid CB2 Receptor as a Target for Inflammation-Dependent Neurode-generation," Current Neuropharmacology, 2007, 5, 73-80.
Barbon, et al., "AAV8-Mediated Hepatic Expression of Acid Sphingomyelinase Corrects the Metabolic Defect in the Visceral Organs of a Mouse Model of Niemann-Pick Disease," Molecular Therapy, Sep. 2005, 12(3), 431-440.
Bosch, et al., "Neuroinflammatory paradigms in lysosomal storage diseases," Frontiers in Neuroscience, Oct. 30, 2015, 9, 1-11.
Burstein, et al., "Stimulation of Sphingomyelin Hydrolysis by Cannabidiol in Fibroblasts from a Niemann-Pick Patient," Biochemical and Biophysical Research Communications, 1984, 121(1), 168-173.
Cañamás, et al., "Sphingomyelin-induced inhibition of the plasma membrane calcium ATPase causes neurodegeneration in type A Niemann-Pick disease," Molecular Psychiatry, 2017, 22, 711-723.
Devlin, et al., "Improvement in Lipid and Protein Trafficking in Niemann-Pick C1 Cells by Correction of a Secondary Enzyme Defect," Traffic, 2010, 11, 601-615.
Di Marzo, "The endocannabinoid system: Its general strategy of action, tools for its pharmacological manipulation and potential therapeutic exploitation," Pharmacological Research, 2009, 60, 77-84.
Dodge, et al., "Gene transfer of human acid sphingomyelinase corrects neuropathology and motor deficits in a mouse model of Niemann-Pick type A disease," PNAS, Dec. 6, 2005, 102(49), 17822-17827.
Dodge, et al., "Intracerebroventricular infusion of acid sphingomyelinase corrects CNS manifestations in a mouse model of Niemann-Pick A disease," Experimental Neurology, 2009, 215, 349-357.
Galvan, et al., "Anomalous Surface Distribution of Glycosyl Phosphatidyl Inositol-anchored Proteins in Neurons Lacking Acid Sphingomyelinase," Molecular Biology of the Cell, Feb. 2008, 19, 509-522.
Horinouchi, et al., "Acid sphingomyelinase deficient mice: a model of types A and B Niemann-Pick disease," Nature Genetics, Jul. 1995, 10, 288-293.
International Preliminary Report on Patentability dated Sep. 8, 2020, for International Application No. PCT/US2019/020828, 9 pages.
International Search Report and Written Opinion issued in PCT/US2019/020828 dated May 29, 2019, 1-12.
International Search Report and Written Opinion issued in PCT/US2021/033333 dated Sep. 3, 2021, 1-14.
Johnson, et al., "Discovery of PF-04457845: A Highly Potent, Orally Bioavailable, and Selective Urea FAAH Inhibitor," ACS Med. Chem. Lett. 2011, 2, 91-96.
Li, et al., "Assessment of the pharmacology and tolerability of PF-04457845, an irreversible inhibitor of fatty acid amide hydrolase-1, in healthy subjects," British Journal of Clinical Pharmacology, 2011, 73(5), 706-716.
Maccarrone, et al., "Anandamide inhibits metabolism and physiological actions of 2-arachidonoylglycerol in the striatum," Nature Neuroscience, Feb. 2008, 11(2), 152-159.
Miranda, et al., "Hematopoietic stem cell gene therapy leads to marked visceral organ improvements and a delayed onset of neurological abnormalities in the acid sphingomyelinase deficient mouse model of Niemann-Pick disease," Gene Therapy, 2000, 7, 1768-1776.
Miranda, et al., "Infusion of recombinant human acids sphingomyelinase into Niemann-Pick diseases mice leads to visceral, but not neurological, correction of the pathophysiology," The FASEB Journal, Oct. 2000, 14, 1988-1995.
Nair AB, et al. "A simple practice guide for dose conversion between animals and human," Journal of Basic and Clinical Pharmacy, Mar.-May 2016, 7(2), 27-31.
Neufeld, et al., "The Mucopolysaccharidoses," The Online Metabolic and Molecular Bases of Inherited Diseases, 2019, downloaded Mar. 22, 2022, 1-73.
Panlilio, et al., "Inhibition of FAAH and activation of PPAR: New approaches to the treatment of cognitive dysfunction and drug addiction," Pharmacology and Therapeutics, 2013, 138, 84-102.
Passini, et al., "AAV Vector-Mediated Correction of Brain Pathology in a Mouse Model of Niemann-Pick A Disease," Molecular Therapy, May 2005, 11(5), 754-762.
Passini, et al., "Combination brain and systemic injections of AAV provide maximal functional and survival benefits in the Niemann-Pick mouse," PNAS, May 29, 2007, 104(22), 9505-9510.
Rodríguez, et al., "High sphingomyelin levels induce lysosomal damage and autophagy dysfunction in Niemann Pick disease type A," Cell Death and Differentiation, 2014, 21, 864-875.
Salegio, et al., "Safety Study of Adeno-Associated Virus Serotype 2-Mediated Human Acid Sphingomyelinase Expression in the Nonhuman Primate Brain," Human Gene Therapy, Aug. 2012, 23, 891-902.
Sánchez, et al., "The $CB_1$ Cannabinoid Receptor of Astrocytes is Coupled to Sphingomyelin Hydrolysis through the Adaptor Protein Fan," Molecular Pharmacology, 2001, 59, 955-959.
Schuchman, et al., "The pathogenesis and treatment of acid sphingomyelinase-deficient Niemann-Pick disease," J. Inherit Metab Dis., 2007, 30, 654-663.
Simonaro, et al., "Modulation of the endocannabinoid receptor CB2 as a novel treatment for the lysosomal diseases," 2020, 132(2), Molecular Genetics and Metabolism, 1 page.
Smith, et al., "Beneficial effects of anti-inflammatory therapy in a mouse model of Niemann-Pick disease type C1," Neurobiology of Disease, 2009, 36, 242-251.
Walkey, "Cellular Pathology of Lysosomal Storage Disorders," Brain Pathology, 1998, 8, 175-193.
Wasserstein, et al., "Successful within-patient dose escalation of olipudase alfa in acid sphingomyelinase deficiency," Molecular Genetics and Metabolism, 2015, 116, 88-97.
Ziegler, et al., "Distribution of acid sphingomyelinase in rodent and non-human primate brain after intracerebroventricular infusion," Experimental Neurology, 2011, 231, 261-271.
CAS No. 1020315-31-4, copyright 2023, 1 page.
CAS No. 112830-95-2, copyright 2023, 1 page.
CAS No. 1233855-46-3, copyright 2023, 1 page.
CAS No. 131543-22-1, copyright 2023, 1 page.
CAS No. 137945-48-3, copyright 2023, 1 page.
CAS No. 155471-08-2, copyright 2023, 1 page.
CAS No. 180002-83-9, copyright 2023, 1 page.
CAS No. 209414-07-3, copyright 2023, 1 page.
CAS No. 256934-39-1, copyright 2023, 1 page.
CAS No. 259869-55-1, copyright 2023, 1 page.
CAS No. 444912-48-5, copyright 2023, 1 page.
CAS No. 546141-08-6, copyright 2023, 1 page.
CAS No. 666260-75-9, copyright 2023, 1 page.
CAS No. 86855-26-7, copyright 2023, 1 page.
CAS No. 885490-15-3, copyright 2023, 1 page.

(56) References Cited

OTHER PUBLICATIONS

CAS No. 885496-53-7, copyright 2023, 1 page.
CAS No. 288862-83-9, CAY-10402, copyright 2023, 1 page.
Frohbergh, M. et al. "Dose Responsive Effects of Subcutaneous Pentosan Polysulfate Injection in Mucopolysaccharidosis Type VI Rats and Comparison to Oral Treatment," PLOS ONE, Jun. 2014, 9(6):e100882:1-12.
Guo, N. et al. "Pentosan Polysulfate Treatment of Mucopolysaccharidosis Type IIIA Mice," JIMD Reports, Apr. 14, 2018, 37-52.
International Preliminary Report on Patentability for International Application No. PCT/US2021/033333, dated Dec. 1, 2022, 10 pages.
Kakkis, E. et al. "Enzyme-Replacement Therapy in Mucopolysaccharidosis I," The New England Journal of Medicine, Jan. 18, 2001, 344(3):182-188.
Simonaro, C. et al. "Pentosan Polysulfate: Oral Versus Subcutaneous Injection in Mucopolysaccharidosis Type I Dogs," PLOS ONE, Apr. 11, 2016, 11(4):1-18.

\* cited by examiner

Figure 5
FIG. 5A
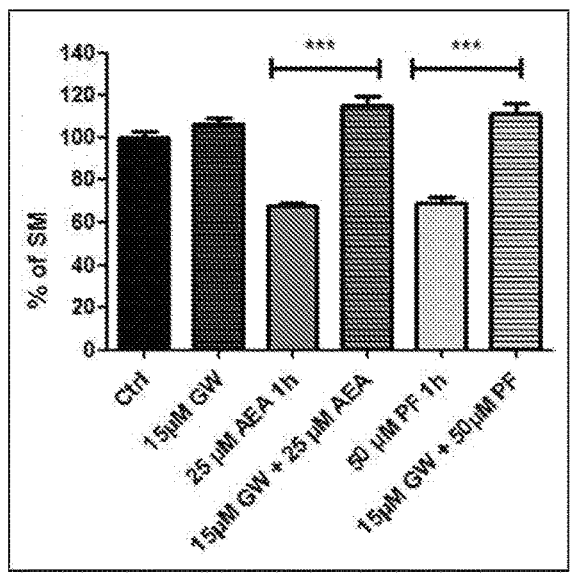
FIG. 5B
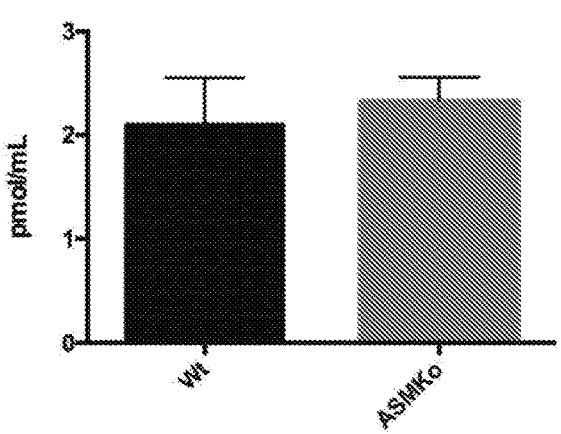
FIG. 5C
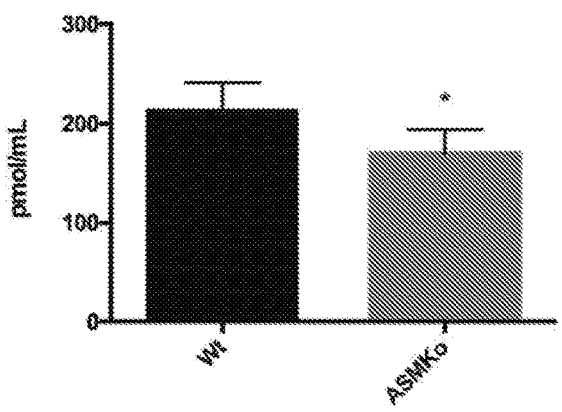
FIG. 5D
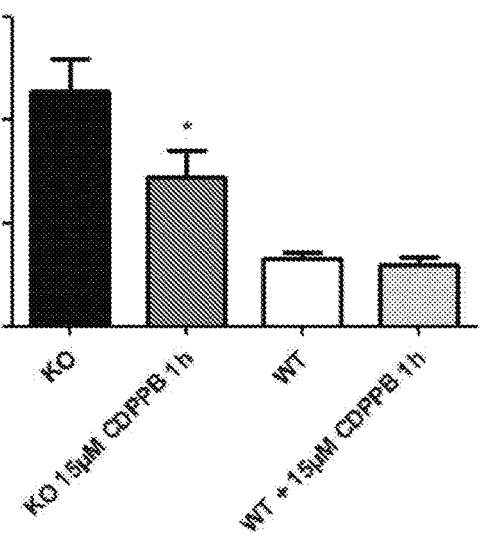

Figure 13
FIG. 13A
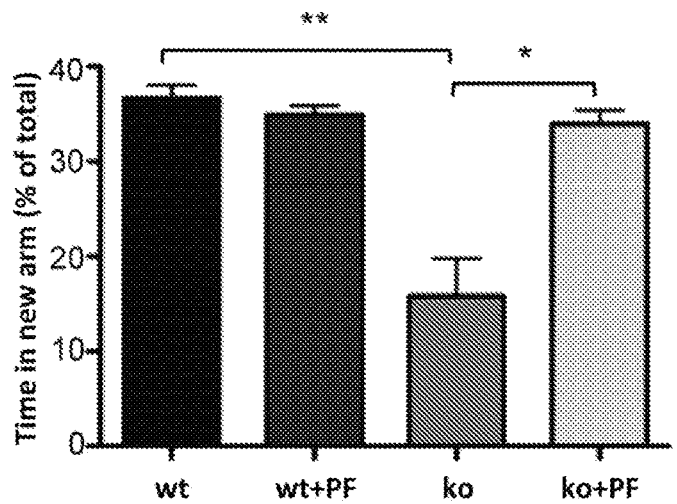
FIG. 13B
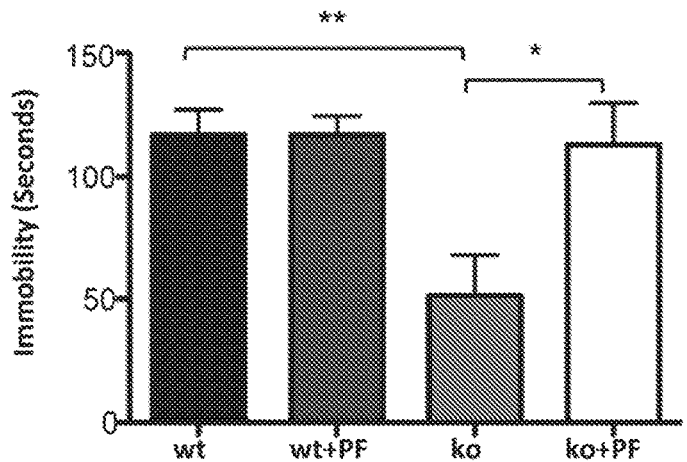
FIG. 13C
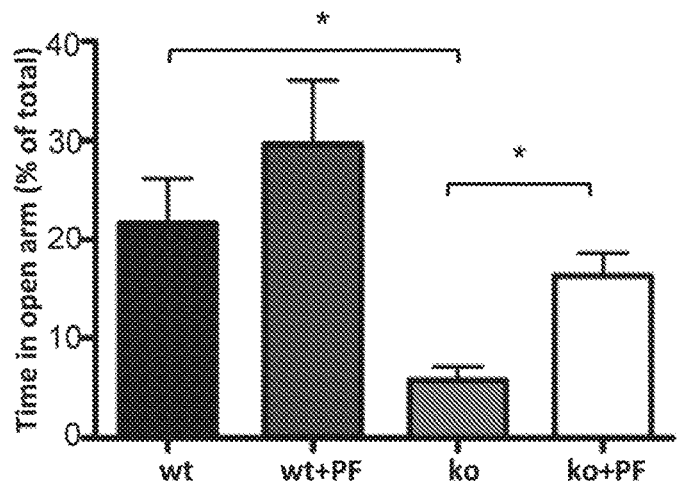

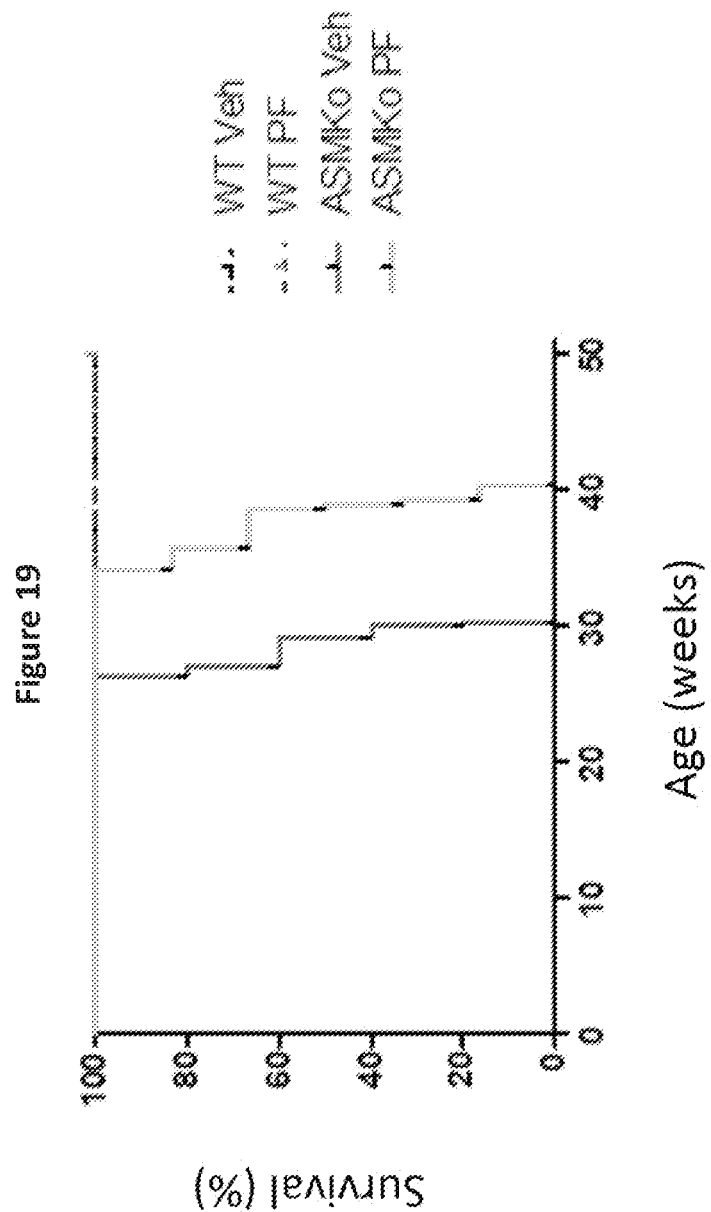

Figure 24
FIG. 24A
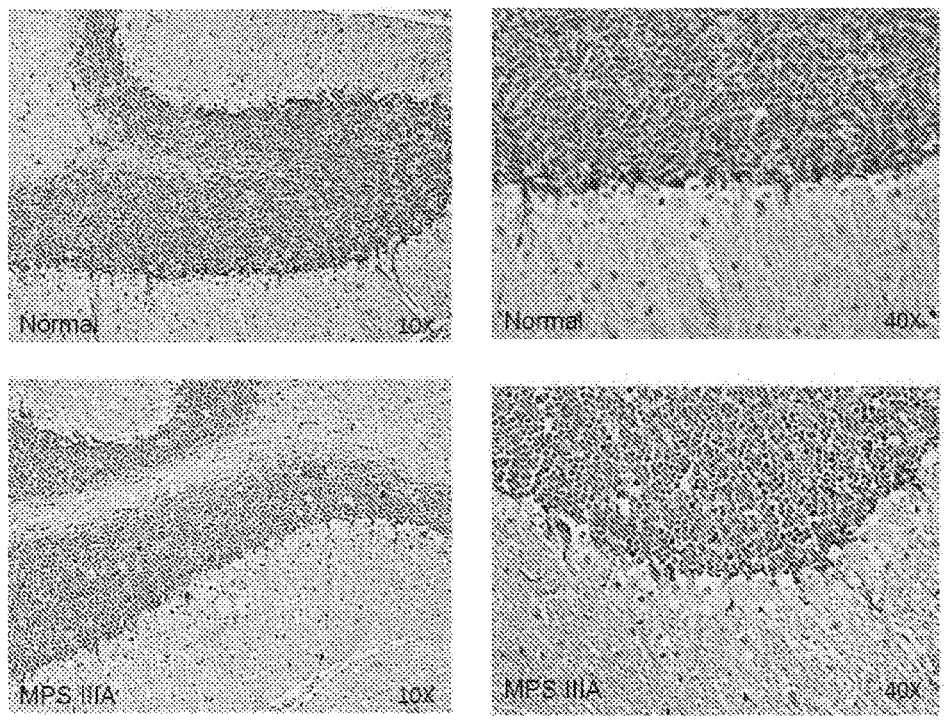
FIG. 24B
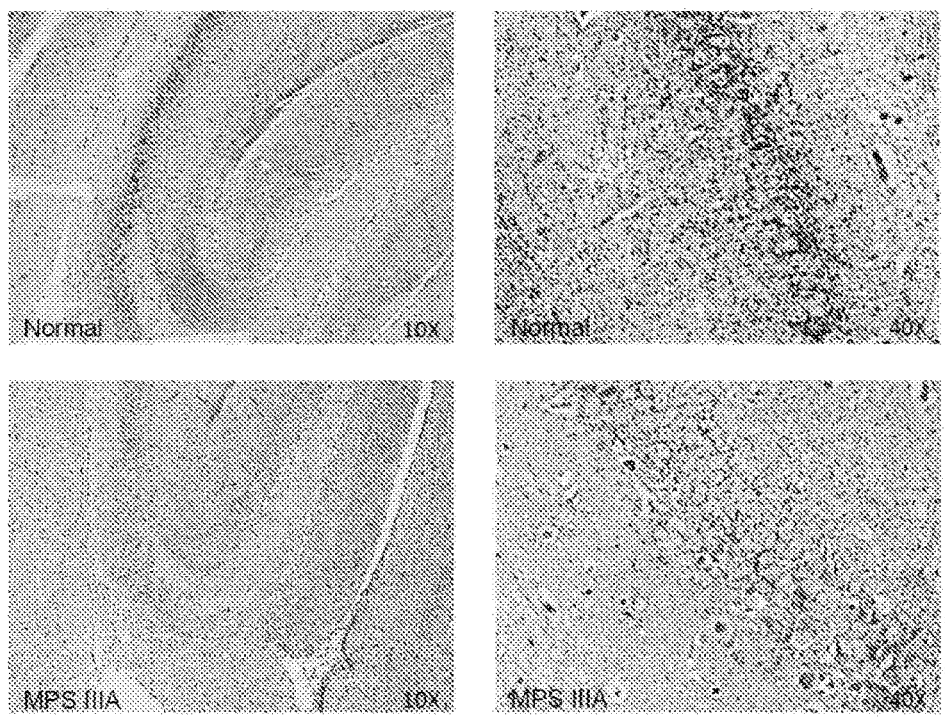

COMPOSITIONS AND METHODS FOR ACTIVATING SIGNALING THROUGH THE CB1 CANNABINOID RECEPTOR FOR TREATING AND PREVENTING DISEASES AND DISORDERS CHARACTERIZED BY ABNORMAL CELLULAR ACCUMULATION OF SPHINGOLIPIDS SUCH AS SPHINGOMYELIN

CROSS-REFERENCE

This application is a U.S. national phase application of International PCT Patent Application No. PCT/US2019/020828, which was filed on Mar. 5, 2019, which claims priority to U.S. Provisional Application No. 62/638,837, filed Mar. 5, 2018, all of which applications are incorporated by reference herein in their entireties.

FIELD OF THE INVENTION

The present disclosure relates to the treatment and prevention of lipid storage disorders. In particular, the present disclosure relates to compositions and methods for increasing endocannabinoid levels in a subject and for activating the CB1 cannabinoid receptor for treating or preventing diseases and disorders that are characterized by abnormal cellular accumulation of sphingolipids including, e.g., sphingomyelin (SM).

BACKGROUND OF THE INVENTION

Sphingolipids are evolutionarily conserved constituents of the plasma membranes of all mammalian cells. Sphingomyelin (SM) is the most abundant sphingolipid in the cell, with ubiquitous distribution within mammalian tissues, and particularly high levels in the Central Nervous System (CNS). SM is an essential element of plasma membrane and its levels are crucial for the cell function. SM content in a cell is strictly regulated by the enzymes of SM metabolic pathways, which create a balance between SM synthesis and degradation. The biosynthesis of sphingolipids starts in the endoplasmic reticulum (ER). SM synthesis is completed in the golgi apparatus through a conversion of ceramide to SM via sphingomyelin synthase. SM is then transported to all other biological membranes.

SM is recycled back to its constituent ceramides and sphingolipids by different enzymes in different compartments and organelles of the cell depending on the structural and signaling requirements and on the body system. This recycling process is referred to as the sphingomyelin cycle. SM can be hydrolyzed back to ceramide by three enzyme groups: ASM (a lysosomal acid enzyme), alkaline sphingomyelinases (found in the outer leaflet of the plasma membrane or released into the lumen of intestines), and neutral sphingomyelinase (NSM), a plasma and other internal organelle membrane bound, magnesium dependent enzyme.

The dysregulation or absence of one sphingolipid enzyme may lead to accumulation or depletion of one or more species of sphingolipids in a specific organelle, which in turn may lead to plasma membrane disruption manifesting in disease.

Acid Sphingomyelinase Deficiency (ASMD) is a spectrum disorder characterized by dysfunctional cellular processing of SM. At the most severe end of the ASMD spectrum is a form of the disease, referred to in the past as Type A Niemann Pick disease (NPA), which includes both neurovisceral and non-neurovisceral symptoms. Patients having this most extreme form of ASMD develop rapidly progressive neurological pathology with prominent loss of motor skills and cognitive decline, as well as systemic organ pathology that includes low levels of platelets, hepatosplenomegaly, and pulmonary dysfunction including lung disease and frequent respiratory infections (Schuchman, Inherit Metab Dis 2007, 30:654-663). Most patients are diagnosed by the appearance of symptoms at 3-6 months after birth and rarely survive longer than 3 years of age. On the other end of the spectrum is a milder form of ASMD, referred to in the past as Type B Niemann Pick disease (NPB), which includes only non-neurovisceral symptoms and is associated with longer life span. Other intermediate forms of these two types exist with a range of symptoms and severity (e.g., sometimes referred to as Type A/B).

ASMD is caused by loss of function mutations in the SMPD1 gene which encodes acid sphingomyelinase (ASM). ASM is a lipid hydrolase that degrades SM into ceramide and phosphatidyl choline in lysosomes. Mutations in this enzyme reduce its enzymatic activity resulting in cellular accumulation of SM and various associated toxicities. SM accumulation is especially relevant in lysosomes (where most of ASM resides) and at the plasma membrane (where a small pool of the enzyme is located). Besides SM, other lipids accumulate like sphingosine and gangliosides GM2 and GM3. The differences between NPA, NPB, and the intermediate forms of ASMD relate to the residual ASM activity remaining after the mutations. In NPA, residual ASM activity is very low (less than 5% of normal activity), whereas NPB patients (and patients with intermediate forms of ASMD) show higher residual ASM activity.

Of relevance, it is important to note that in some disorders, including lysosomal disorders, SM accumulates and contributes to pathology despite the fact that there are no mutations in the SMPD1 gene. Indeed, lysosomal storage disorders are a diverse group of genetic diseases due to specific gene/protein defects and the accumulation of specific substrates, but they share several common pathogenic mechanisms. For example, accumulation of the primary substrate in any individual lysosomal disorder will eventually lead to the overall dysfunction of the lysosomal system, including dysfunction of other enzymes within the lysosomes, and the eventual buildup of many secondary substrates. Many of these accumulating secondary substrates are pathogenic and common among the lysosomal disorders, including the sphingolipids ceramide and sphingosine. Since ceramide is the precursor for all other complex sphingolipids, including sphingomyelin and gangliosides, these lipids often accumulate as well. Thus, in many, if not all, instances the pathology of any given lysosomal disease is due not only the accumulation of the primary substrate, but to the buildup of these additional substrates as well, and the eventual disruption of the cellular, lysosomal apparatus.

One example of this is the lysosomal storage disorder, Type C Niemann-Pick disease, in which the primary accumulating lipid is cholesterol, but secondary SM accumulation also occurs and contributes to the disease (Devlin et al., Traffic, 11(5):601, 2010). Indeed, many other diseases are known to accumulate ceramide, including but not limited to Farber disease, Gaucher disease, Type AB Niemann-Pick disease, several mucopolysaccharidoses, Pompe disease and others. As noted above, the complex sphingolipid, sphingomyelin, could also be accumulating and contributing to pathology in any of these disorders as well. For example, in addition to Types A, B, and C of Niemann-Pick disease, sphingomyelin is known to accumulate in Farber disease, Gaucher disease, Fabry disease, Sanfilippo Disease (MPS IIIA) and others.

Thus, reduction of SM levels is a key therapeutic target in NPA, NPB, and other SM-related lysosomal storage disorders that exhibit SM accumulation.

SUMMARY OF THE INVENTION

The present disclosure relates to, inter alia, compositions and methods for treating and preventing diseases and disorders characterized by the aberrant production or storage of sphingolipids (such as, e.g., sphingomyelin). In particular embodiments, the present disclosure relates to compositions and methods for increasing endocannabinoid levels and for activating the CB1 cannabinoid receptor for treating or preventing diseases and disorders that are characterized by abnormal cellular accumulation of sphingolipids including, e.g., sphingomyelin (SM). The present invention is based in part on the surprising discovery that CB1 receptor expression is decreased in a human patients and/or mouse models of ASMD (NPA), NPC, and MPS IIIA, which have diverse molecular pathogenesis, but all exhibit aberrant lipid storage (e.g., sphingomyelin accumulation). Thus, the present invention provides, inter alia, compositions and methods for increasing endocannabinoids and/or activating CB1 signaling.

In some embodiments, the present disclosure provides a method comprising modulating cellular sphingomyelin (SM) levels in a subject that has a lysosomal storage disease or disorder in which sphingomyelin (SM) accumulates comprising, activating the CB1 cannabinoid receptor.

In some embodiments, the present disclosure provides a method of inhibiting the cellular accumulation of sphingomyelin (SM) in a subject that has Acid Sphingmyelinase Deficiency (ASMD) comprising, administering to the subject a fatty acid amide hydrolase (FAAHi) inhibitor.

In some embodiments, the present disclosure provides a method of inhibiting a loss of motor skills, cognitive decline, and/or systemic organ pathology associated with ASMD comprising, administering to a subject a fatty acid amide hydrolase (FAAHi) inhibitor.

In some embodiments, the present disclosure provides a method of inhibiting the cellular accumulation of at least one sphingolipid in a subject that has a disease or disorder characterized by aberrant cellular sphingolipid concentrations comprising, administering to a subject a fatty acid amide hydrolase (FAAHi) inhibitor.

In some embodiments, the present disclosure provides a method of inhibiting the accumulation of sphingomyelin (SM) in the brain of a subject that has Niemann Pick disease type A (NPA) comprising, activating neutral sphingomyelinase.

In some embodiments, the present disclosure provides a method of decreasing sphingomyelin (SM) levels in the brain of a subject that has Niemann Pick disease type A (NPA) comprising, activating neutral sphingomyelinase.

In some embodiments, the present disclosure provides a method of inhibiting the cellular accumulation of sphingomyelin (SM) in a subject that has lysosomal storage disease or other disorder in which sphingomyelin (SM) accumulates comprising, activating the CB1 cannabinoid receptor.

In some embodiments, the present disclosure provides a method of inhibiting the accumulation of sphingomyelin (SM) in the brain of a subject that has Niemann Pick disease type A (NPA) comprising, administering to a subject a fatty acid amide hydrolase (FAAHi) inhibitor.

In some embodiments, the present disclosure provides a method of inhibiting the cellular accumulation of sphingomyelin (SM) in a subject that has a lysosomal storage disorder or other disorder in which sphingomyelin (SM) accumulates comprising, administering to a subject a fatty acid amide hydrolase (FAAHi) inhibitor.

In some embodiments, the present disclosure provides a method comprising of modulating cellular sphingomyelin (SM) levels in a subject that has a lysosomal storage disease or disorder in which sphingomyelin (SM) accumulates comprising, increasing the levels of one or more cannabinoids in the subject.

In some embodiments, the present disclosure provides a method of inhibiting a loss of motor skills, cognitive decline, and/or systemic organ pathology associated with a disease or disorder in which sphingomyelin (SM) accumulates comprising, increasing the levels of one or more cannabinoids in the subject.

In some embodiments, the present disclosure provides a method of treating loss of motor skills, cognitive decline, and/or systemic organ pathology associated with a disease or disorder in which sphingomyelin (SM) accumulates comprising, increasing the levels of one or more cannabinoids in the subject.

In some embodiments, the present disclosure provides a method of treating a disease or disorder in which sphingomyelin (SM) accumulates comprising, increasing the levels of one or more cannabinoids in the subject.

In some embodiments, the disease is selected from Acid Sphingomyelinase Deficiency (ASMD), Type A Niemann Pick disease (NPA), Type B Niemann Pick disease (NPB), Type C Niemann Pick disease (NPC), and mucopolysaccharidosis type IIIA (MPS IIIA). In some embodiments, the ASMD is selected from NPA, NPB, and is an intermediate form of ASMD, NPA/B.

In some embodiments, cellular SM levels are decreased by activating CB1. In some embodiments, accumulation of cellular SM levels are inhibited by activating CB1.

In some embodiments, cellular SM levels are modulated in a neuron of the subject. In some embodiments, cellular SM levels are modulated in a purkinje cell of the subject.

In some embodiments, the cannabinoid is exogenous. In some embodiments, the cannabinoid is an endogenous endocannabinoid. In some embodiments, the endocannabinoid is anandamide or 2-AG.

In some embodiments, the CB1 cannabinoid receptor is activated by anandamide or 2-AG. In some embodiments, the anandamide or 2-AG is endogenous. In some embodiments, the CB1 cannabinoid receptor is activated by increasing endogenous anandamide or 2-AG in the subject. In some embodiments, the endogenous anandamide and/or 2-AG is increased by preventing its degradation. For example, in some embodiments, the anandamide degradation is prevented by inhibiting fatty acid amide hydrolase (FAAH). For example, in some embodiments, 2-AG degradation is prevented by inhibiting Monoacylglycerol lipase (MAGL).

Various embodiments comprise inhibiting FAAH, e.g., with a FAAH inhibitor (FAAHi). In some embodiments, the FAAH is inhibited with a FAAHi selected from PF-04457845, AM-3506; AM-5206, IPI-940; IW-6118; BIA-102474; JNJ-1661010; JNJ-40413269; JNJ-42165279; PF-3845; PF-750; SSR411298; URB597; URB694; URB937; and V158866. In some embodiments, the FAAHi is administered to the subject as a pharmaceutical composition. In particular embodiments, the FAAHi is PF-04457845.

In some embodiments, the endogenous 2-AG is increased by stimulating 2-AG production. In some embodiments, the 2-AG production is mediated by activating mGluR5. In some embodiments, the mGluR5 is activated using CDPPB.

In some embodiments, activating the CB1 cannabinoid receptor results in activating neutral sphingomyelinase. In some embodiments, neutral sphingomyelinase is activated by increasing signaling through the CB1 cannabinoid receptor. In some embodiments, neutral sphingomyelinase is activated by increasing endocannabinoid signal transduction. In some embodiments, neutral sphingomyelinase is activated by preventing endocannabinoid degradation. In some embodiments, neutral sphingomyelinase is activated by preventing anandamide degradation. In some embodiments, neutral sphingomyelinase is activated by preventing 2-AG degradation. In some embodiments, neutral sphingomyelinase is activated by preventing anandamide degradation mediated by fatty acid amide hydrolase (FAAH). In some embodiments, the FAAHi inhibitor results in activation of the CB1 cannabinoid receptor. In some embodiments, the FAAHi is selected from PF-04457845, AM-3506; AM-5206, IPI-940; IW-6118; BIA-102474; JNJ-1661010; JNJ-40413269; JNJ-42165279; PF-3845; PF-750; SSR411298; URB597; URB694; URB937; and V158866. In particular embodiments, the FAAHi is PF-04457845. In some embodiments, the FAAHi is administered to the subject as a pharmaceutical composition. In some embodiments, pharmaceutical composition comprises the FAAHi and one or more pharmaceutically acceptable salts, excipients or vehicles. In some embodiments, the pharmaceutical composition comprises one or more agents selected from the group consisting of carriers, excipients, diluents, antioxidants, preservatives, coloring, flavoring and diluting agents, emulsifying agents, suspending agents, solvents, fillers, bulking agents, buffers, delivery vehicles, tonicity agents, co-solvents, wetting agents, complexing agents, buffering agents, antimicrobials, and/or surfactants.

In some embodiments, activating the CB1 cannabinoid receptor reduces sphingomyelin levels in at least one organ of the subject. In some embodiments, a method disclosed herein activates CB1, wherein the CB1 activation treats a lysosomal storage disease or disorder.

In some embodiments, a method of the present disclosure prevents neuronal death in the brain of the subject. In some embodiments, the method improves the subject's cognition, learning and/or memory.

In some embodiments, a method disclosed herein results in an improvement of one or more symptoms associated with ASMD. In some embodiments, the method prevents neuronal death associated with NPA, and/or an intermediate form of NPA/B. In some embodiments, the method improves the subject's cognition. In some embodiments, the method improves the subject's learning and/or memory.

In some embodiments, a method disclosed herein reduces SM levels in the subject. In some embodiments, the method reduces SM levels in a neuron in the brain of the subject. In some embodiments, the method results in reduced SM levels in organs other than the brain. In some embodiments, the other organ is selected from the liver, spleen, lungs, adrenal gland, heart, articular cartilage, articular joint space, and bone marrow.

In some embodiments, a method disclosed herein increases the lifespan of a subject to which the method is applied as compared to the expected lifespan of an individual with the same disease that has not had the method applied.

In some embodiments, a method disclosed herein further comprises administering one or more additional therapeutic agents. In some embodiments, the additional therapeutic agent comprises an acid sphingomyelinase (ASM) replacement therapy. In some embodiments, the ASM replacement therapy comprises administering recombinant ASM to the subject. In some embodiments, the administering of the recombinant ASM to the subject is via a route of administration selected from delivery to the central nervous system, intravenous infusion, intrathecal infusion, intraventricular injection, and combinations thereof. In some embodiments, the ASM replacement therapy comprises administering an autologous cell expressing a gene encoding a functional ASM enzyme to the subject. In some embodiments, the autologous cell is a hematopoietic stem cell. In some embodiments, the autologous cell is genetically engineered to express the gene encoding the functional ASM enzyme. In some embodiments, the gene encoding the functional ASM enzyme has been introduced into the autologous cell via viral infection. In some embodiments, the viral infection is mediated by a recombinant retrovirus, a recombinant lentivirus, or a recombinant adeno-associated virus. In some embodiments, the ASM replacement therapy comprises administering a recombinant virus expressing a gene encoding a functional ASM enzyme to the subject. In some embodiments, the recombinant virus is a recombinant retrovirus, a recombinant lentivirus, or a recombinant adeno-associated virus. In some embodiments, the administering of the recombinant virus is via direct injection of the recombinant virus into subject's brain. In some embodiments, the recombinant virus is administered to the subjection via a route of administration selected from delivery to the central nervous system, intravenous infusion, intrathecal infusion, intraventricular injection, and combinations thereof. In some embodiments, the additional therapeutic agent comprises a glucocorticoid. In some embodiments, the glucocorticoid is dexamethasone or hydrocortisone. In some embodiments, the additional therapeutic agent comprises an HSP70 inhibitor. In some embodiments, the HSP70 inhibitor is arimoclomol. In some embodiments, the additional therapeutic agent comprises an inhibitor of histone deacetylase. In some embodiments, the additional therapeutic agent enhances plasma membrane calcium ATPase (PMCA) expression. In some embodiments, the additional therapeutic agent is the histone deacetylase inhibitor SAHA. In some embodiments, the additional therapeutic agent is an inhibitor of ganglioside production. In some embodiments, the additional agent is an inhibitor of sphingomyelin production. In some embodiments, the additional agent is a sphingomyelin synthase inhibitor.

In some embodiments of the methods disclosed herein, a subject's SM levels decrease following administration of a FAAHi. In some embodiments, the subject's SM levels decrease in the brain of the subject following the administration of the FAAHi. In some embodiments, the subject's SM levels decrease in the neurons of the subject following the administration of the FAAHi.

In some embodiments, the present disclosure provides a combination therapy for treating a lipid storage disorder comprising a first agent that is a FAAHi and a second agent. In some embodiments, the FAAHi is selected from PF-04457845, AM-3506; AM-5206; IPI-940; IW-6118; BIA-102474; JNJ-1661010; JNJ-40413269; JNJ-42165279; PF-3845; PF-750; SSR411298; URB597; URB694; URB937; and V158866. In some embodiments, the FAAHi is PF-04457845. In some embodiments, the additional agent is selected from an enzyme replacement therapy (ERT);

gene therapy, substrate reduction, substrate inhibition, other small molecule, chaperone, and enzyme activation.

BRIEF DESCRIPTION OF THE DRAWINGS

FIG. 5 shows sphingomyelin and endocannabinoid levels in cultured primary hippocampal neurons and hippocampal tissue, respectively, from ASMko and wildtype mice. FIG. 5A shows mean±SEM sphingomyelin levels (as percentage of control values) in cultured primary hippocampal neurons from ASMko mice non treated (control) or incubated with anandamide (AEA) or with the FAAHi PF-04457845 (PF) in the presence or absence of the neutral sphingomyelinase inhibitor GW4869 for 1 hour at the indicated concentrations (n=3 independent cultures, ***p<0.001). FIG. 5B shows that anandamide levels are unchanged in the hippocampus of ASMko mice as compared to wildtype mice. FIG. 5C shows that ASMko mice have significantly reduced levels of 2-AG (*p<0.05). FIG. 5D shows that the allosteric mGluR5 agonist CDPPB significantly decreases sphingomyelin levels in ASMko cultured neurons (n=3 different cultures/condition, *p<0.05).

FIG. 10 shows treatments with anandamide, URB597, PF-04457845 or JNJ-1661010 at 50 µM for 1 h do not promote evident alterations in dendrites of ASMko cultured neurons.

FIG. 13 shows the effect of PF-04457845 treatment on various behavioral functions. FIG. 13A shows mean±SEM time that wt and ASMko mice treated or not with PF-04457845 spent on the new arm of a Y maze as percentage of the total exploration time (n=14; *p<0.05). FIG. 13B shows mean±SEM time in seconds during which wt and ASMko mice treated or not with PF-04457845 were immobile while they were suspended from the tail. (n=14; **p<0.01, *p<0.05). FIG. 13C shows mean±SEM percentage of time that wt and ASMko mice treated or not with PF-04457845 spent in the open arm of the Elevated Plus Maze (n=14; *p<0.05).

FIG. 15 shows representative images of Purkinje cells from wildtype and ASMko mice treated or not treated with PF-04457845.

FIG. 19 shows the percentage of survival in weeks of wt and ASMko mice treated or not treated with PF-04457845 (n=7).

FIG. 22 shows that CB1 levels are slightly reduced in cultured fibroblasts from NPA patients as compared to control patients.

FIG. 24 shows decreases in CB1 receptor expression in the brains of MPS IIIA mice. FIG. 24A shows CB1 expression in the hippocampus of normal and MPS IIIA mice. FIG. 24B shows CB1 expression in the cerebellum of normal and MPS IIIA mice.

FIG. 27 shows H&E staining in wt and ASMko mice treated or not treated with PF-04457845.

FIG. 29 shows representative images of immunofluorescence against iba1, a marker for microglia, which is used as a readout for inflammation.

DETAILED DESCRIPTION OF THE INVENTION

Figure 1:
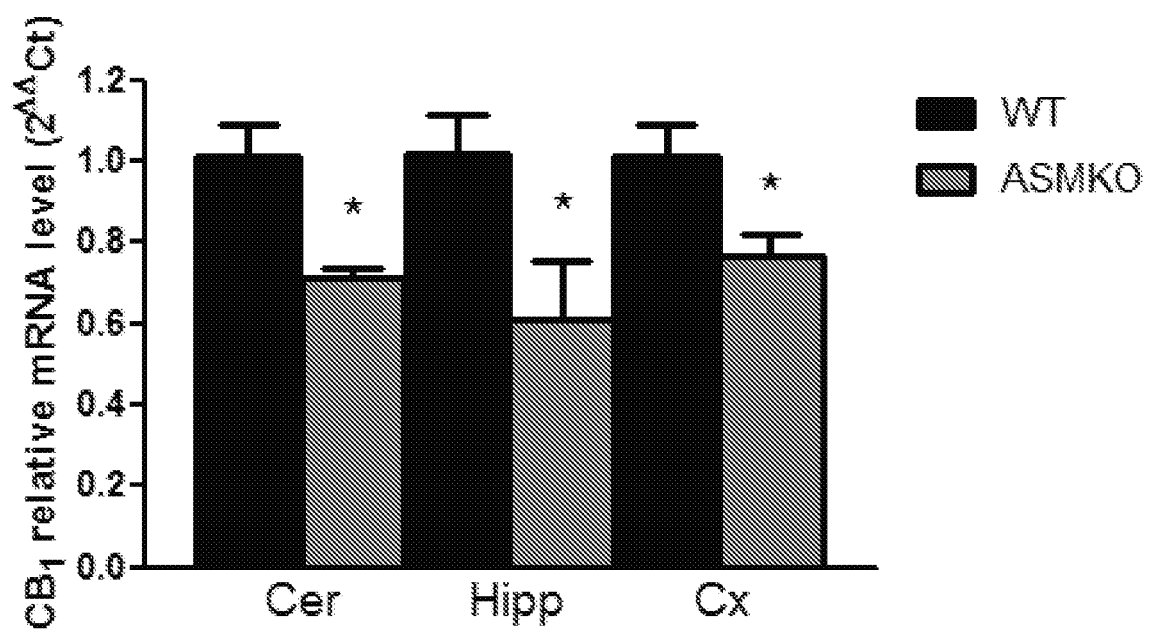
FIG. 1 shows mean±SEM CB1 mRNA levels in extracts from the cerebellum (Cer), hippocampus (Hipp) and Cortex (CX) from wt and ASMko mice (n=4; *p<0.05).

The practice of the present invention will employ, unless indicated specifically to the contrary, conventional methods of molecular biology, recombinant DNA techniques, protein expression, and protein/peptide/carbohydrate chemistry within the skill of the art, many of which are described below for the purpose of illustration. Such techniques are explained fully in the literature. See, e.g., Sambrook, et al., *Molecular Cloning: A Laboratory Manual* (3rd Edition, 2000); *DNA Cloning: A Practical Approach*, vol. I & II (D. Glover, ed.); *Oligonucleotide Synthesis* (N. Gait, ed., 1984); *Oligonucleotide Synthesis: Methods and Applications* (P. Herdewijn, ed., 2004); *Nucleic Acid Hybridization* (B. Hames & S. Higgins, eds., 1985); *Nucleic Acid Hybridization: Modern Applications* (Buzdin and Lukyanov, eds., 2009); *Transcription and Translation* (B. Hames & S. Higgins, eds., 1984); *Animal Cell Culture* (R. Freshney, ed., 1986); Freshney, R. I. (2005) *Culture of Animal Cells, a Manual of Basic Technique*, 5$^{th}$ Ed. Hoboken NJ, John Wiley & Sons; B. Perbal, *A Practical Guide to Molecular Cloning* (3$^{rd}$ Edition 2010); Farrell, R., *RNA Methodologies: A Laboratory Guide for Isolation and Characterization* (3$^{rd}$ Edition 2005). Poly(ethylene glycol), *Chemistry and Biological Applications*, ACS, Washington, 1997; Veronese, F., and J. M. Harris, Eds., *Peptide and protein PEGylation, Advanced Drug Delivery Reviews*, 54(4) 453-609 (2002); Zalipsky, S., et al., "Use of functionalized Poly(Ethylene Glycols) for modification of polypeptides" in Polyethylene Glycol Chemistry: Biotechnical and Biomedical Applications. The publications discussed above are provided solely for their disclosure before the filing date of the present application. Nothing herein is to be construed as an admission that the invention is not entitled to antedate such disclosure by virtue of prior invention.

DEFINITIONS AND ABBREVIATIONS

Unless defined otherwise, all technical and scientific terms used herein have the same meaning as commonly understood by one of ordinary skill in the art to which this invention belongs. As used in the specification and appended claims, unless specified to the contrary, the following terms have the meaning indicated. With regard to this specification, any time a definition of a term as defined herein, differs from a definition given for that same term in an incorporated reference, the definition explicitly defined herein is the correct definition of the term.

The words "a" and "an" denote one or more, unless specifically noted.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length. In any embodiment discussed in the context of a numerical value used in conjunction with the term "about," it is specifically contemplated that the term about can be omitted.

A "composition" can comprise an active agent and a carrier, inert or active, e.g., a pharmaceutically acceptable carrier, diluent or excipient. In particular embodiments, the compositions are sterile, substantially free of endotoxins or non-toxic to recipients at the dosage or concentration employed.

Unless the context requires otherwise, throughout the present specification and claims, the word "comprise" and variations thereof, such as, "comprises" and "comprising" are to be construed in an open and inclusive sense, that is, as "including, but not limited to".

By "consisting of" is meant including, and limited to, whatever follows the phrase "consisting of." Thus, the phrase "consisting of" indicates that the listed elements are required or mandatory and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Reference throughout this specification to "biological activity" or "bioactivity" refers to any response induced in an in vitro assay or in a cell, tissue, organ, or organism, (e.g., an animal, or a mammal, or a human) as the result of administering any compound, agent, polypeptide, conjugate, pharmaceutical composition contemplated herein. Biological activity may refer to agonistic actions or antagonistic actions. The biological activity may be a beneficial effect; or the biological activity may not be beneficial, i.e. a toxicity. In some embodiments, biological activity will refer to the positive or negative effects that a drug or pharmaceutical composition has on a living subject, e.g., a mammal such as a human. Accordingly, the term "biologically active" is meant to describe any compound possessing biological activity, as herein described. Biological activity may be assessed by any appropriate means currently known to the skilled artisan. Such assays may be qualitative or quantitative. The skilled artisan will readily appreciate the need to employ different assays to assess the activity of different polypeptides; a task that is routine for the average researcher. Such assays are often easily implemented in a laboratory setting with little optimization requirements, and more often than not, commercial kits are available that provide simple, reliable, and reproducible readouts of biological activity for a wide range of polypeptides using various technologies common to most labs. When no such kits are available, ordinarily skilled researchers can easily design and optimize in-house bioactivity assays for target polypeptides without undue experimentation; as this is a routine aspect of the scientific process.

Reference to the term "e.g." is intended to mean "e.g., but not limited to" and thus it should be understood that whatever follows is merely an example of a particular embodiment, but should in no way be construed as being a limiting example. Unless otherwise indicated, use of "e.g." is intended to explicitly indicate that other embodiments have been contemplated and are encompassed by the present invention.

Reference throughout this specification to "embodiment" or "one embodiment" or "an embodiment" or "some embodiments" or "certain embodiments" means that a particular feature, structure or characteristic described in connection with the embodiment is included in at least one embodiment of the present invention. Thus, the appearances of the phrases "in one embodiment" or "in an embodiment" or "in certain embodiments" in various places throughout this specification are not necessarily all referring to the same embodiment. Furthermore, the particular features, structures, or characteristics may be combined in any suitable manner in one or more embodiments.

An "increased" or "enhanced" amount is typically a "statistically significant" amount, and may include an increase that is 1.1, 1.2, 1.3, 1.4, 1.5, 1.6, 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 2.1, 2.2, 2.3, 2.4, etc.) an amount or level described herein. Similarly, a "decreased" or "reduced" or "lesser" amount is typically a "statistically significant" amount, and may include a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein.

The terms "in vitro", "ex vivo", and "in vivo" are intended herein to have their normal scientific meanings. Accordingly, e.g., "in vitro" is meant to refer to experiments or reactions that occur with isolated cellular components, such as, e.g., an enzymatic reaction performed in a test tube using an appropriate substrate, enzyme, donor, and optionally buffers/cofactors. "Ex vivo" is meant to refer to experiments or reactions carried out using functional organs or cells that have been removed from or propagated independently of an organism. "In vivo" is meant to refer to experiments or reactions that occur within a living organism in its normal intact state.

The term "CDPPB" refers to 3-Cyano-N-(1,3-diphenyl-1H-pyrazol-5-yl)benzamide, which is an allosteric agonist of mGluR5 and is available commercially (e.g., Tocris, Bristol, United Kingdom). The structure of CDPPB is shown below:

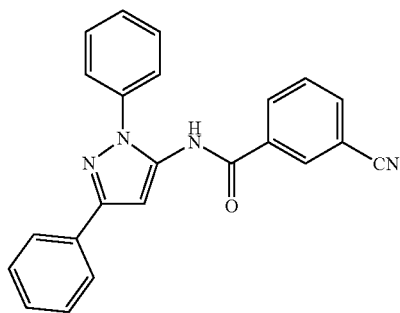 [SMILES: N#Cc1cccc(C(=O)Nc2cc(-c3ccccc3)nn2-c2ccccc2)c1]

The term "PF-04457845" refers to a highly selective fatty acid amide hydrolase inhibitor that is known in the art and is available commercially (e.g., Tocris, Bristol, United Kingdom). The structure of PF-04457845 is shown below:

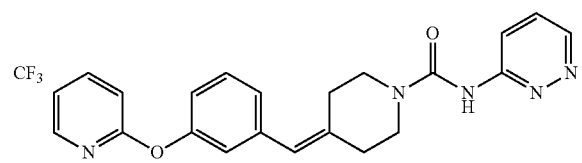 [SMILES: "CF3" ; O=C(Nc1cccnn1)N1CCC(=Cc2cccc(Oc3ccccn3)c2)CC1]

"Mammal" includes humans and both domestic animals such as laboratory animals and household pets, (e.g., cats, dogs, swine, cattle, sheep, goats, horses, and rabbits), and non-domestic animals such as wildlife and the like.

"Optional" or "optionally" means that the subsequently described event, or circumstances, may or may not occur, and that the description includes instances where said event or circumstance occurs and instances in which it does not.

"Pharmaceutical composition" refers to a formulation of a compound (e.g. a therapeutically useful polypeptide) and a medium generally accepted in the art for the delivery of the compound to an animal, e.g., humans. Such a medium may include any pharmaceutically acceptable carriers, diluents or excipients therefore.

"Pharmaceutically effective excipients" and "pharmaceutically effective carriers" are well known to those of skill in the art, and methods for their preparation are also readily apparent to the skilled artisan. Such compositions, and methods for their preparation, may be found, e.g., in Remington's Pharmaceutical Sciences, 19th Edition (Mack Publishing Company, 1995, incorporated herein).

The terms "polynucleotide", "nucleotide", "nucleotide sequence", and "nucleic acid" are used interchangeably. They refer to a polymeric form of nucleotides of any length, either deoxyribonucleotides or ribonucleotides, or analogs thereof. Polynucleotides may have any three-dimensional structure, and may perform any function known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may include non-nucleotide components. A polynucleotide may be further modified after polymerization, such as by conjugation with a labeling component.

A "subject," as used herein, includes any animal that exhibits a disease or symptom, or is at risk for exhibiting a disease or symptom, which can be treated with an agent of the invention. Suitable subjects include laboratory animals (such as mouse, rat, rabbit, or guinea pig), farm animals, and domestic animals or pets (such as a cat or dog). Non-human primates and, preferably, human patients, are included.

"Substantially" or "essentially" means of ample or considerable amount, quantity, size; nearly totally or completely; for instance, 95% or greater of some given quantity.

"Therapeutic agent" refers to any compound that, when administered to a subject, (e.g., preferably a mammal, more preferably a human), in a therapeutically effective amount is capable of effecting treatment of a disease or condition as defined below.

"Therapeutically effective amount" or "Therapeutically effective dose" refers to an amount of a compound of the invention that, when administered to a subject, (e.g., preferably a mammal, more preferably a human), is sufficient to effect treatment, as defined below, of a disease or condition in the animal. The amount of a compound of the invention that constitutes a "therapeutically effective amount" will vary depending on the compound, the condition and its severity, the manner of administration, and the age of the animal to be treated, but can be determined routinely by one of ordinary skill in the art having regard to his own knowledge and to this disclosure.

"Treating" or "treatment" as used herein covers the treatment of the disease or condition of interest in a subject, preferably a human, having the disease or condition of interest, and includes: (i) preventing or inhibiting the disease or condition from occurring in a subject, in particular, when such subject is predisposed to the condition but has not yet been diagnosed as having it; (ii) inhibiting the disease or condition, i.e., arresting its development; (iii) relieving the disease or condition, i.e., causing regression of the disease or condition; or (iv) relieving the symptoms resulting from the disease or condition. As used herein, the terms "disease," "disorder," and "condition" may be used interchangeably or may be different in that the particular malady, injury or condition may not have a known causative agent (so that etiology has not yet been worked out), and it is, therefore, not yet recognized as an injury or disease but only as an undesirable condition or syndrome, wherein a more or less specific set of symptoms have been identified by clinicians.

OVERVIEW

The present disclosure provides, inter alia, compositions and methods for treating and preventing diseases and disorders characterized by the aberrant production or storage of sphingolipids. In some embodiments, the present disclosure relates to compositions and methods for activating the CB1 cannabinoid receptor for treating or preventing diseases and disorders that are characterized by abnormal cellular accumulation of sphingolipids including, e.g., sphingomyelin (SM). In particular embodiments, the present disclosure relates to compositions and methods for increasing levels of endocannabinoids for treating or preventing diseases and disorders that are characterized by abnormal cellular accumulation of sphingolipids including, e.g., sphingomyelin (SM). The present invention is based in part on the surprising discovery that the expression of the cannabinoid receptor CB1 is aberrantly reduced in the brains of human patients suffering from ASMD and in both the brain and cultured neurons of ASMko mice, a well characterized mouse model of ASMD. Further, the data presented herein demonstrates that treatment of AMSko cultured neurons with the CB1 agonist anandamide (AEA), or with a FAAHi to decrease AEA degradation and thereby indirectly increase AEA levels, lead to a marked reduction in SM levels, as does stimulation of increased production of the endocannabinoid 2-AG via activation of the glutamatergic receptor mGluR5. Further, when compositions that lead to increased CB1 activity are administered in vivo, improvements in motor and cognitive abilities are observed in combination with reduction of SM levels in the brain, liver and spleen, increased body weight, prevention of neuronal death and increased lifespan in both male and female ASMko mice. CB1 reduced levels are also observed in the brain mouse models for Niemann Pick diseases type C (NPC) and mucopolysaccharidosis type IIIA, two other lysosomal storage disorders with severe neurological involvement where sphingolipids, including sphingomyelin, accumulate.

Accordingly, in some embodiments, the present disclosure concerns compositions and methods for treating or preventing aberrant cellular sphingomyelin accumulation in subjects with ASMD. The present disclosure also concerns compositions and methods for treating or preventing lipid storage disorders such as, e.g., ASMD, NPA, NPB, NPC and MPS IIIA. The present disclosure also concerns compositions and methods for reducing cellular sphingomyelin levels in such ASMD subjects, and compositions and methods for reducing cellular sphingomyelin in subjects with NPC or MPS IIIA.

ASMD is caused by loss of function mutations in the SMPD1 gene, which encodes acid sphingomyelinase (ASM). ASM is a lipid hydrolase that degrades SM into ceramide and phosphatidyl choline in lysosomes.

Studies performed in a knockout mouse model lacking the ASM gene (ASMko) (Horinouchi et al., Nat Genet 1995, 10:288-293) and in NPA patient cells have demonstrated that abnormal accumulation of SM is the principal pathological event leading to brain cell alterations, including molecular distribution of cell surface proteins (Galvan et al., Mol Biol Cell 2008, 19:509-522), synaptic plasticity (Arroyo et al., EMBO Mol Med 2014, 6:398-413), autophagy (Gabande-Rodriguez et al., Cell Death Diff 2014, 21:864-875) and calcium homeostasis (Perez-Cañamas et al., Mol Psychiatry 2017, 22:711-772). Thus, reduction of SM levels is a key therapeutic target in ASMD.

Enzyme replacement therapy by intravenous infusion of recombinant ASM has proven successful to treat peripheral organs (Wasserstein et al., Mol Genet Metab 2015, 116:88-97). However, this strategy does not impact the brain since the infused recombinant enzyme cannot cross the brain blood barrier (Miranda et al., FASEB J 2000).

A recent open-label Phase 1B study in NPB patients has confirmed the safety and efficacy of the ERT strategy to treat only non-neurological pathology (Wasserstein et al., Mol Genet Metab 2015). Direct delivery of recombinant ASM into lateral ventricles of the ASMko mouse brain partially ameliorated the pathological phenotype (Dodge et al., Exp Neurol 2009) but the same procedure in non-human primates resulted in very poor brain diffusion of the enzyme (Ziegler et al., Exp Neurol 2011).

Replacement of the defective ASM gene has also been assessed. Hematopoietic stem cell therapy in which ASMko bone marrow cells transduced with a retroviral vector encoding human ASM were transplanted into ASMko mice led to visceral improvement but neurological abnormalities were only delayed (Miranda et al., Gene Therapy 2000). Direct brain injections of different adeno-associated viral vector (AAV) serotypes carrying a competent copy of the human ASM gene have been tested in ASMko mice. Reduction in sphingomyelin levels and improved pathological signs were observed but limited to the injection site and immediate surrounding areas (Barbon et al., Mol Ther 2005; dodge et al., PNAS 2005; Passini et al., Mol Ther 2005; Passini et al., PNAS 2007). Moreover, direct brain injection of the AAV vectors in non-human primates elicited robust inflammation and behavioral anomalies (Salegio et al., Hum Gene Ther 2012).

Strategies aimed at addressing the neurological consequences of sphingomyelin accumulation in ASMD have also been evaluated. One of such consequences is the impairment of the plasma membrane calcium ATPase (PMCA) leading to increased calcium levels and oxidative stress in ASMko neurons (Perez-Cañamas et al., Mol Psy 2017). Oral treatment with the histone deacetylase inhibitor SAHA, which enhances PMCA expression in the brain, normalized calcium levels and reduced oxidative stress in neurons of ASMko mice improving behavior and preventing neuronal death (Perez-Cañamas et al., Mol Psy 2017). However, histone deacetylase inhibitors may have multiple gene targets besides PMCA and their safety in humans has not yet been demonstrated.

Thus, there remains a need in the art for safe and effective ways of treating ASMD, and other lysosomal storage disorders associated with aberrant cellular accumulation of SM. In particular, although many of the above-mentioned techniques improved peripheral pathology associated with ASMD, brain pathology was not effectively treated. In addition, some of these approaches required invasive administration and others have serious secondary effects in long-term treatments. Accordingly, the present invention provides a non-invasive strategy for reducing sphingomyelin levels both in the brain and in the periphery using compounds already known to be safe in healthy humans.

In some aspects, the present disclosure provides a method of inhibiting the cellular accumulation of sphingomyelin (SM) in a subject (e.g., a mammal, preferably a human) that has low CB1 expression. In some aspects, the method comprises administering to the subject an agent that is an activator of CB1. In some aspects, the method comprises administering to the subject an agent that increases endogenous endocannabinoids. In some aspects, the agent stimulates production of the endocannabinoid. In some aspects, the agent inhibits degradation of the endocannabinoid. In some aspects the endocannabinoid is anandamide. In some aspects the endocannabinoid is 2-AG. In some aspects, the method comprises administering to the subject a fatty acid amide hydrolase ("FAAHi") inhibitor. In some aspects, the method comprises administering to the subject the fatty acid amide hydrolase inhibitor PF-04457845. In some aspects, the method comprises administering a FAAHi (e.g., PF-04457845) and an additional agent (such as any additional agent disclosed herein as suitable for use in a combination therapy with an FAAHi).

In some aspects, the present disclosure provides a method of inhibiting the cellular accumulation of sphingomyelin (SM) in a subject (e.g., a mammal, preferably a human) that has ASMD comprising, administering to the subject a fatty acid amide hydrolase ("FAAHi") inhibitor (e.g., PF-04457845).

The FAAHi may be any FAAHi disclosed herein or known in the art. For example, suitable FAAH inhibitors include: AM-3506 (National Institute on Alcohol Abuse and Alcoholism); AM-5206 (MAKScientific, LLC); IPI-940 (FAAH Pharma Inc, US20090099131 incorporated herein by reference in its entirety); IW-6118 (Ironwood Pharmaceuticals Inc); BIA-102474; JNJ-1661010 (Johnson & Johnson, "J&J"); JNJ-40413269 (J&J); JNJ-42165279 (J&J); PF-04457845 ("PF")(Pfizer); PF-3845 (Pfizer); PF-750 (Pfizer); SSR411298 (Sanofi); URB597 (Merck & Co); URB694 (Istituto Italiano di Tecnologia); URB937 (Merck & Co); and V158866 (Vernalis).[1] In particular embodiments the FAAHi is PF-04457845. In some embodiments, the subject may have a form of ASMD that is characterized by only non-neurovisceral symptoms (i.e., NPB), or in some embodiments, the subject may have a form of ASMD that is characterized by both neurovisceral and non-neurovisceral symptoms (i.e., NPA or NPA/B intermediate form). Thus, in one particular embodiment, the present disclosure provides a method of inhibiting the cellular accumulation of SM in a subject (e.g., a human) that has ASMD comprising, administering PF-04457845 to the subject.

[1] See, e.g., PMID Nos: 21095576, 23083016, 21069475, 19095868, 18693015, 24513048, 26713105, NCT02432703, 21505060, 23731552, 21506952, 19389627, 17949010, 26713105, 12461523, 16834756, 17949010, 16018870, 26391492, 26987975, and NCT01634529.

In some aspects, the present disclosure provides a method of treating, preventing, or attenuating any one or more symptoms associated with ASMD comprising administering to the subject an agent that activates the cannabinoid receptor CB1. In some aspects, the present disclosure provides a method of treating, preventing, or attenuating any one or more symptoms associated with ASMD comprising administering to the subject an agent that induces increased levels of one or more endocannabinoid (e.g., anandamide and/or 2-AG). The agent may be a FAAHi (e.g., PF-04457845). In some aspects, the present disclosure provides a method of inhibiting a loss of motor skills, cognitive decline, and/or systemic organ pathology associated with ASMD comprising, administering to a subject an agent that activates the cannabinoid receptor CB1. In some aspects, the present disclosure provides a method of inhibiting a loss of motor skills, cognitive decline, and/or systemic organ pathology associated with ASMD comprising, administering to a subject an agent that induces increased levels of one or more endocannabinoid (e.g., anandamide and/or 2-AG). The agent may be a fatty acid amide hydrolase (FAAHi) inhibitor (e.g., PF-04457845). The systemic organ pathology may be, e.g., hepatosplenomegaly. The systemic organ pathology may be, e.g., pulmonary dysfunction.

In some aspects, the present disclosure provides a method of treating, preventing, or attenuating any one or more symptoms associated with ASMD comprising administering to the subject a FAAHi (e.g., PF-04457845). In some aspects, the present disclosure provides a method of inhibiting a loss of motor skills, cognitive decline, and/or systemic organ pathology associated with ASMD comprising, administering to a subject a fatty acid amide hydrolase (FAAHi) inhibitor (e.g., PF-04457845). The systemic organ pathology may be, e.g., hepatosplenomegaly. The systemic organ pathology may be, e.g., pulmonary dysfunction.

In some aspects, the present disclosure provides a method of inhibiting the cellular accumulation of at least one sphingolipid (e.g., SM) in a subject that has a disease or disorder characterized by the aberrant accumulation of at least one sphingolipid comprising, administering to a subject a fatty acid amide hydrolase (FAAHi) inhibitor (e.g., PF-04457845). The disease or disorder may be NPB. The disease or disorder may be NPC. The disease or disorder may be MPS IIIA. The sphingolipid may be SM.

In some aspects, the present disclosure provides a method of treating, preventing, or attenuating any one or more of a subject's symptom associated with high SM comprising administering to the subject a FAAHi (e.g., PF-04457845). In some aspects, the present disclosure provides a method of inhibiting a loss of motor skills, cognitive decline, and/or systemic organ pathology associated with ASMD comprising, administering to a subject a fatty acid amide hydrolase (FAAHi) inhibitor (e.g., PF-04457845). The systemic organ pathology may be, e.g., hepatosplenomegaly. The systemic organ pathology may be, e.g., pulmonary dysfunction.

In some aspects, the present disclosure provides a method of treating, preventing, or attenuating any one or more of a subject's symptom associated with high SM comprising administering to the subject an activator of CB1. In some embodiments, the activator of CB1 is anandamide. In some embodiments, the activator of CB1 is 2-AG. In some embodiments, the activator of CB1 is a FAAHi (e.g., PF-04457845). In some embodiments, the activator of CB1 is CDPPB. In some aspects, the present disclosure provides a method of inhibiting a loss of motor skills, cognitive decline, and/or systemic organ pathology associated with ASMD comprising, administering to a subject an activator of CB1 (e.g., a fatty acid amide hydrolase (FAAHi) inhibitor (e.g., PF-04457845)). The systemic organ pathology may be, e.g., hepatosplenomegaly. The systemic organ pathology may be, e.g., pulmonary dysfunction.

In some aspects, the present disclosure provides a method of restoring "normal" cellular lipid levels (i.e., cellular lipid concentrations that are similar to the concentrations found in subjects that do not have ASMD, or that are substantially identical to the concentrations found in subjects that do not have ASMD) in a subject that has a disorder characterized by aberrant cellular concentrations of at least one lipid comprising, administering to a subject a fatty acid amide hydrolase (FAAHi) inhibitor (e.g., PF-04457845). The lipid storage disorder may be a sphingolipid storage disorder. The sphingolipid may be sphingomyelin. The lipid storage disorder may be ASMD. The ASMD may be NPA, NPB, or NPA/B. The FAAHi may be any FAAHi disclosed herein. The FAAHi may be PF-04457845.

In some aspects, the present disclosure provides a method of restoring "normal" cellular sphingolipid levels (i.e., cellular sphingolipid concentrations that are similar to the concentrations found in subjects that do not have ASMD, or that are substantially identical to the concentrations found in subjects that do not have ASMD) in a subject that has a disorder characterized by aberrant cellular concentrations of at least one sphingolipid comprising, administering to a subject a fatty acid amide hydrolase (FAAHi) inhibitor (e.g., PF-04457845). The sphingolipid may be sphingomyelin.

In some aspects, the present disclosure provides a method of improving or maintaining cellular lipid levels (e.g., in a subject that has a disorder characterized by aberrant cellular concentrations of at least one lipid) comprising activating CB1 and/or increasing endocannabinoid levels in the subject. In some aspects, CB1 is activated by administering to a subject a fatty acid amide hydrolase (FAAHi) inhibitor (e.g., PF-04457845). In some aspects, endocannabinoids are increased by administering to a subject a fatty acid amide hydrolase (FAAHi) inhibitor (e.g., PF-04457845). The lipid storage disorder may be a sphingolipid storage disorder. The sphingolipid may be sphingomyelin. The lipid storage disorder may be ASMD. The ASMD may be NPA, NPB, or NPA/B. The FAAHi may be any FAAHi disclosed herein. The FAAHi may be PF-04457845.

In some aspects, the present disclosure provides a method of improving or maintaining cellular lipid levels (e.g., in a subject that has a disorder characterized by aberrant cellular concentrations of at least one sphingolipid) comprising, administering to a subject a fatty acid amide hydrolase (FAAHi) inhibitor (e.g., PF-04457845). The sphingolipid may be sphingomyelin.

In some aspects, the present disclosure provides a method of inhibiting the accumulation of sphingomyelin (SM) in the brain of a subject that has ASMD (e.g., Niemann Pick disease type A (NPA)) comprising, activating CB1. CB1 may be activated in a neuron. CB1 may be activated in a purkinje cell. CB1 may be activated indirectly. CB1 may be activated directly. CB1 may be activated via increasing endocannabinoid signalling through the CB1 cannabinoid receptor. CB1 may be activated via the administration of an exogenous cannabinoid. CB1 may be activated via administration of an agent that increases expression or accumulation of an endogenous CB1 agonist. CB1 may be activated via administration of anandamide. CB1 may be activated via administration of a compound that inhibits the degradation of anandamide. For example, CB1 may be activated via administration of a FAAHi, which inhibits the hydrolyzation of anandamide by FAAH. This indirectly leads to increased anandamide levels, which in turn binds to and activates CB1, which may in turn lead to subsequent neutral sphingomyelinase activation and breakdown of SM. The neutral sphingomyelinase may be activated via administration of anandamide and via administration of a FAAHi. CB1 may be activated via administration 2-AG. CB1 may be activated via administration a compound that inhibits the degradation of 2-AG. CB1 may be activated via administration a compound that promotes the production of 2-AG. CB1 may be activated via production of 2-AG via activation of a glutamate receptor. CB1 may be activated via production of 2-AG via activation of mGluR5. CB1 may be activated via production of 2-AG via activation of mGluR5 with its allosteric activator CDPPB.

In some aspects, the present disclosure provides a method of inhibiting the accumulation of sphingomyelin (SM) in the brain of a subject that has Niemann Pick disease type A (NPA) comprising, activating neutral sphingomyelinase. The neutral sphingomyelinase may be activated indirectly. The neutral sphingomyelinase may be activated directly. The neutral sphingomyelinase may be activated via signalling through the CB1 cannabinoid receptor. The neutral sphingomyelinase may be activated via the administration of an exogenous cannabinoid. The neutral sphingomyelinase may be activated via administration of an agent that increases expression or accumulation of an endogenous CB1 agonist. The neutral sphingomyelinase may be activated via administration of anandamide. The neutral sphingomyelinase may be activated via administration of a compound that inhibits the degradation of anandamide. For example, neutral sphingomyelinase may be activated via administration of a FAAHi, which inhibits the hydrolyzation of anandamide by FAAH. This indirectly leads to increased anandamide levels, which in turn binds to and activates CB1 leading to subsequent neutral sphingomyelinase activation and breakdown of SM. The neutral sphingomyelinase may be activated via administration of anandamide and via administration of a FAAHi. The neutral sphingomyelinase may be activated via administration 2-AG. The neutral sphingomyelinase may be activated via an administration a compound that inhibits the degradation of 2-AG. The neutral sphingomyelinase may be activated via administration a compound that promotes the production of 2-AG. The neutral sphingomyelinase may be activated via production of 2-AG via activation of a glutamate receptor. The neutral sphingomyelinase may be activated via production of 2-AG via activation of mGluR5. The neutral sphingomyelinase may be activated via production of 2-AG via activation of mGluR5 with its allosteric activator CDPPB.

In some aspects, the present disclosure provides a method of decreasing sphingomyelin (SM) levels in the brain of a subject that has Niemann Pick disease type A (NPA) comprising, activating neutral sphingomyelinase. The neutral sphingomyelinase may be activated with a FAAHi. The FAAHi may be PF-04457845. The method may comprise administering more than one FAAHi inhibitor.

In some aspects, the present disclosure provides a method of decreasing sphingomyelin (SM) levels in the brain of a subject that has Niemann Pick disease type C (NPC) comprising, activating neutral sphingomyelinase. The neutral sphingomyelinase may be activated with a FAAHi. The FAAHi may be PF-04457845. The method may comprise administering more than one FAAHi inhibitor.

In some aspects, the present disclosure provides a method of decreasing sphingomyelin (SM) levels in the brain of a subject that has MPS IIIA comprising, activating neutral sphingomyelinase. The neutral sphingomyelinase may be activated with a FAAHi. The FAAHi may be PF-04457845. The method may comprise administering more than one FAAHi inhibitor.

In some aspects, the present disclosure provides a method of decreasing sphingomyelin (SM) levels in the brain of a subject that has Niemann Pick disease type A (NPA) comprising, activating the CB1 cannabinoid receptor. CB1 may be activated with a FAAHi. The FAAHi may be PF-04457845. The method may comprise administering more than one FAAHi inhibitor. CB1 may be activated with an endocannabinoid. CB1 may be activated with anandamide. CB1 may be activated with 2-AG. CB1 may be activated with an mGluR5 agonist. CB1 may be activated with CDPPB.

In some aspects, the present disclosure provides a method of decreasing sphingomyelin (SM) levels in the brain of a subject that has Niemann Pick disease type C (NPC) comprising, activating the CB1 cannabinoid receptor. CB1 may be activated with a FAAHi. The FAAHi may be PF-04457845. The method may comprise administering more than one FAAHi inhibitor.

In some aspects, the present disclosure provides a method of decreasing sphingomyelin (SM) levels in the brain of a subject that has MPS IIIA comprising, activating the CB1 cannabinoid receptor. CB1 may be activated with a FAAHi. The FAAHi may be PF-04457845. The method may comprise administering more than one FAAHi inhibitor.

In some embodiments, any one of the methods disclosed herein may optionally also comprise administering to the subject an additional therapeutic agent in combination with the FAAHi. Such combination therapies may include, e.g., any additional therapeutic agent known or expected to be useful in treating one or more symptom or underlying cause of ASMD. The combination of the FAAHi and the additional agent may result in additive treatment of ASMD. The combination of the FAAHi and the additional agent may result in synergistic treatment of ASMD.

Suitable combinations include, without limitation a FAAHi and an additional agent or therapy selected from an ASM replacement therapy (including, e.g., recombinant ASM); a glucocorticoid; an inhibitor of histone deacetylase; and a chaperone therapy. Suitable combinations include, without limitation a FAAHi and an HSP70 inhibitor (e.g., arimoclomol). Suitable combinations include, without limitation a FAAHi and an inhibitor of ceramide production.

In some aspects, the additional agent that is administered to the subject in combination with the FAAHi may be, e.g., an ASM replacement therapy. The ASM replacement therapy that may be used in combination with the FAAHi inhibitor may comprise administration of a recombinant ASM to the subject. The ASM may be delivered in any suitable form. For example, in some non-limiting aspects, the ASM is delivered to the subject in the form of a purified protein. Thus, the ASM replacement therapy may comprise, e.g., administration of IV infused recombinant ASM (olidupdase alfa), administration of intrathecally delivered recombinant ASM, administration of intraventricular delivered recombinant ASM, etc., wherein the recombinant ASM may in some aspects be purified. In some aspects, such recombinant ASM may be delivered to the subject as a composition. The composition may be a pharmaceutically acceptable composition. Such pharmaceutically acceptable compositions are known in the art and are disclosed herein. In some aspects, the composition comprising the recombinant ASM is substantially free of endotoxin. In some aspects, the composition comprising the recombinant ASM further comprises one or more carrier, excipient, diluent, and/or surfactant. The recombinant ASM and the FAAHi may be administered to the patient simultaneously or separately. The FAAHi and the recombinant ASM may be formulated together in a single pharmaceutical composition or they may be formulated separately in different formulations. When formulated separately, the FAAHi may be administered before or after the recombinant ASM.

In some non-limiting aspects, the delivery of the ASM to the subject may be by administering an autologous cell expressing a gene encoding a functional ASM enzyme to the subject. The autologous cell may be a hematopoietic stem cell. The autologous hematopoietic stem cell may be genetically engineered to express a gene encoding the functional ASM enzyme. The gene encoding the functional ASM enzyme may be introduced into the autologous cell via viral infection. Any suitable viral packaging may be utilized in delivering the enzyme to the desired tissue. For example, the viral infection may be mediated by a recombinant retrovirus, a recombinant lentivirus, or a recombinant adeno-associated virus (AAV). The AAV may be of any suitable serotype. Those of average skill in the art will appreciate that different serotypes of AAV vectors may be more suitable for delivery to different tissues. For example, AAV9 serotype AAV vectors may be suitable for delivery of an ASM enzyme by means of, a cerebellomedullary cistern injection. Other AAV serotypes may also be used.

In some non-limiting aspects, the delivery of the ASM to the subject may be by administering a recombinant virus to the subject, wherein infection with the virus causes the infected cell to express a gene encoding a functional ASM enzyme. The administering of the recombinant virus may be via any suitable means. For example, the administration of the virus may be by direct injection of the recombinant virus into subject. For instance, the virus may be injected into the subject's brain. The virus may be injected into a ventricle of the subject. The virus may be administered to the subject via a route of administration selected from intravenous infusion, intrathecal infusion, and intraventricular injection.

In some aspects, the additional agent that is administered to the subject in combination with the FAAHi may be, e.g., a glucocorticoid. The glucocorticoid may be dexamethasone. The glucocorticoid may be hydrocortisone.

The glucocorticoid may be delivered in any suitable form. For example, the glucocorticoid may be delivered to the subject as a composition. The composition may be a pharmaceutically acceptable composition. Such pharmaceutically acceptable compositions are known in the art and are disclosed herein. In some aspects, the composition comprising the glucocorticoid is substantially free of endotoxin. In some aspects, the composition comprising the glucocorticoid further comprises one or more carrier, excipient, diluent, and/or surfactant. The glucocorticoid and the FAAHi may be administered to the patient simultaneously or separately. The FAAHi and the glucocorticoid may be formulated together in a single pharmaceutical composition or they may be formulated separately in different formulations. When formulated separately, the FAAHi may be administered before or after glucocorticoid.

In some aspects, the additional agent that is administered to the subject in combination with the FAAHi may be, e.g., an inhibitor of histone deacetylase. In some aspects, the additional agent that is administered to the subject in combination with the FAAHi may be, e.g., an agent that enhances plasma membrane calcium ATPase (PMCA) expression. The additional agent that is administered to the subject in combination with the FAAHi may be, e.g., the histone deacetylase inhibitor SAHA (Suberoylanilide hydroxamic acid). The histone deacetylase inhibitor (e.g., SAHA) may be delivered in any suitable form. For example, the histone deacetylase inhibitor (e.g., SAHA) may be delivered to the subject as a composition. The composition may be a pharmaceutically acceptable composition. Such pharmaceutically acceptable compositions are known in the art and are disclosed herein. In some aspects, the composition comprising the histone deacetylase inhibitor (e.g., SAHA) is substantially free of endotoxin. In some aspects, the composition comprising the histone deacetylase inhibitor (e.g., SAHA) further comprises one or more carrier, excipient, diluent, and/or surfactant. The histone deacetylase inhibitor (e.g., SAHA) and the FAAHi may be administered to the patient simultaneously or separately. The FAAHi and the histone deacetylase inhibitor (e.g., SAHA) may be formulated together in a single pharmaceutical composition or they may be formulated separately in different formulations. When formulated separately, the FAAHi may be administered before or after the histone deacetylase inhibitor (e.g., SAHA).

The FAAHi may be administered in combination with a chaperone therapy. The chaperone therapy may be an inhibitor of α-GalA. The chaperone therapy may be Miglustat. The FAAHi may be administered in combination with a small molecule inhibitor that is useful in treating a lysosomal storage disorder. Thus, the FAAHi may be administered, e.g., in combination with a substrate reduction therapy. The substrate reduction therapy may inhibit ganglioside production. The additional agent may be an inhibitor of sphingomyelin production. The additional agent may be an inhibitor of sphingomyelin synthase. The additional agent may be an inhibitor of glucosylceramide synthase. The additional agent may be a ceramide analogue. The additional agent may be miglustat. The additional agent may be eliglustat. The substrate reduction therapy may be zavesca or Cerdelga.

The chaperone therapy may be delivered in any suitable form. For example, the chaperone therapy may be delivered to the subject as a composition. The composition may be a pharmaceutically acceptable composition. Such pharmaceutically acceptable compositions are known in the art and are disclosed herein. In some aspects, the composition comprising the chaperone therapy is substantially free of endotoxin. In some aspects, the composition comprising the chaperone therapy further comprises one or more carrier, excipient, diluent, and/or surfactant. The chaperone therapy and the FAAHi may be administered to the patient simultaneously or separately. The FAAHi and the chaperone therapy may be formulated together in a single pharmaceutical composition or they may be formulated separately in different formulations. When formulated separately, the FAAHi may be administered before or after the chaperone therapy.

The FAAHi may be administered in combination with an additional agent that induces reduction of high levels of sphingomyelin, sphingosine and gangliosides GM2 and GM3. The FAAHi may be administered in combination with an inhibitor of ceramide. The FAAHi may be administered in combination with an additional agent that induces reduction of high levels of cytosolic calcium in neurons. The FAAHi may be administered in combination with an additional agent that induces reduction of oxidative stress. The FAAHi may be administered in combination with an additional agent that induces enhancement of glucocorticoid signaling (e.g., an agent that enhances expression of glucocorticoid receptors or increases glucocorticoid levels). The FAAHi may be administered in combination with an additional agent that induces reduction of inflammation with two main objectives: Reduction of pro-inflammatory microglia (M1 type) and/or the secretion of pro-inflammatory cytokines or enhancement of phagocytic microglia (M2 type).

The FAAHi may also be administered in combination with an additional agent that induces increases in 2-AG levels. The agent that increases 2-AG levels may be an agonist of mGluR5. The agent that increases 2-AG levels may be CDPPB. In in some embodiments, a combination therapy comprises administering to a subject (i) a FAAHi and (ii) an agent that increases 2-AG (e.g., CDPPB), wherein one or both of the FAAHi and the agent that increases 2-AG (e.g., CDPPB) are administered at a concentration that is less than the optimal dose that would be needed to inducing maximal efficacy as a single agent therapy. In some embodiments, the combination of the FAAHi and the agent that induces 2-AG (e.g., CDPPB) act together synergistically to decrease sphingomyelin levels in the subject. In some embodiments, the sphingomyelin is synergistically decreases in a neuron of the subject.

Moreover, in some embodiments, any one of the combination therapies disclosed herein (i.e., the FAAHi and the additional agent) may comprise a second, third, fourth additional agent, or more than four additional agents. Optionally, the additional agent or agents may comprise a second FAAHi inhibitor. Alternatively, the additional agent or agents may comprise an agent other than a second FAAHi inhibitor (e.g., an agent that increases 2-AG levels).

In some aspects, the present disclosure provides a combination therapy for treating a lipid storage disorder comprising a first agent that is a FAAHi and a second agent. The second agent may be an agent that is expected or known to be useful in treating the lipid storage disorder. The FAAHi may be any FAAHi disclosed herein. The FAAHi may be PF-04457845. The additional agent may be selected from an Enzyme Replacement Therapy (ERT), a gene therapy, a substrate reduction/substrate inhibition; a small molecule; a chaperone, and an enzyme activator. The additional agent may be any additional agent disclosed herein.

Administration of the disclosed compositions and compounds (e.g., FAAHi inhibitors and/or other therapeutic agents) can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compounds or pharmaceutical compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Pharmaceutical compositions suitable for the delivery of a FAAHi inhibitor (alone or, e.g., in combination with another therapeutic agent according to the present disclosure) and methods for their preparation will be readily apparent to those skilled in the art. Such compositions and methods for their preparation may be found, e.g., in Remington's Pharmaceutical Sciences, 19th Edition (Mack Publishing Company, 1995), incorporated herein in its entirety.

Illustrative pharmaceutical compositions are tablets and gelatin capsules comprising a FAAHi inhibitor alone or in combination with another therapeutic agent according to the disclosure and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algiic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, a FAAHi inhibitor (alone or in combination with another therapeutic agent according to the disclosure) is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the FAAHi inhibitor (alone or in combination with another therapeutic agent according to the disclosure).

The FAAHi inhibitor (or an additional agent utilized in a combination therapy) can be also formulated as a suppository, alone or in combination with another therapeutic agent according to the disclosure, which can be prepared from fatty emulsions or suspensions; using polyalkylene glycols such as propylene glycol, as the carrier.

The FAAHi inhibitor (or an additional agent utilized in a combination therapy) can also be administered in the form of liposome delivery systems, such as small unilamellar vesicles, large unilamellar vesicles and multilamellar vesicles, either alone or in combination with another therapeutic agent according to the disclosure. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described for instance in U.S. Pat. No. 5,262,564, the contents of which are hereby incorporated by reference.

FAAHi inhibitors can also be delivered by the use of monoclonal antibodies as individual carriers to which the disclosed compounds are coupled. FAAHi inhibitors can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, a FAAHi inhibitor can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the invention relates to a pharmaceutical composition comprising a FAAHi inhibitor (alone or in combination with another therapeutic agent according to the present disclosure) and a pharmaceutically acceptable carrier. The pharmaceutically acceptable carrier can further include an excipient, diluent, or surfactant.

The FAAHi inhibitor utilized in the compositions and methods disclosed herein need not be a single FAAHi (although as is clearly set forth above, the FAAHi inhibitor may be a single FAAHi). Instead, compositions and methods may comprise one or more FAAHi and, optionally, an additional agent for use in a combination therapy disclosed herein.

Thus, the present disclosure provides compositions (e.g., pharmaceutical compositions) comprising one or more FAAHi inhibitor for use in a method disclosed herein, e.g., a FAAHi monotherapy or a FAAHi combination therapy. Such compositions may comprise a FAAHi inhibitor and, e.g., one or more carrier, excipient, diluent, and/or surfactant.

The present disclosure provides compositions (e.g., pharmaceutical compositions) comprising one or more CB1 activator for use in a method disclosed herein, e.g., a CB1 agonist monotherapy or a CB1 agonist combination therapy. Such compositions may comprise a CB1 agonist and, e.g., one or more carrier, excipient, diluent, and/or surfactant.

The present disclosure provides compositions (e.g., pharmaceutical compositions) comprising one or more mGluR5 activator for use in a method disclosed herein, e.g., a mGluR5 agonist monotherapy or a mGluR5 agonist combination therapy. The mGluR5 agonist may be CDPPB Such compositions may comprise a mGluR5 agonist (e.g., CDPPB) and, e.g., one or more carrier, excipient, diluent, and/or surfactant.

The FAAHi (e.g., PF-04457845) may be administered to the subject as a pharmaceutical composition.

The CB1 activator (e.g., PF-04457845, anandamide, 2-AG, CDPPB) may be administered to the subject as a pharmaceutical composition.

In order to fully illustrate the present invention and advantages thereof, the following specific examples are given, it being understood that the same are intended only as illustrative and in no way limitative.

EXAMPLES

Example 1

Alterations of the Endocannabinoid Receptor CB1 in the Brain and in Cultured Neurons from Acid Sphingomyelinase Knock Out Mice (Asmko), a Model for NPA Background ASMD is caused by loss of function mutations in the (SMPD1) encoding acid sphingomyelinase (ASM). A knockout mouse lacking the ASM gene has been previously generated and validated as a model for Niemann Pick disease type A (NPA). This mouse is referred to herein as an "ASMko" mouse. The ASMko mice we utilized in the following studies were in the C57BSL/6 strain, and in all experiments, mice were fed regular diet and provided water ad libitum from lixits. Samples of water were routinely analyzed for specified microorganisms and environmental contaminants. Environmental controls for the animal room were maintained at 22±2° C., a relative humidity of 55±10%, a minimum of 10-12 air changes/hour, and a 12-hour light/12-hour dark cycle.

Methods

We analyzed mRNA and protein expression of the CB1 cannabinoid receptor in the brains of ASMko mice via qPCR and immunofluorescence, respectively. CB1 protein levels were also analyzed in cultured primary hippocampal neurons.

Briefly, mice were sacrificed and, following termination, they were transcardially perfused with phosphate-buffered saline (PBS). Brains were harvested and divided sagittaly in two hemispheres. Right hemisphere was blocked coronally in 2 mm blocks, snaps frozen by immersion in ice-cold isopentane and stored at −80° C. for posterior biochemical analysis. Left hemisphere was post-fixed by immersion in 4% paraformaldehyde/PBS overnight and then transferred to 30% (w/v) sucrose. Brains were coronally sectioned at 40 μm by slicing microtome and stored in antifreeze solution at +4° C. for posterior histological analysis.

Results

Reduction of the Levels of CB1 mRNA in the Brain of ASMko Mice.

We measured the mRNA levels of CB1 by qPCR in extracts of cerebellum, hippocampus and cortex of wt and ASMko mice at 4 months of age. We found significant reductions in all brain areas (24%, 40% and 29%, respectively) in the ASMko compared to the wt mice (FIG. 1).

Reduction of the Levels of CB1 Protein in the Brain of ASMko Mice

Figure 2:
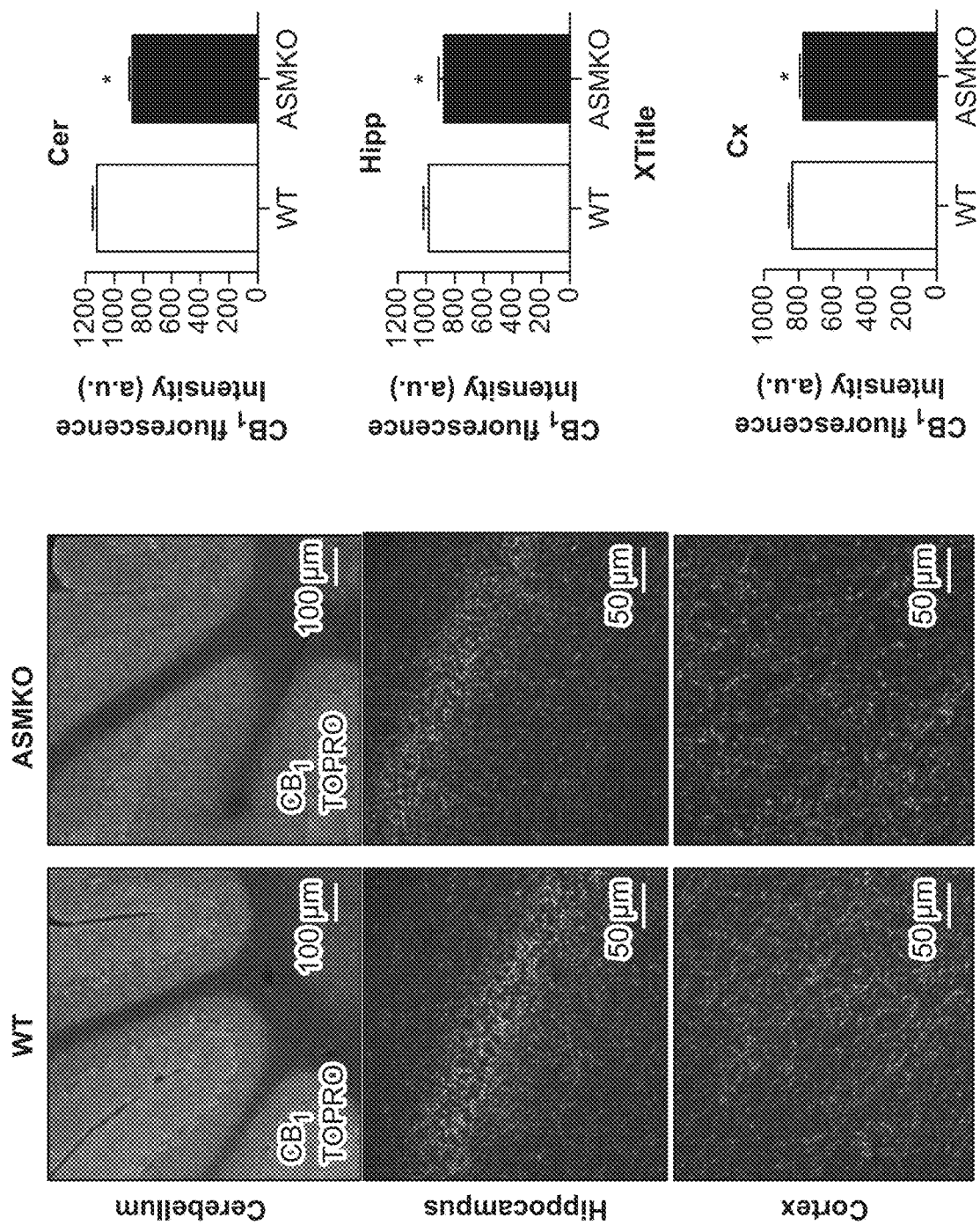
FIG. 2 shows representative images of CB1 protein staining in the cerebellum, hippocampus and cortex of wt and ASMko mice. Topro in blue shows cell nuclei. Graphs show mean±SEM intensity associated to CB1 (n=5, *p<0.05).

We measured the protein levels of CB1 by immunofluorescence in the cerebellum, hippocampus and cortex of wt and ASMko mice at 4 months of age. Although the reductions were smaller in protein than in mRNA levels they were statistically significant in all brain areas (22%, 10% and 8%, respectively) in the ASMko compared to the wt mice (FIG. 2).

Reduction of the Levels of CB1 Protein in Cultured Hippocampal Neurons from ASMko Mice.

Figure 3:
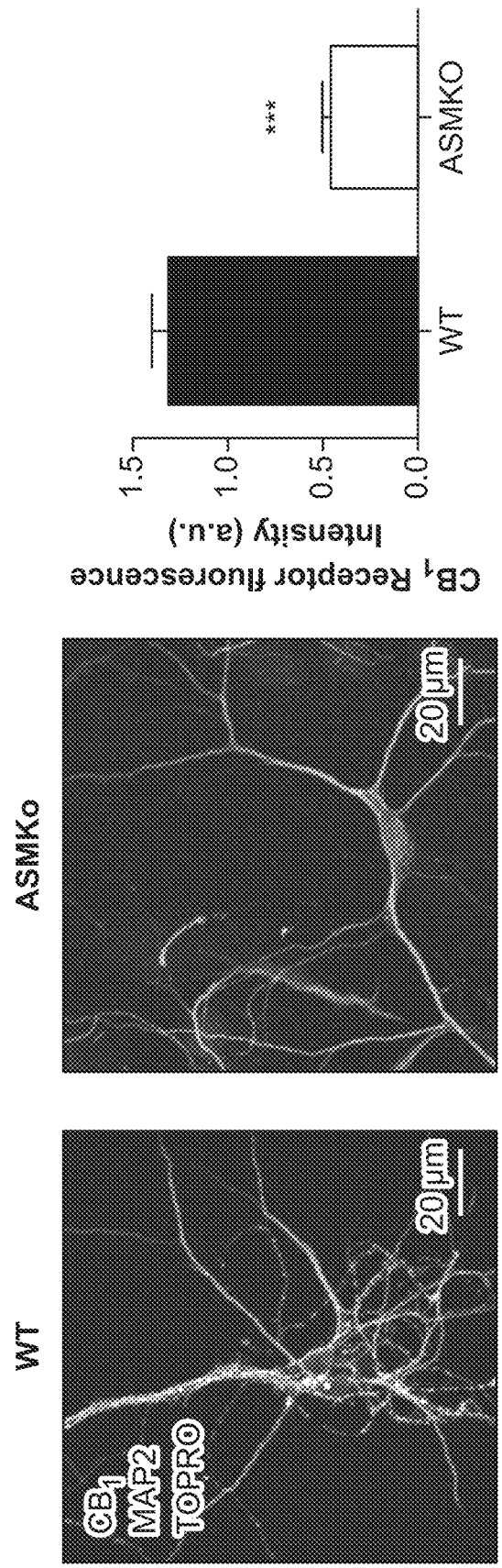
FIG. 3 shows representative images of CB1 protein staining in cultured primary hippocampal neurons from wt and ASMko mice. MAP2 staining in red shows dendrites. Topro in blue shows cell nuclei. Graphs show mean±SEM intensity associated to CB1 (n=30 cells from 3 independent cultures, ***p<0.001).

We measured protein levels of CB1 by immunofluorescence in cultured primary hippocampal neurons from wt and ASMko mice at 14 days in vitro (DIV), when these cells are fully mature. We observed a remarkable reduction of CB1 protein levels (65%) in ASMko neurons compared to wt especially evident in the axons (FIG. 3).

Conclusions

Both mRNA and protein levels of the endocannabinoid receptor CB1 are reduced in different areas of ASMko brains. CB1 protein levels are also reduced in ASMko cultured hippocampal neurons especially in the axons.

Example 2

High Levels of Sm Reduce CB1 Protein in Cultured Hippocampal Neurons

We hypothesized that high sphingomyelin levels in the ASMko mice may induce CB1 protein reduction in neurons. We therefore confirmed this hypothesis by incubating 14 DIV primary cultured neurons from wt mice with different doses of sphingomyelin (20 μM and 40 μM) for 24 hours.

Figure 4:
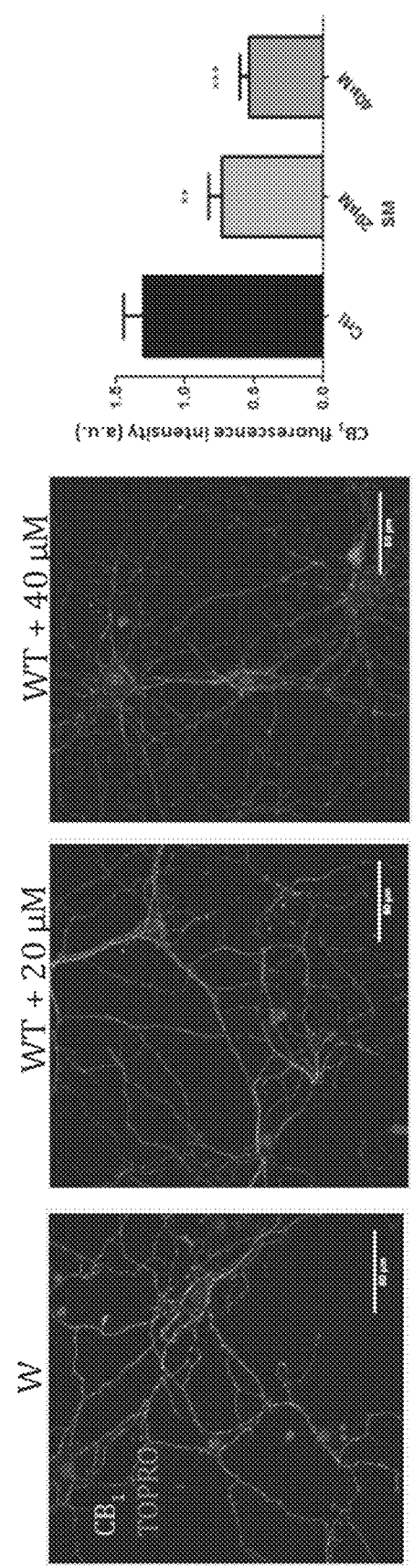
FIG. 4 shows representative images of CB1 protein staining in cultured primary hippocampal neurons from wt mice treated or not with the indicated concentrations of sphingomyelin. Topro in blue shows cell nuclei. Graphs show mean±SEM intensity associated to CB1 (n=30 cells from 3 independent cultures, p<0.005, *p<0.001)

As shown in FIG. 4, CB1 protein levels were reduced by the lipid in a dose dependent manner (44% and 60%, respectively, with respect to non-treated neurons).
Conclusions High levels of sphingomyelin induce CB1 protein reduction.

Example 3

Activation of CB1 Reduces Sphingomyelin Levels

The high sphingomyelin-induced reduction of CB1 suggests that the endocannabinoid system is downregulated in ASMD, and especially prominent in the most severe neurovisceral forms of ASMD. This could underlie alterations in physiological processes such as cognition, response to stress, and body temperature control in which this system is critically involved.

Accordingly, we posited that pharmacological enhancement of the endocannabinoid system might be a suitable therapeutic strategy not only for NPA, but also for other lysosomal storage disorders in which sphingomyelin accumulates. Activation of CB1 would not only restore the normal activity of the endocannabinoid system but might also contribute to reduce sphingomyelin levels, as CB1 activation with exogenous tetrahydrocannabinol or endogenous anandamide has been reported to activate neutral sphingomyelinase (although the authors saw their result in primary astrocytes alone, and not in other cells including not in neurons) (Sanchez et al., Mol Pharmacol 2001), and this gene (SMPD2) is not mutated in ASMD. In these cells, cannabinoids mediate the activity-induced coupling of CB1 to the adaptor protein FAN, which in turn activates the neutral sphingomyelinase (Sanchez et al., Mol Pharmacol 2001, 59: 955-959).

Anandamide (AEA) is the major endogenous CB1 ligand. We therefore tested whether increased levels of anandamide affected sphingomyelin levels in cultured primary hippocampal neurons from ASMko mice. Anandamide was increased in two ways:

1. By incubating the neuronal cultures with exogenous anandamide; and
2. By incubating the neuronal cultures with PF-04457845, which is an inhibitor of the anandamide hydrolytic enzyme FAAH. Inhibition of FAAH causes accumulation of anandamide by inhibiting FAAH-mediated hydrolyzation of anandamide.

As shown in FIG. 5A, treatment of cultured primary hippocampal neurons from ASMko mice with either one of anandamide and PF-04457845 resulted in reduced sphingomyelin levels. Moreover, these effects were prevented by co-incubation with the neutral sphingomyelinase inhibitor GW4869, demonstrating that this decrease in sphingomyelin was mediated by increased hydrolysis by neutral sphingomyelinase.

We investigated whether any changes in the basal levels of anandamide were evident in the hippocampus of ASMko mice as compared to wt mice and found no significant differences (FIG. 5B). However, interestingly, hippocampal levels of the endocannabinoid 2-Arachidonoylglycerol (2-AG) were significantly decreased in the ASMko mice as compared to wt mice (FIG. 5C). Although 2-AG is the primary endogenous ligand for the CB2 receptor, it also acts as a CB1 agonist. We therefore posited that restoration of 2-AG levels might also result in reduction in sphingomyelin levels.

It has been shown that mGluR activation promotes 2-AG synthesis and CB1 stimulation (Maccarrone et al., Nat Neurosci 2008). We therefore sought to determine whether activation of mGluR5 with the allosteric activator CDPPB might induce sphingomyelin breakdown in ASMko neurons. Indeed, treatment of ASMko cultured neurons with CDPPB resulted in significant decreases in sphingomyelin levels, but CDPPB did not affect sphingomyelin levels in wildtype mice (FIG. 5D). Thus, the effect of decreased CB1 expression might be further exacerbated by decrease in endogenous endocannabinoid signaling, at least via 2-AG.
Conclusions Activation of CB1 increases neutral sphingomyelinase in neurons from ASMko mice, and this in turn leads to a reduction of neuronal sphingomyelin levels. Thus, CB1 agonism presents a viable target for treating or preventing the various forms of ASMD, including not only the mild NPB type and other non-neurovisceral intermediate forms of the disease, but also the severe neurovisceral form, NPA.

Example 4

Optimization of CB1-Mediated Sphingomyelin Reduction

Figure 6:
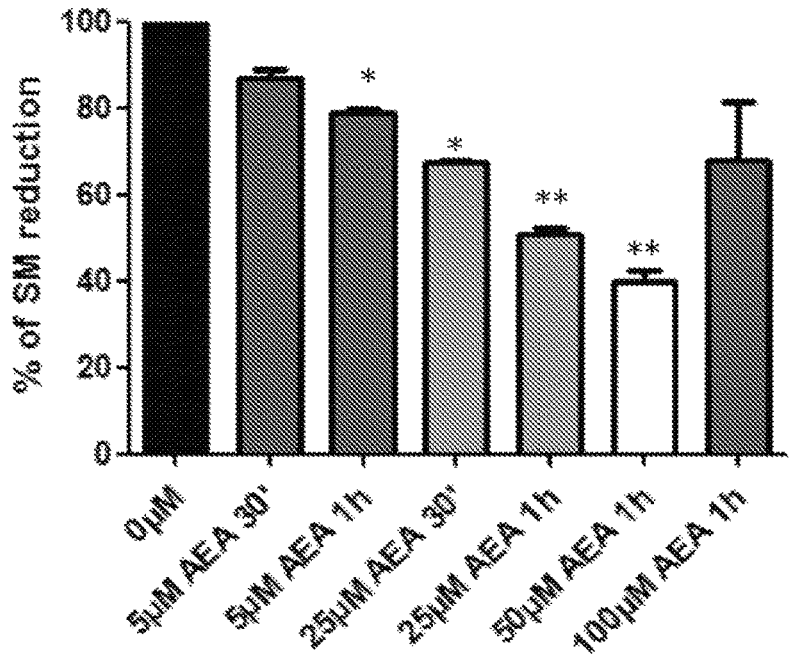
FIG. 6 shows anandamide promotes SM hydrolysis in a time and dose dependent manner. The graph shows the mean (±SEM) of SM levels measured by enzymatic assays in nmol/mg protein and expressed as percentage with respect to the non-treated ASMko neuronal cultures (anandamide: AEA). Statistical significance Student's t-test, *P<0.05, **P<0.005, n=3 independent cultures.
Figure 7:
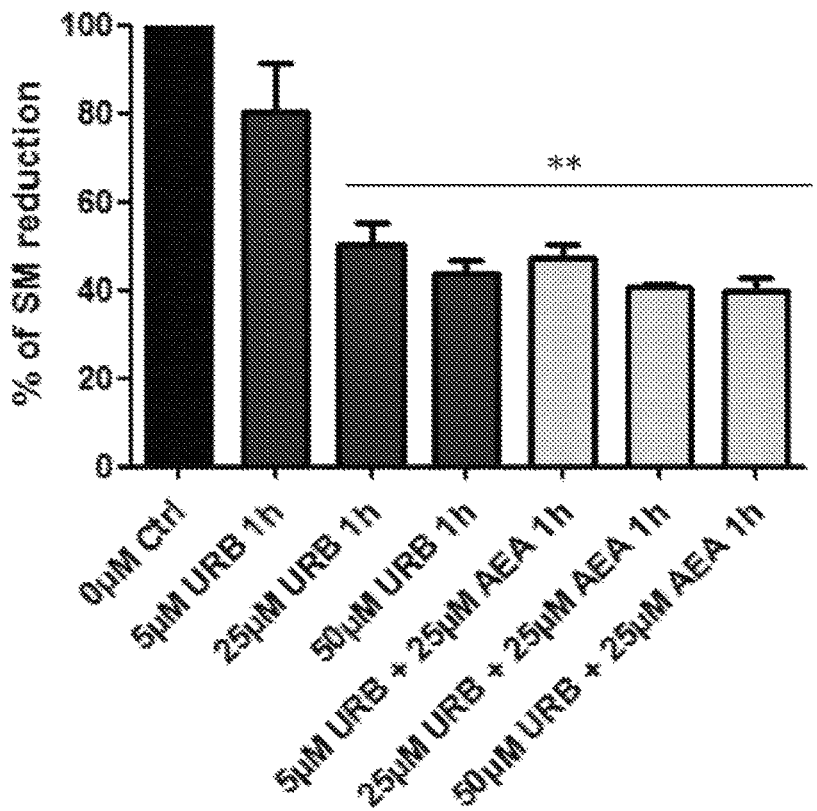
FIG. 7 shows URB597 (URB) promotes SM hydrolysis in the presence or absence of exogenous anandamide. The graph shows the mean (±SEM) of SM levels measured by enzymatic assays in nmol/mg protein and expressed as percentage with respect to the non-treated ASMko neuronal cultures (anandamide: AEA). Statistical significance Student's t-test, **P<0.005, n=3 independent cultures.

Culturing Primary Hippocampal Neurons:

The following experiments were performed in three independent cultures of hippocampal neurons derived from ASMko mice. Treatments were done at 11-13 days in vitro when these cells are considered mature and functional.
Anandamide Effects on SM Hydrolysis in ASMko Cultured Neurons:

To set the optimal conditions for such hydrolysis in terms of concentration and time of incubation, anandamide was added to the culture medium of mature ASMko hippocampal neurons at 0, 5, 25, 50 and 100 µM for 30 minutes or 1 hour. As shown in FIG. 6, anandamide induced SM hydrolysis in a dose and time dependent manner. The optimal conditions for SM degradation were in a range of concentration of 25-50 µM for 1 hour. However, at a very high anandamide concentration, 100 µM, SM reduction was prevented. We therefore decided to use 25 µM anandamide for 1-hour incubation time in our next experiments.
Effects of FAAH Inhibitors on SM Hydrolysis in ASMko Cultured Neurons:

Similar to the anandamide dose/time response experiment above, we performed another dose response experiment using URB597 (URB), an inhibitor of the anandamide-hydrolyzing enzyme FAAH, to be used as reference for the other FAAH inhibitors. The experiments were done in the presence or absence of exogenous anandamide. URB was added to the culture medium of ASMko mature neurons at 0, 5, 25 and 50 µM for 1 hour with or without □□µM anandamide. The results, shown in FIG. 7, demonstrated that URB itself was able to induce a dose dependent reduction of SM levels indicating that most probably endogenous amounts of anandamide are present in the cultures. Except for the lowest URB concentration of □ µM, in which anandamide addition synergized the action of URB, SM reduction was similar in the treatments with URB alone or with URB and anandamide.

Figure 8:
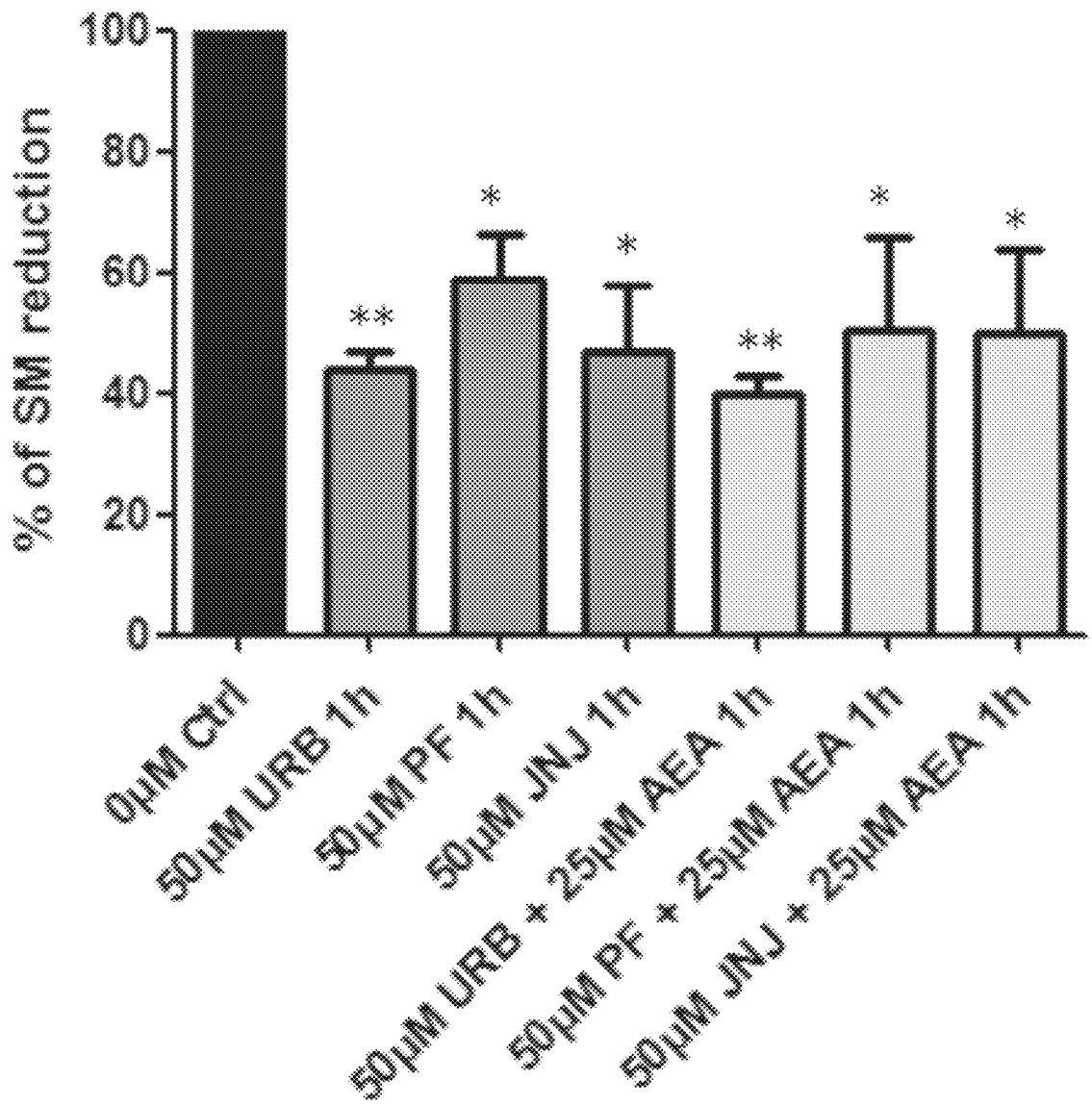
FIG. 8 shows URB597, PF-04457845 and JNJ-1661010 promote SM hydrolysis with a similar efficiency in the presence or absence of exogenous anandamide. The graph shows the mean (±SEM) of SM levels measured by enzymatic assays in nmol/mg protein and expressed as percentage with respect to the non-treated ASMko neuronal cultures (anandamide: AEA). Statistical significance Student's t-test, *P<0.05, **P<0.005, n=3 independent cultures.

We next compared URB efficacy to reduce SM levels with that of other FAAH inhibitors PF-04457845 (PF) and JNJ-1661010 (JNJ). These results are presented in FIG. 8, and they showed that while all the tested FAAH inhibitors promoted SM hydrolysis the most reliable and efficient was URB at least in the concentration and time analyzed (50 µM and 1 hour). In these conditions, the addition of exogenous anandamide did not further enhance SM hydrolysis.

Figure 9:
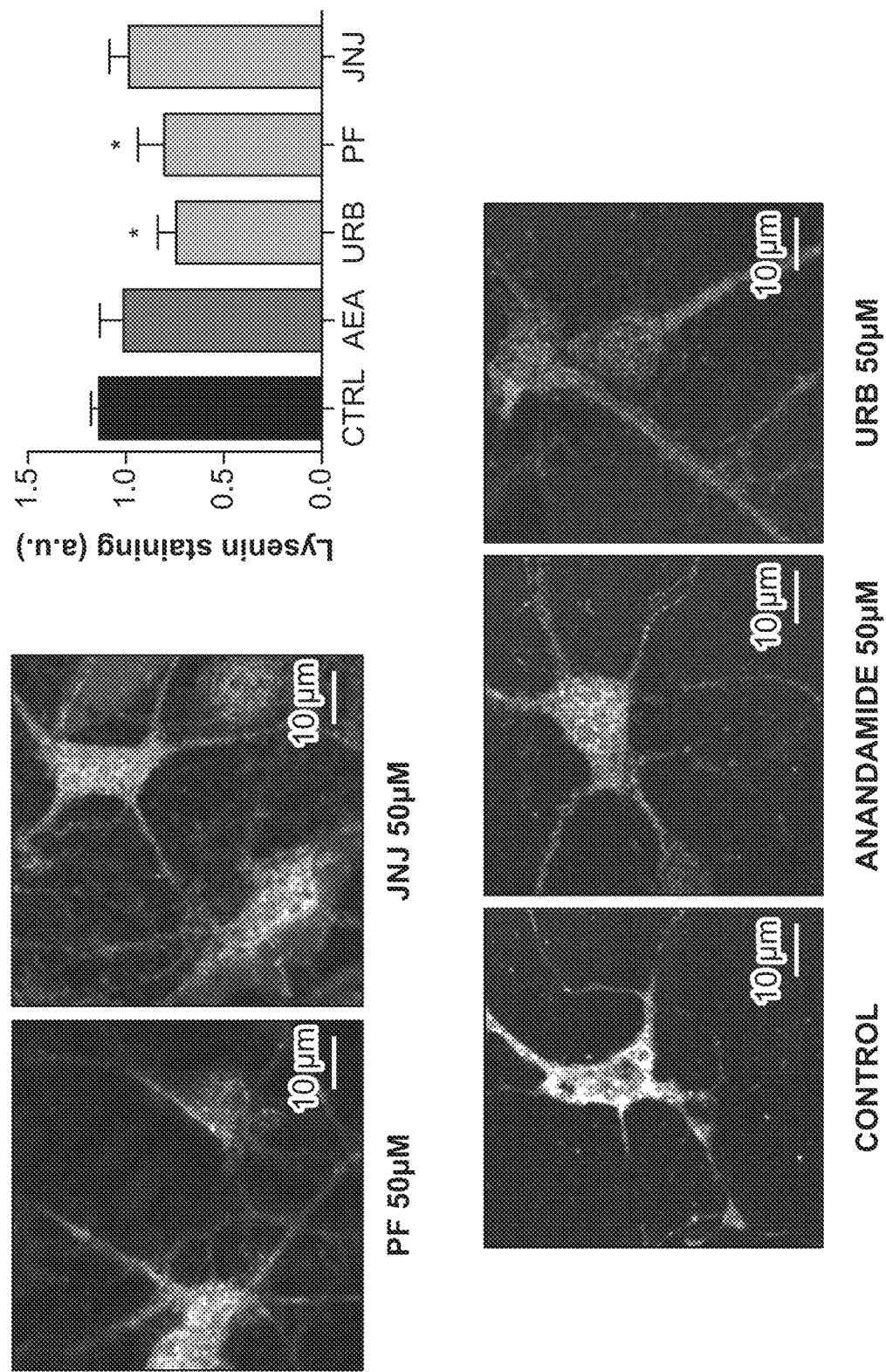
FIG. 9 shows FAAH inhibitors promote SM reduction in intracellular compartments of ASMko cultured neurons at different extent. The figure shows representative immunofluorescence images using an antibody against lysenin in permeabilized ASMko neurons non treated (control) or treated with anandamide, URB, PF-04457845 and JNJ-1661010 for 1 hour at 50 µM. The graph shows the mean (±SEM) of the intensity of lysenin staining per area unit expressed in arbitrary units. Statistical significance Student's t-test, *P<0.05, n=3 independent cultures.

To determine whether SM hydrolysis induced by FAAH inhibitors was taking place not only at the cell surface, but also in intracellular compartments, we performed staining with lysenin, a worm toxin that specifically binds to SM, in permeabilized ASMko neurons non-treated or treated with anandamide, URB, PF-04457845 or JNJ for 1 hour at 50 µM. As shown in FIG. 9, while anandamide and JNJ showed a variable tendency to SM reduction that was not statistically significant, PF-04457845 and URB treatments significantly reduced SM levels in intracellular compartments of ASMko neurons.

Influence of FAAH Inhibitors on ASMko Cultured Neuron Viability

Figure 10A:
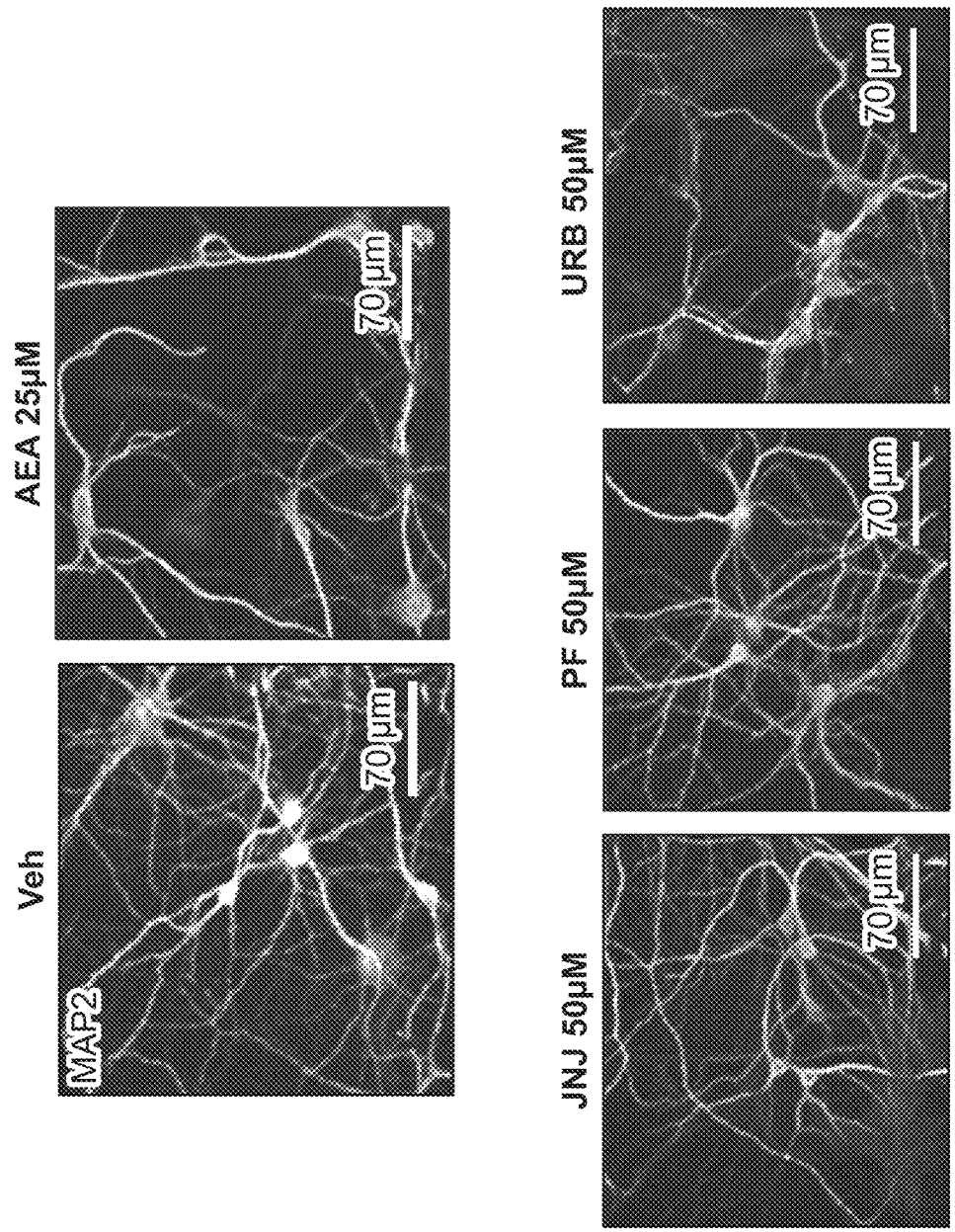
FIG. 10A shows representative immunofluorescence images of ASMko neurons obtained using an antibody against the dendritic marker MAP2.
Figure 10B:
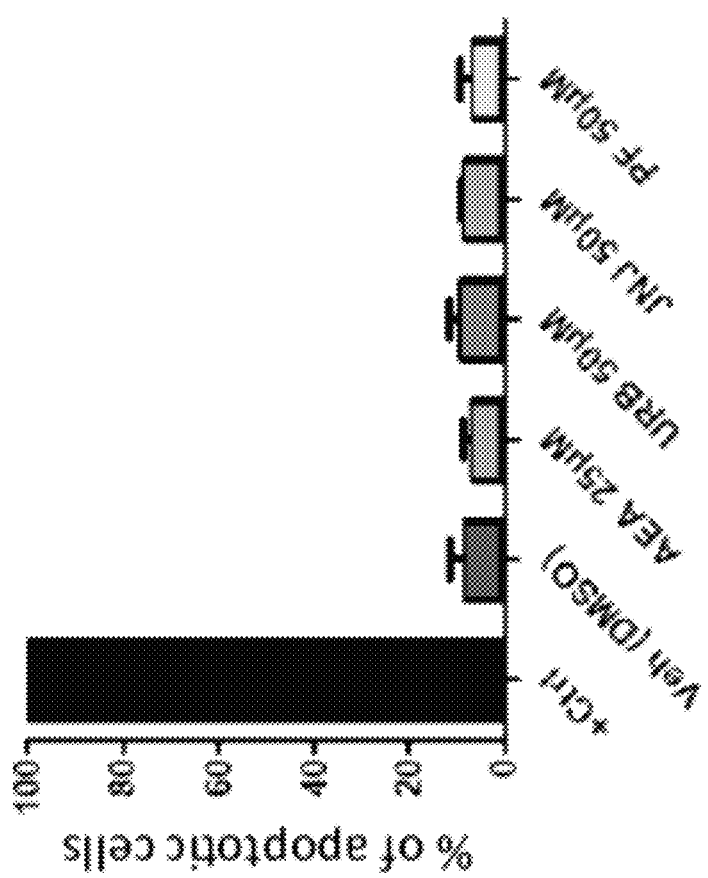
FIG. 10B is a graph showing mean±SEM percentage of apoptotic cells, measured by TUNEL assay, with respect to the positive control in which the cells were treated with H2O2.

Treatments with anandamide, URB, PF-04457845 or JNJ at 50 µM for 1 hour did not induce neuronal death as assessed by TUNEL (FIG. 10). The percentage of dying neurons showing DNA fragmentation was 5-8% in the treated ASMko cultures similar to the non-treated ones. Moreover, the treatments did not alter the morphology, length or homogeneous appearance of dendrites, as detected by immunofluorescence with the dendritic marker MAP2, which is indicative of healthy neurons (FIG. 10). Altogether, these results indicate that FAAH inhibitors do not promote neuronal toxicity in the conditions tested.

Conclusions

The endocannabinoid anandamide is able to promote SM hydrolysis in hippocampal neurons. Inhibitors of the anandamide hydrolyzing enzyme FAAH are also able to promote SM hydrolysis, which is synergized with the addition of exogenous anandamide only at low concentrations of FAAH inhibitors. The FAAH inhibitor URB is slightly more efficient in promoting SM hydrolysis in ASMko neurons compared to PF-04457845 and JNJ. URB and PF-04457845 promote significant SM hydrolysis in intracellular compartments of ASMko neurons FAAH inhibitors induce SM hydrolysis without inducing neuronal toxicity as assessed by cell death quantification and by the normal appearance of dendrites In some respects, enhancing the effects of endogenously released cannabinoid ligands in the brain may be a safer and more effective therapeutic approach than administering drugs that act directly at the cannabinoid receptor CB1 (Di Marzo, Pharmacol Res 2009, 60:77-84). Inhibitors of the fatty acid amide hydrolase (FAAHi) prevent the breakdown of endocannabinoids, prolonging and enhancing their effects where and when they are naturally released, in contrast to the global effects of exogenously administered cannabinoids (Panlilio et al., Pharmacol Ther 2013, 138:84-102).

Example 5

Efficacy Assessment of FAAH Inhibitors to Treat Brain Pathology in Acid Sphingomyelinase Knock Out Mice (Asmko)

Given our confirmation that three different FAAHi compounds were able to decrease SM levels-as efficiently as anandamide in primary cultures of ASMko neurons, and without eliciting cellular toxicity, we tested the efficacy of a FAAHi for treating ASMko mice.

In Vivo Efficacy of the FAAHi PF-04457845.

Among the different FAAHi inhibitors analyzed in our in vitro and ex vivo studies, we chose PF-04457845 (Johnson et al., ACS Medicinal Chem Lett 2011, 2:91-96) to conduct a preclinical in vivo study in the ASMko mice because i) we demonstrated its ability to reduce sphingomyelin levels in primary cultures of neurons without promoting toxicity; ii) it can cross the brain blood barrier; iii) it has exceptional selectivity and in vivo efficacy with long duration of action and optimal pharmacokinetic properties in rodents (Ahn et al., J Pharm Exp Ther 2011) and iv) its safety in healthy humans has been already demonstrated (Ling et al., BJCP 2011).

Mice Distribution and Treatment

We divided wt and ASMko into four groups: wt, wt+FAAHi, ASMko, ASMko+FAAHi. Each group included 14 animals with females and males in equal proportions.

Treatment started at 7 weeks of age and continued for 8 weeks. PF-04457845 was dissolved in 0.9% NaCl and delivered through oral gavage at a dose of 0.3 mg/kg every three days. We chose this dose based on the studies published by Ahn et al., (J Pharm Exp Ther 2011). Control groups received same volume of 0.9% NaCl without PF-04457845.

Figure 11:
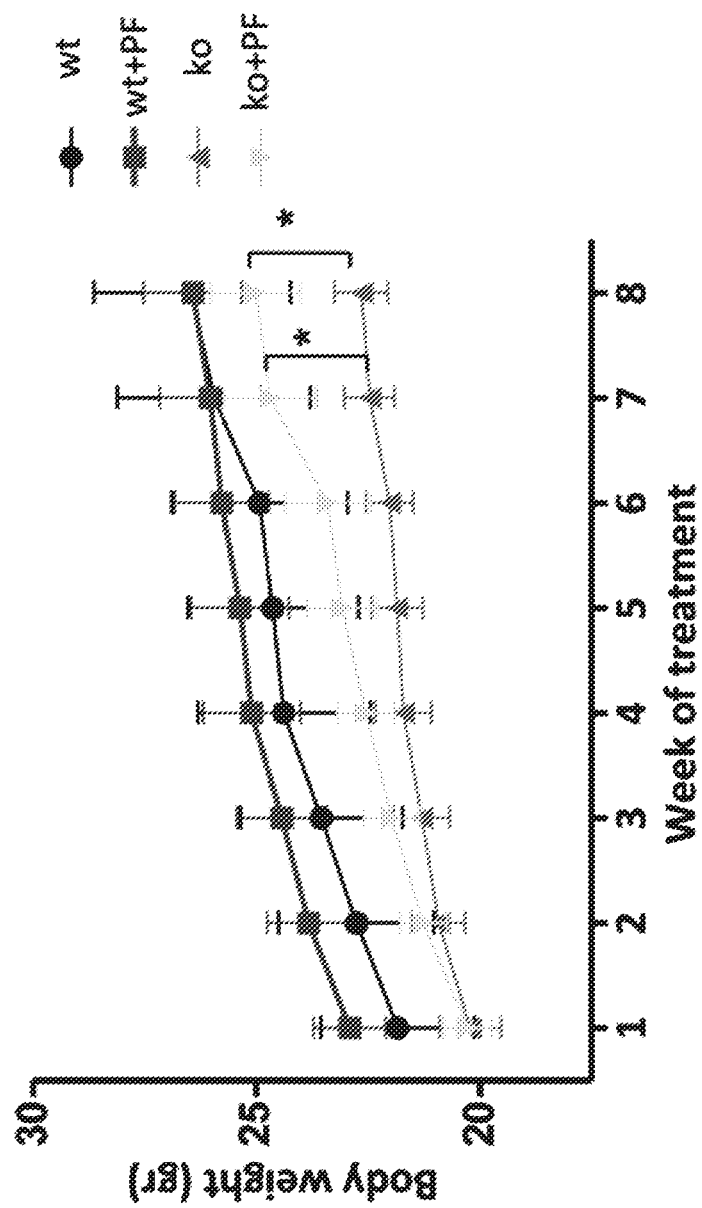
FIG. 11 shows that PF-04457845 treatment improves body weight gain. The graph shows mean±SEM body weight in grams from wt and ASMko mice treated or not with PF-04457845 in each week along the treatment (n=14; *p<0.05).

Behavioral analyses were performed in the last 2 weeks of treatment while still administering the drug. Then, half of the mice were sacrificed for biochemical and histological analysis and the other half continued receiving the treatment to monitor life span. Weekly assessment of body weight throughout the treatment (FIG. 11) showed a continuous weight gain in wt mice that was not affected by PF-04457845 treatment. In contrast, we observed diminished body weight gain in non-treated ASMko that was significantly improved by PF-04457845 treatment (FIG. 11)

Behavioral Analysis

Figure 12:
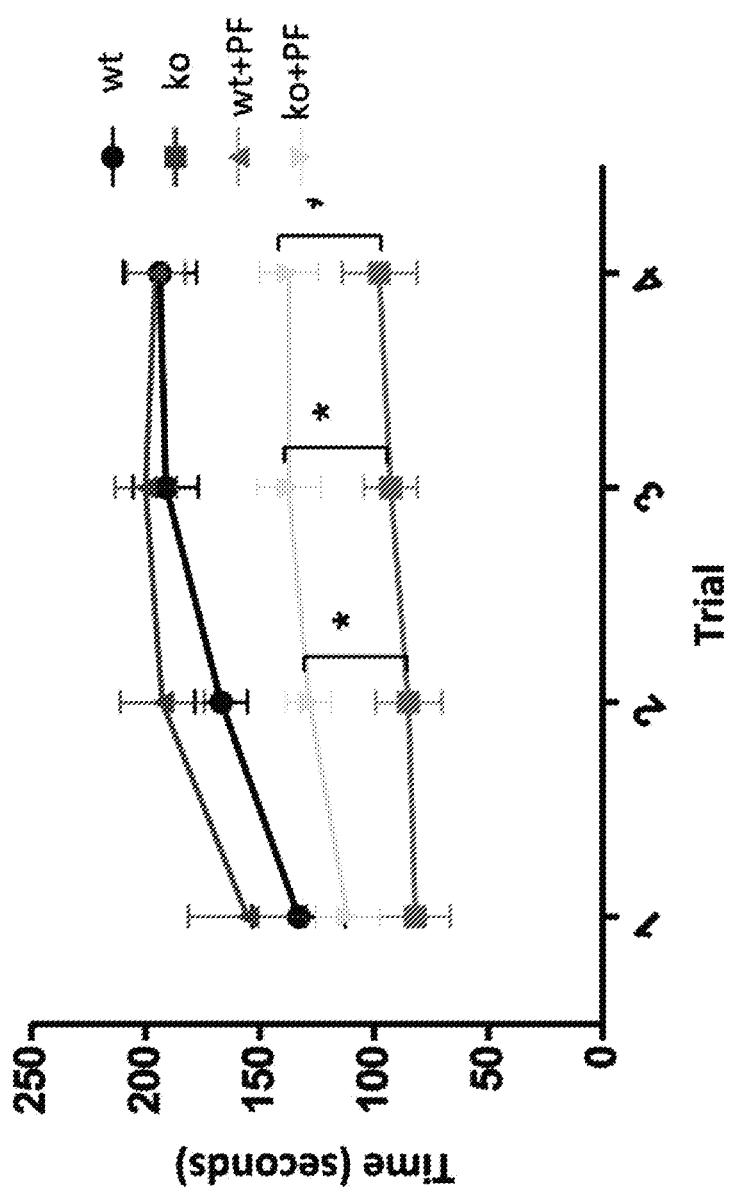
FIG. 12 shows mean±SEM time that wt and ASMko mice treated or not with PF-04457845 spent on the rod in 4 different Rotarod trials (n=14; *p<0.05).

Cerebellar dependent motor abilities were monitored in an accelerating Rotarod (FIG. 12) on which the mice were trained for two days at a constant speed: the first day four times at 4 rpm for 1 min and the second day four times at 8 rpm for 1 min. On the third day, the Rotarod was set to progressively accelerate from 4 to 40 rpm for 5 min and the mice were tested four times. During the accelerating trials, the latency to fall from the rod was measured. Non-treated ASMko mice spent less time on the rod in the four trials than wt mice, indicative of impaired motor abilities. PF-04457845 treatment significantly improved the time on the rod in the second, third and fourth trials. No differences were found between treated and non-treated wt mice.

Hippocampal dependent memory was monitored by the Y maze test (FIG. 13). During the first training trial (8 min) the mice were only allowed to explore two arms (the initial arm and one other arm), maintaining the third arm (novel arm) closed. After 1 hour, the mice were placed back in the same starting arm with free access to all three arms for 5 min. The time spent in the novel arm was counted and expressed as a percentage of the total exploration time. Non-treated ASMko mice spent less time in the novel arm than wt mice, indicative of impaired memory. PF-04457845 treatment restored memory function in ASMko mice to the values found in wt mice. No differences were found between treated and non-treated wt mice.

Mood alterations were monitored by the Tail Suspension Test (FIG. 13B) and by the Elevated Plus Maze test (FIG. 13C) that give an idea of depressive state and anxiety, respectively. ASMko mice showed altered behavior in both tests that was normalized upon treatment with PF-04457845. PF-04457845 treatment had no effect in the behavior of wt mice.

Biochemical and Histological Analysis

Figure 14:
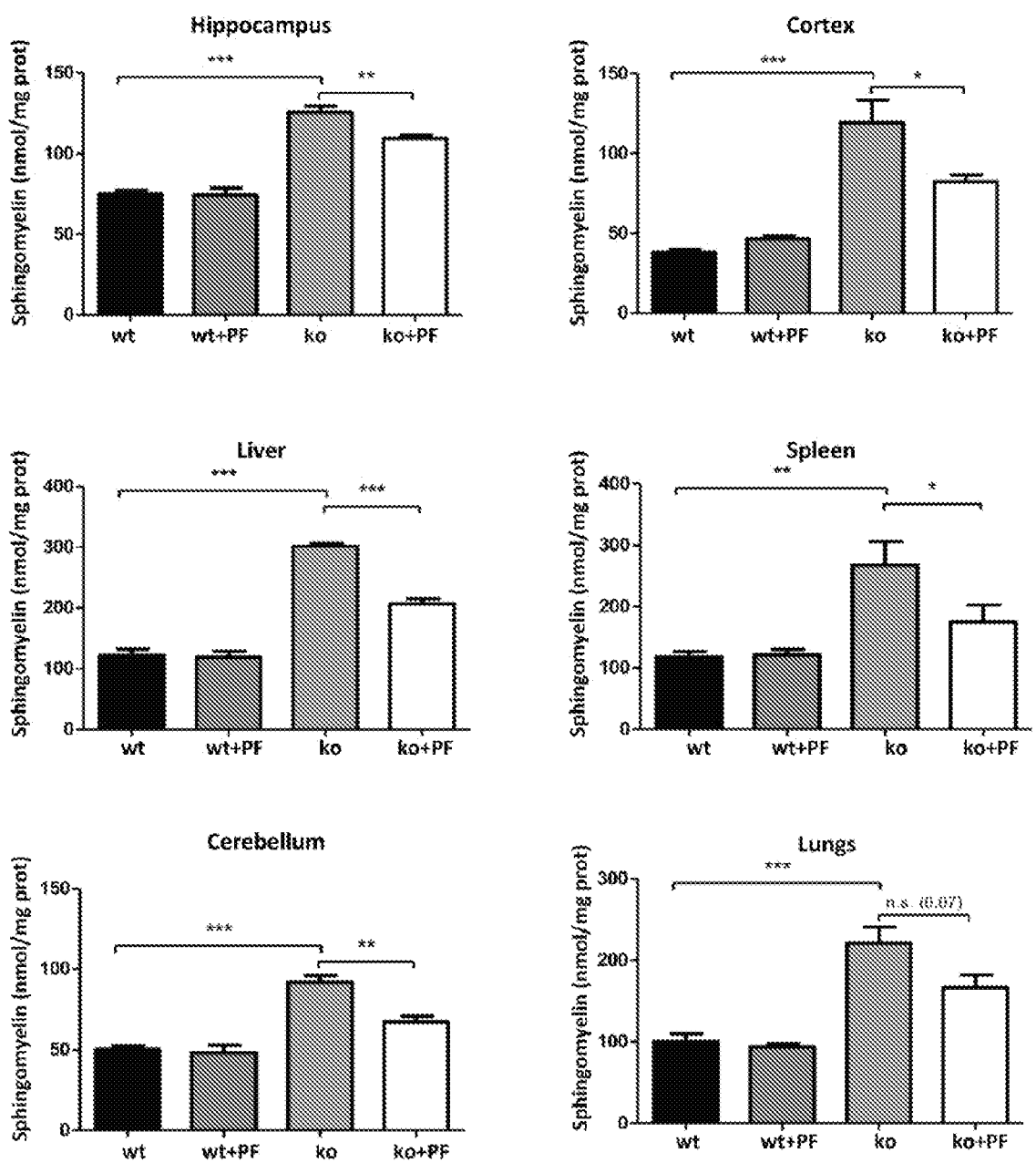
FIG. 14 shows mean±SEM sphingomyelin levels (in nmol/mg protein) in extracts from hippocampus, cortex, cerebellum, liver, spleen, and lungs of wt and ASMko mice treated or not with PF-04457845 (n=7; *p<0.05, p<0.01, *p<0.001).

Sphingomyelin levels were measured by enzymatic assays in extracts of different brain areas and in liver, spleen, and lung (FIG. 14). The results confirmed the remarkable increase of sphingomyelin levels in all organs of the ASMko mice compared to wt and showed a significant reduction of sphingomyelin in ASMko mice treated with PF-04457845 in the hippocampus, cortex, cerebellum, liver and spleen, as well as a non-statistically significant trend towards a decrease in the lung. This treatment did not alter sphingomyelin levels in wt mice.

Figure 15A:
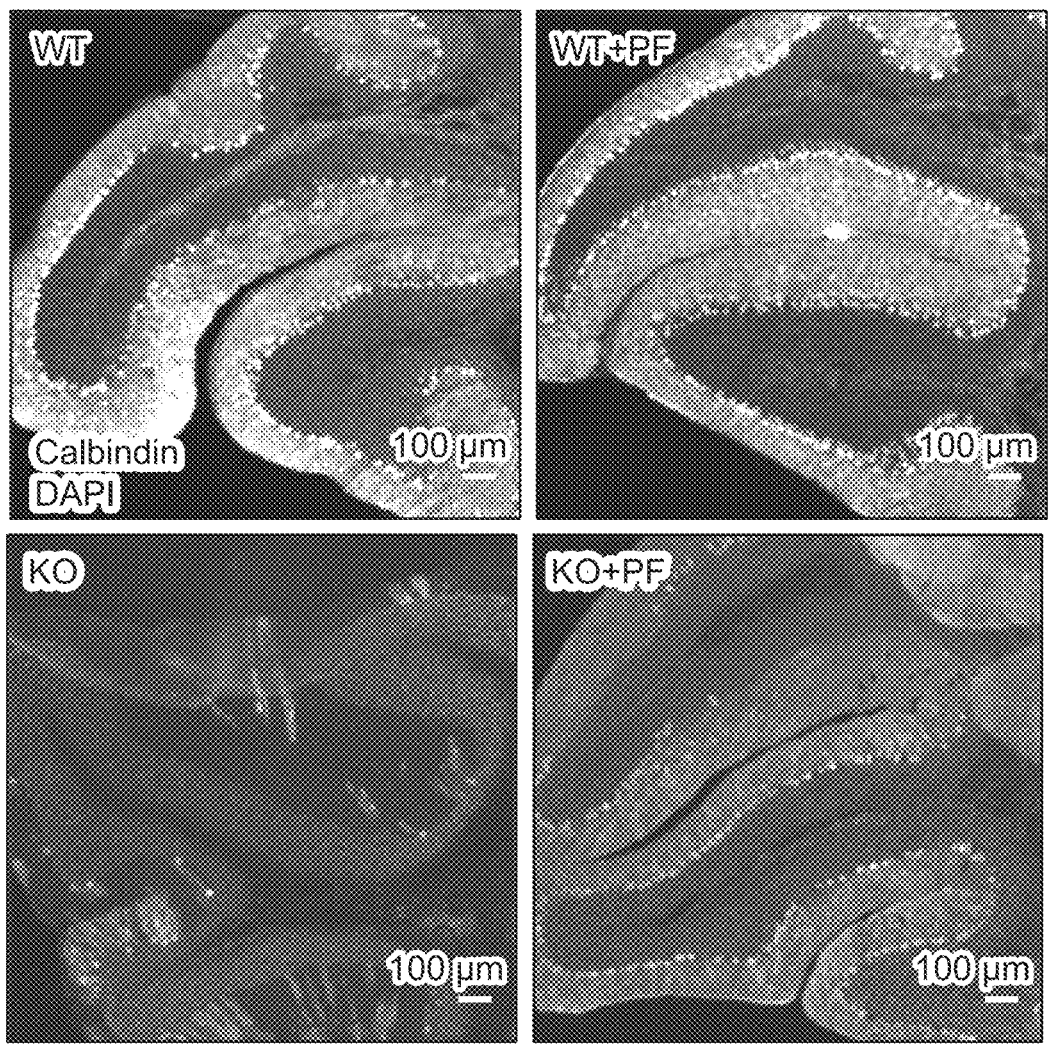
FIG. 15A shows representative images of Purkinje cells stained for CalbindinI (green) in the cerebellum of wt and ASMko mice treated or not with PF-04457845. Dapi in blue shows cell nuclei.
Figure 15B:
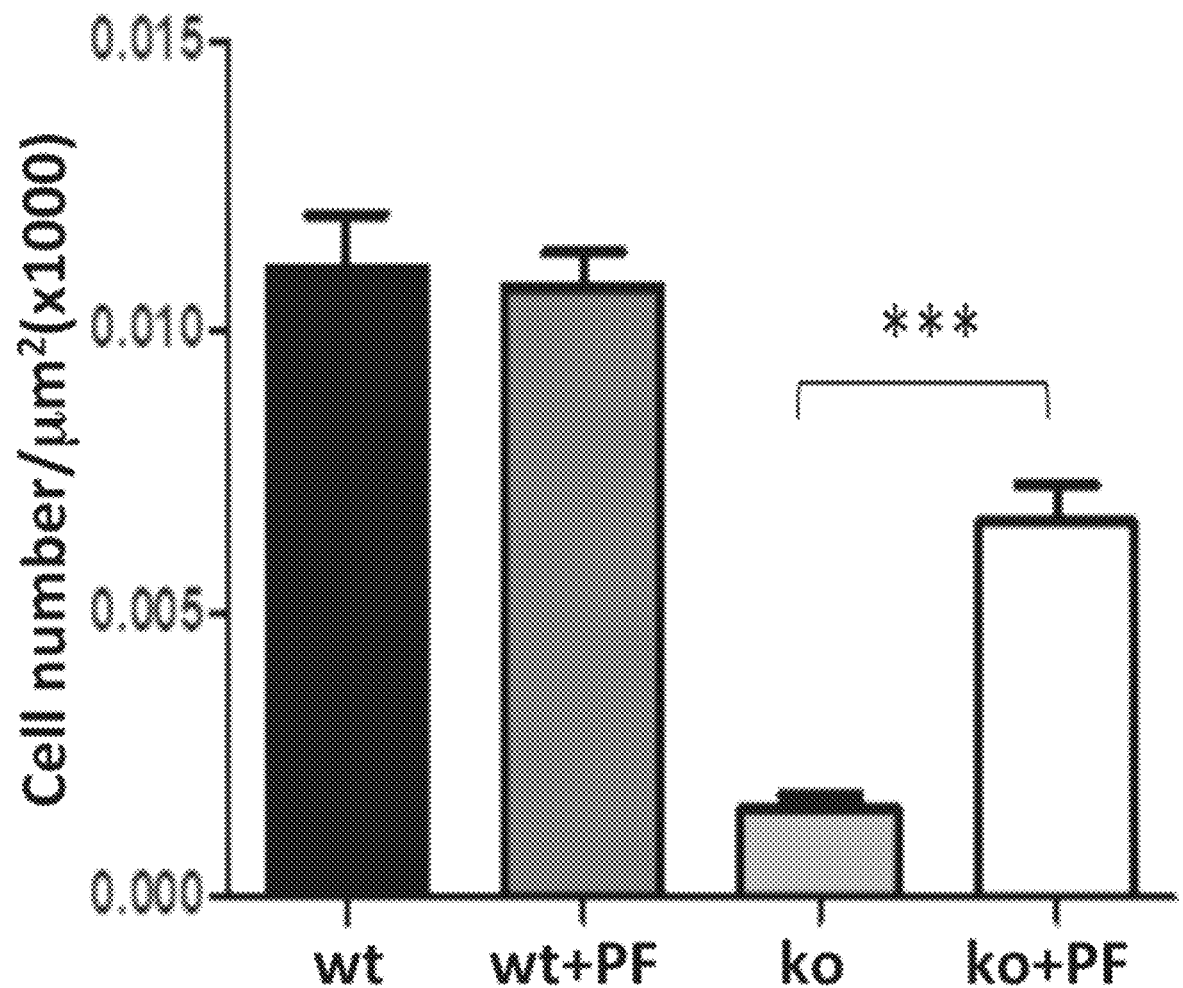
FIG. 15B shows graphs of the mean±SEM number of Purkinje cells per area (n=7, *p<0.001).
Figure 15C:
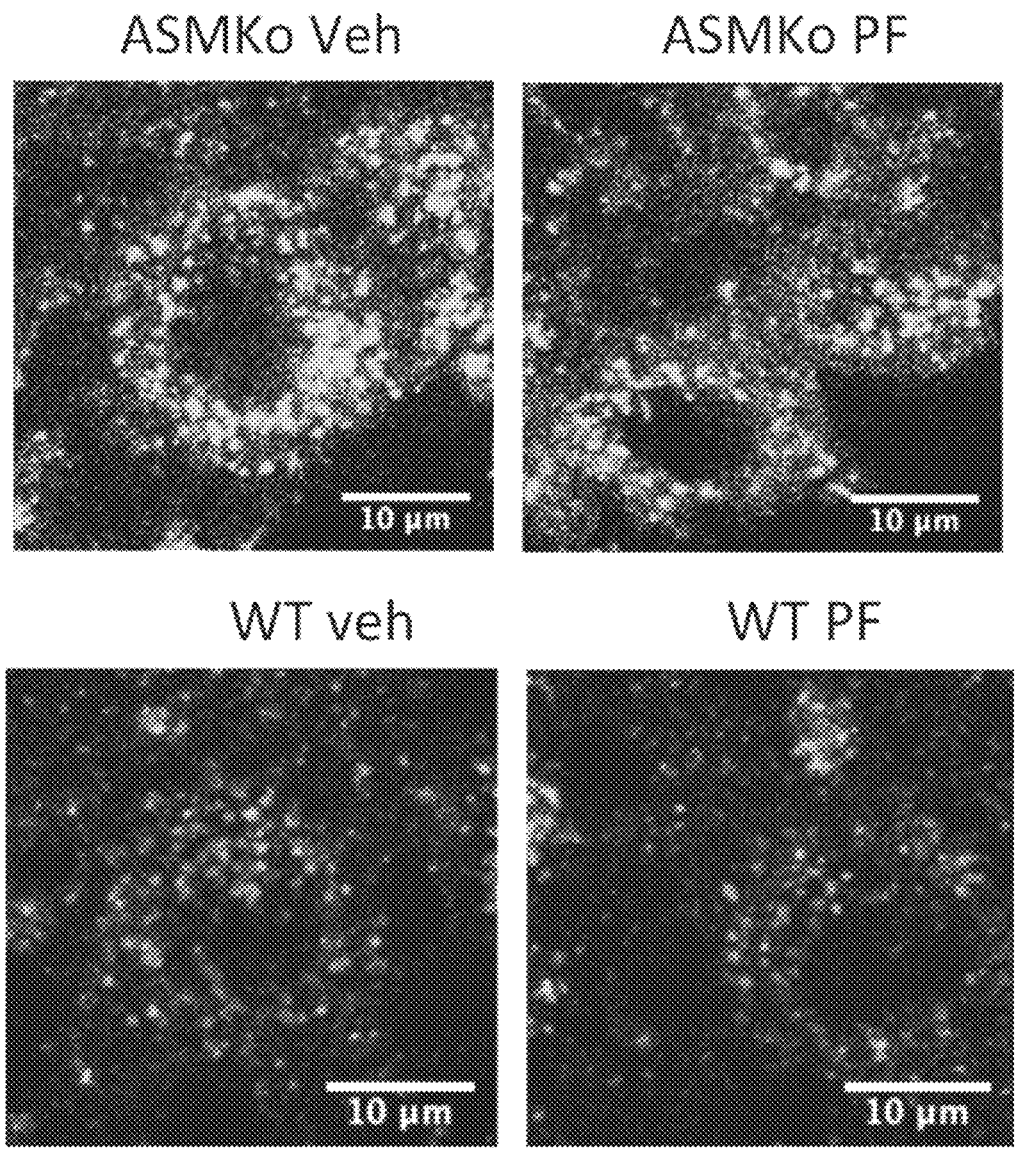
FIG. 15C shows representative images of Purkinje cells stained for Lamp1 (green) in the cerebellum of wt and ASMko mice treated or not with PF-04457845.
Figure 15D:
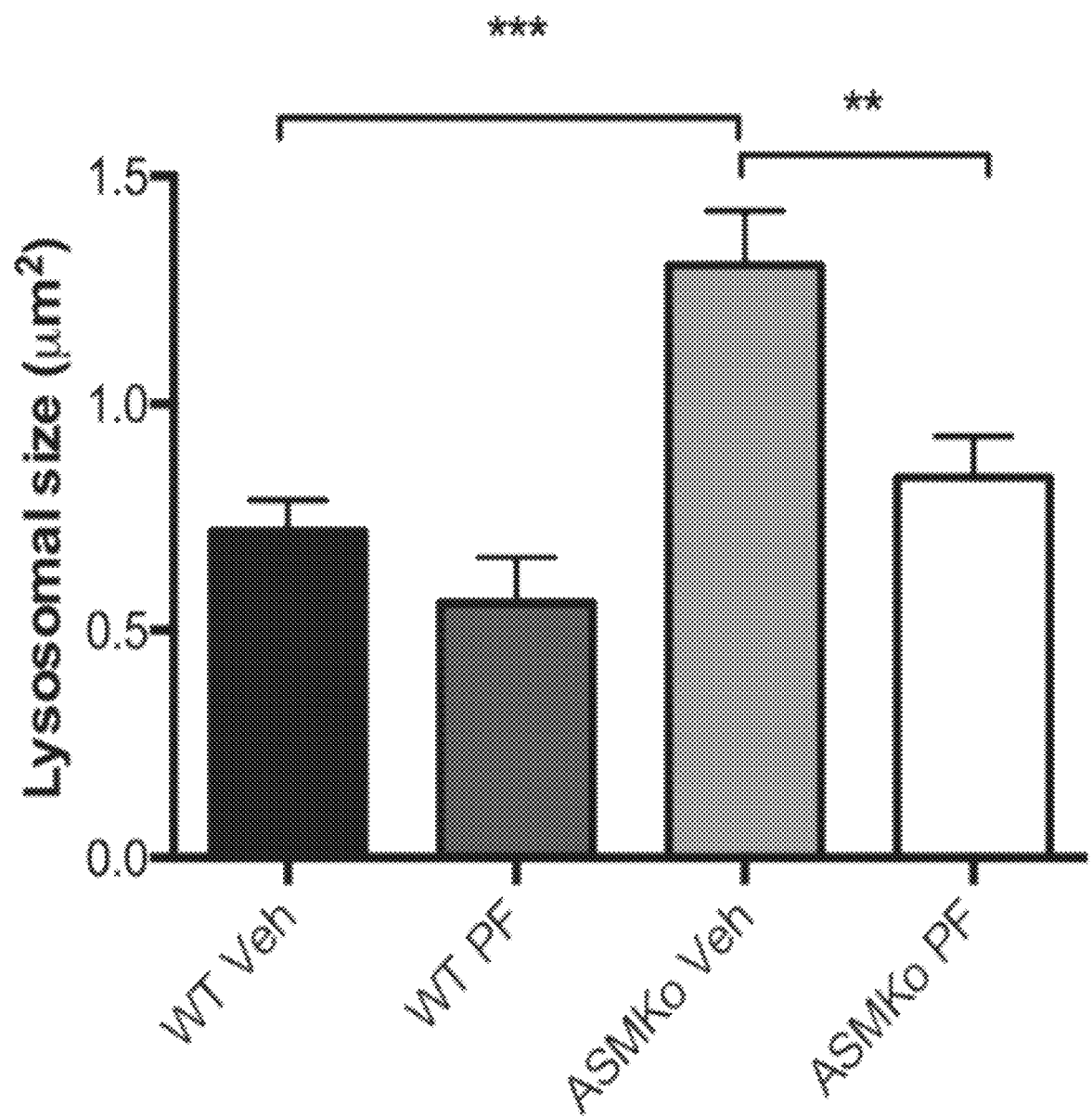
FIG. 15D shows graphs of the mean±SEM area of lysosomes (n=7; *p<0.001, **p<0.01).

Purkinje cell death was analyzed by Calbindinl staining in the cerebellum of wt and ASMko treated or not with PF-04457845 (FIG. 15A). Loss of Purkinje cells was prominent in non-treated ASMko mice compared to wt. PF-04457845 treatment prevented cell death in a significant percentage of cells. PF-04457845 treatment had no effect on Purkinje cell survival in wt mice. We also analyzed Lysosomal size by staining Purkinje cells of the cerebellum for Lamp 1 expression in samples from wt and ASMko mice treated or not treated with PF-04457845 (FIG. 15B). Lysosomal size was increased by an average 45% in the non-treated ASMko compared to wt mice consistent with sphingomyelin accumulation in these organelles. This alteration was prevented to a significant extent (35%) in the ASMko mice treated with PF.

Figure 16:
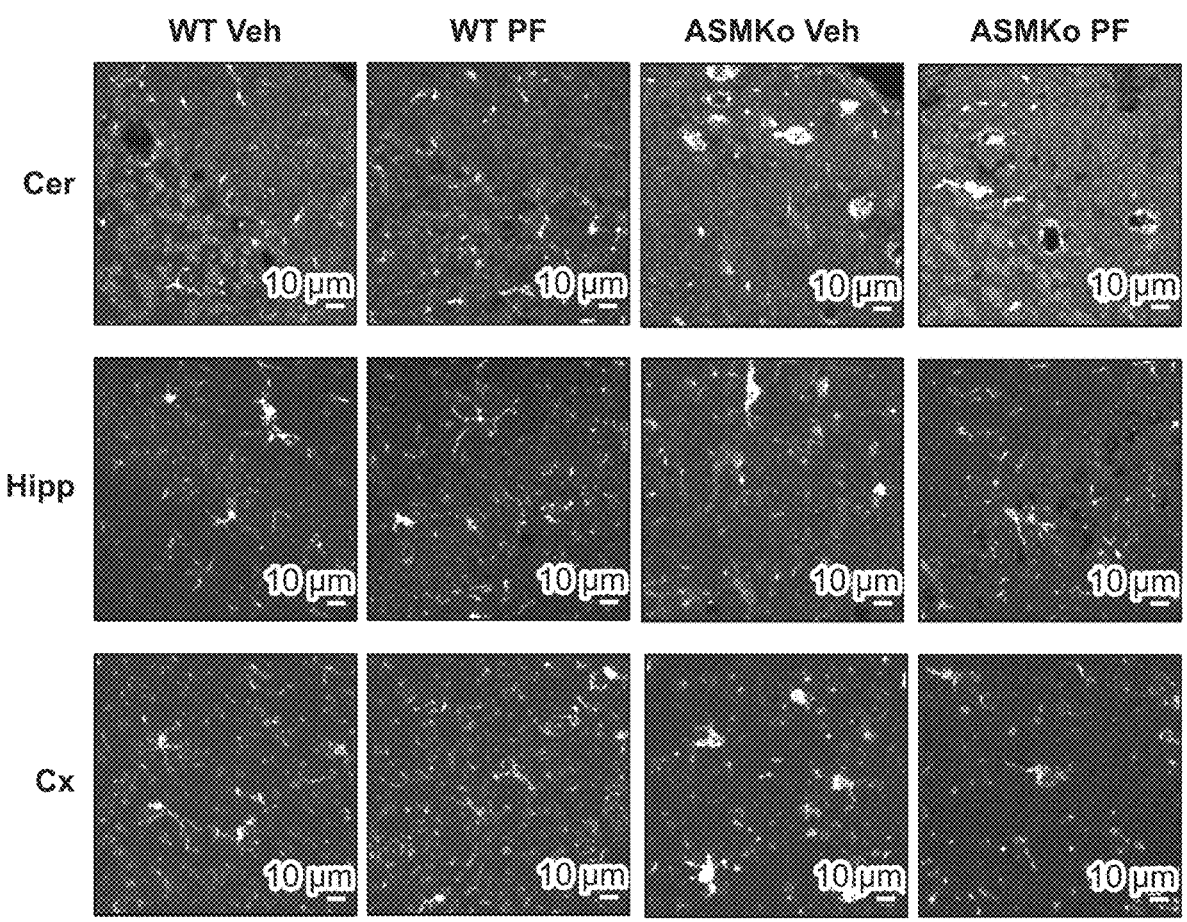
FIG. 16 shows the effect of PF-04457845 on microglia as a readout for brain inflammation. Representative images of microglia stained for iba-1 (green) in the cerebellum, hippocampus and cortex of wt and ASMko mice treated or not with PF-04457845. Dapi in blue shows cell nuclei. Graphs show mean±SEM microglia number and cell body area (n=7, **p<0.01, *p<0.05).
Figure 16:
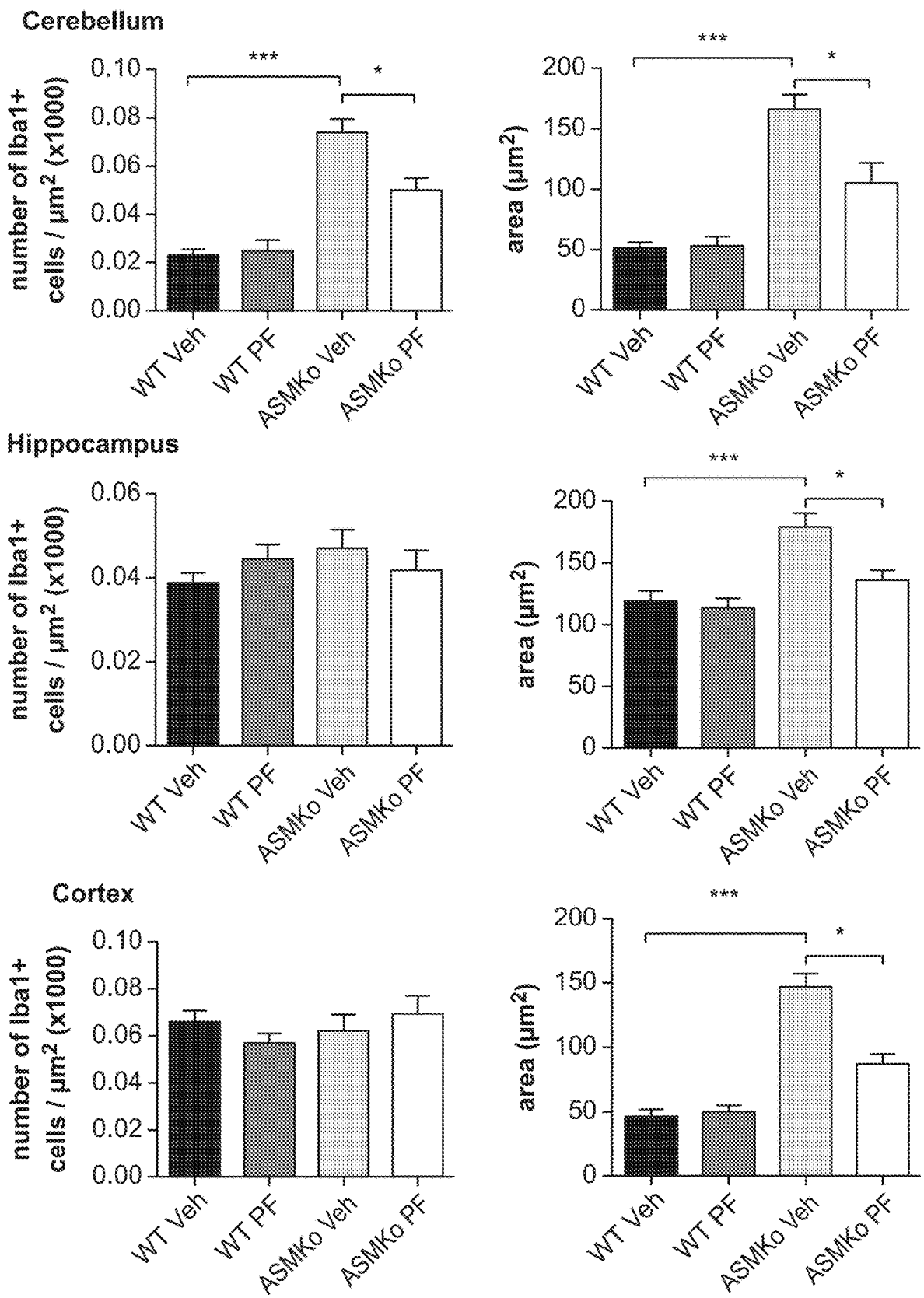
Figure 17:
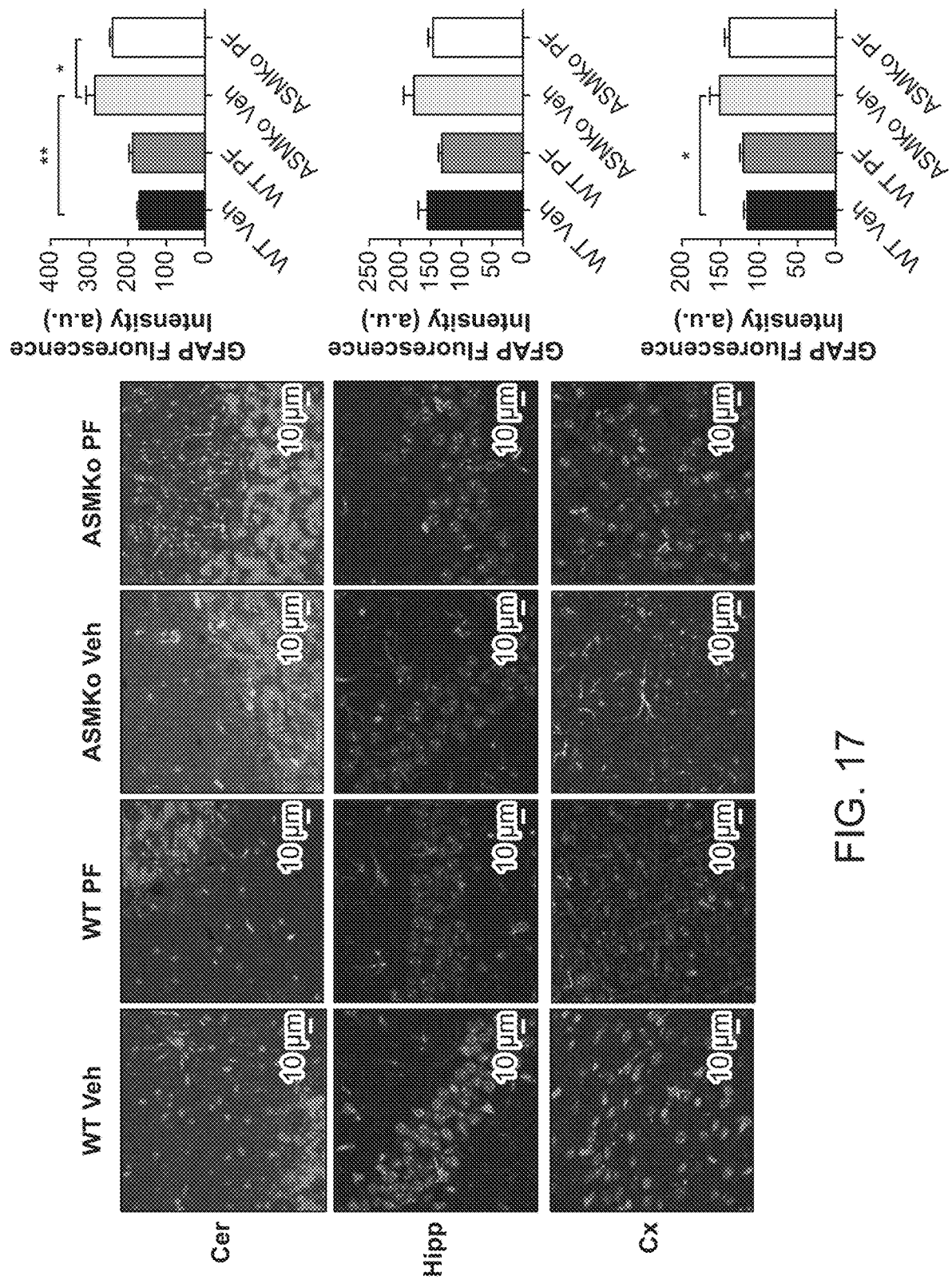
FIG. 17 shows the effect of PF-04457845 on astrocytes as a readout for brain inflammation. Representative images of astrocytes stained for GFAP (red) in the cerebellum, hippocampus and cortex of wt and ASMko mice treated or not with PF-04457845. Dapi in blue shows cell nuclei. Graphs show mean±SEM GFAP intensity in arbitrary units (n=7, **p<0.01, *p<0.05).

Brain inflammation was determined by analysis of glial cells in the cerebellum, hippocampus and cortex. The number and morphology of microglia was analyzed by immunofluorescence staining with the marker iba-1 (FIG. 16). The cerebellum of non-treated ASMko mice showed increased number of microglia and amoeboid morphology (reflected by increased cell area and indicative of maximally activated state) compared to wt mice. PF-04457845 treatment in ASMko mice reduced microglia number and normalized their morphology. In the hippocampus and cerebellum of non-treated ASMko mice we did not observe increased microglia number but amoeboid morphology that was normalized to a significant extent by PF treatment (FIG. 16). PF-04457845 treatment had no effect in microglia of wt mice. The amount of astrocytes was analyzed by immunofluorescence with the marker GFAP (FIG. 17). ASMko mice showed significant increased GFAP intensity in the cerebellum and cortex and non-significant tendency to increase in the hippocampus compared to wt mice (FIG. 17). PF-04457845 treatment reduced GFAP intensity in all areas but the effect was significant only in the cerebellum. PF-04457845 treatment had no effect in astrocytes of wt mice (FIG. 17).

Endocannabinoid Analysis

Figures 18, 18A:
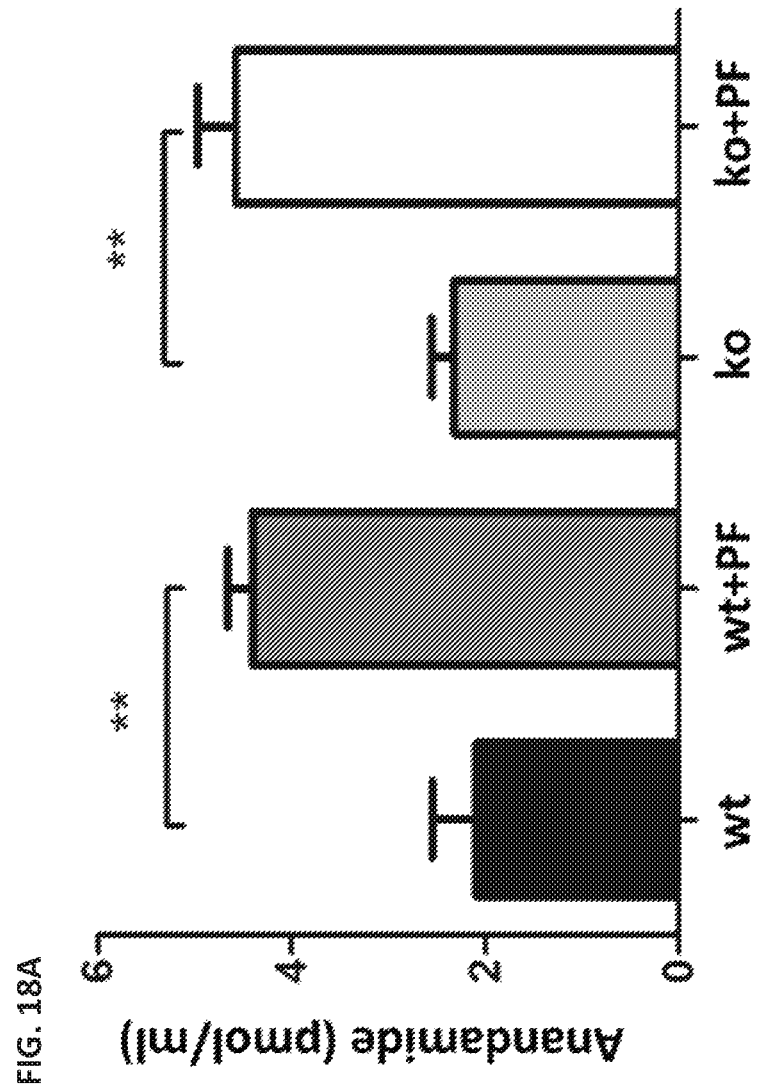
FIG. 18 shows hippocampal anandamide and CB1 levels in wt and ASMko mice treated or not treated with PF-04457845.
FIG. 18A shows mean±SEM anandamide levels (in pmol/ml tissue) in extracts from the hippocampus of wt and ASMko mice treated or not with PF (n=7; **p<0.01).

PF-04457845 inhibits the enzyme (FAAH) that hydrolyzes the endocannabinoid anandamide, which in turn activates the CB1 receptor leading to neutral sphingomyelinase activation and sphingomyelin hydrolysis. To determine the effects of PF-04457845 treatment in the endocannabinoid system we analyzed anandamide and CB1 levels in the brain of PF-04457845 treated and non-treated mice. In agreement with an efficient inhibition of FAAH, the levels of anandamide measured by mass spectrometry were increased in the hippocampus of PF-04457845 treated wt and ASMko mice by 2.09 and 1.96-fold, respectively (FIG. 18A).

Figure 18B:
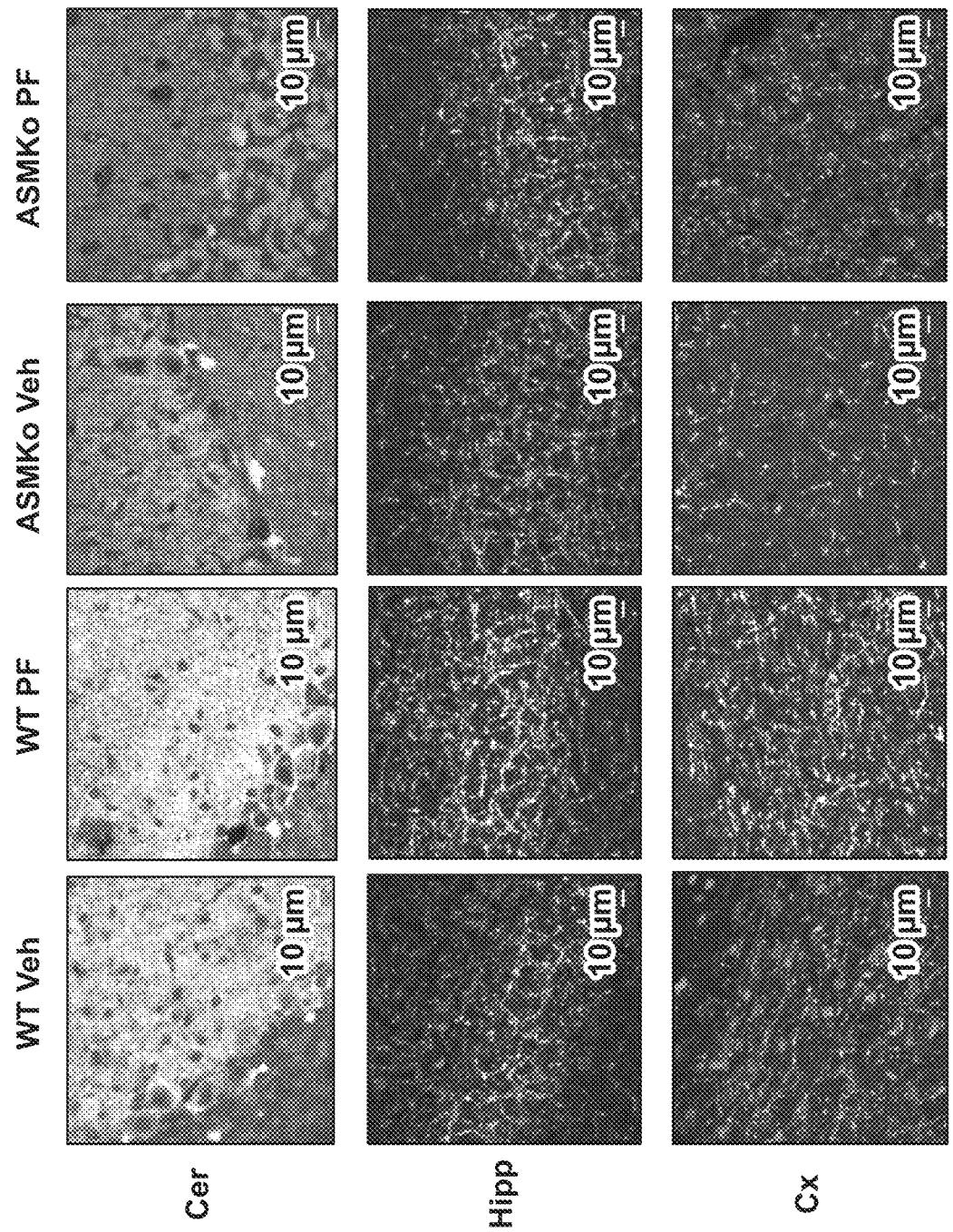
FIG. 18B shows representative images of CB1 (green) in the cerebellum, hippocampus and cortex of wt and ASMko mice treated or not with PF. Dapi in blue shows cell nuclei. Graphs show mean±SEM CB1 intensity in arbitrary units (n=5, *p<0.05).
Figure 18B:
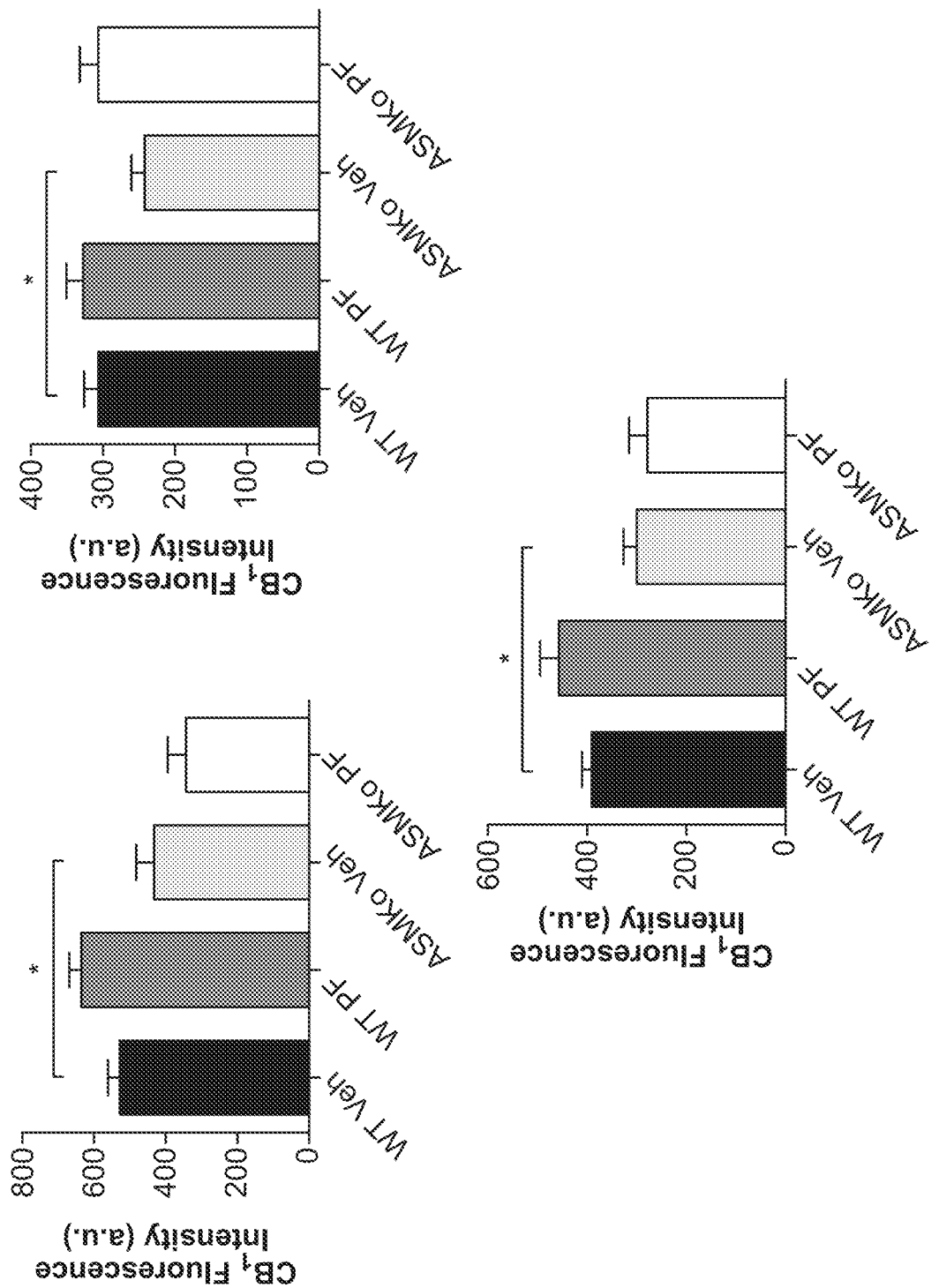
Figure 20:
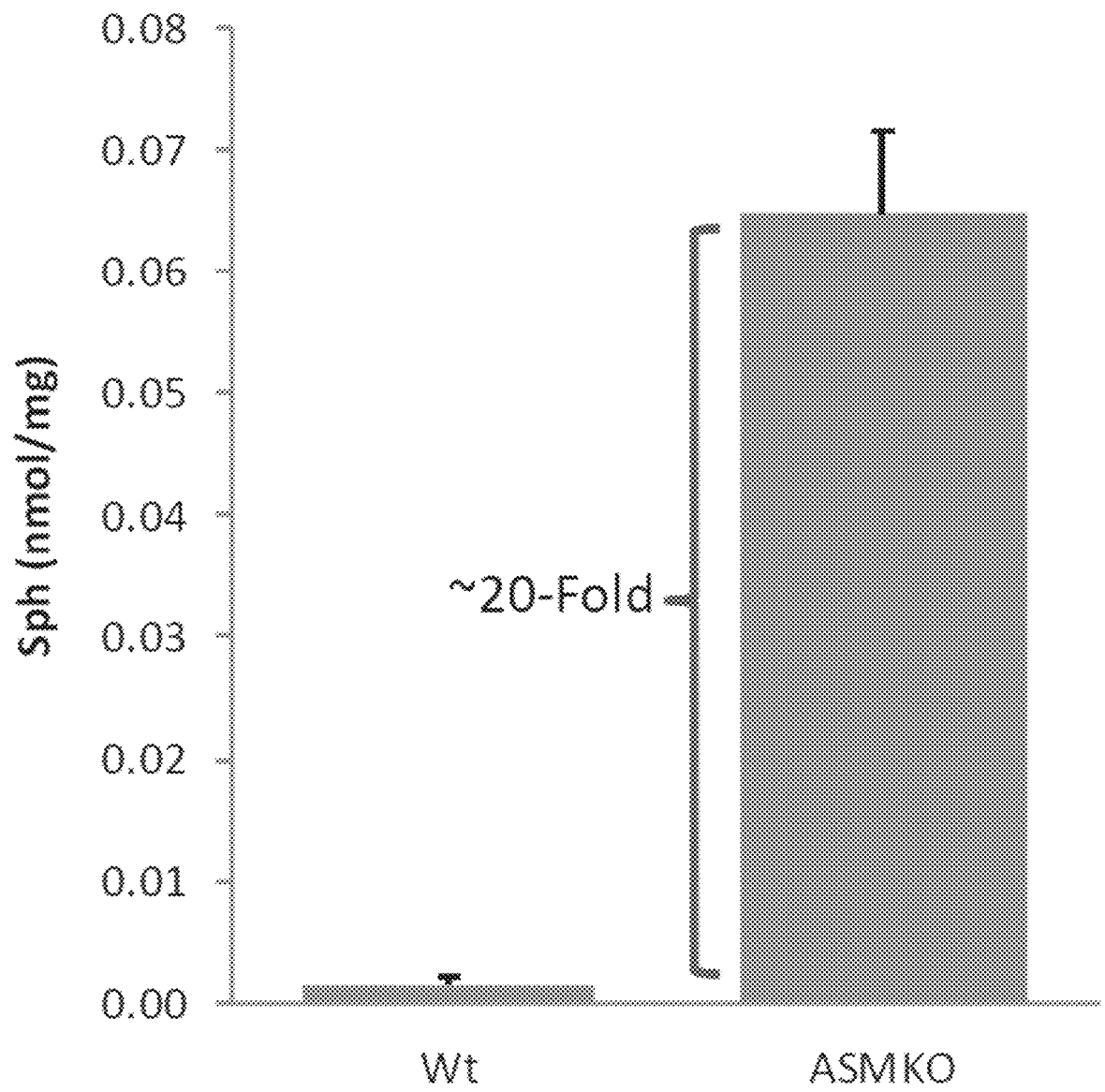
FIG. 20 shows increased sphingosine levels in the liver of ASMko mice.

CB1 levels were reduced in the hippocampus, cortex, and cerebellum of ASMko mice as determined by immunofluorescence using an specific antibody (FIG. 18B). PF-04457845 treatment did not have significant effect on CB1 levels in any of these ASMko brain areas (FIG. 18B). In wt mice PF-04457845 treatment showed a trend to increase CB1 levels in all areas but this trend did not reach statistical significance (FIG. 18B).

Survival Analysis

Seven mice per condition remained under treatment to monitor life span. While the mean survival of non-treated ASMko mice was 29 weeks, PF-04457845 treatment extended ASMko mice mean life span to 38 weeks (FIG. 19). The treatment did not affect wildtype mice survival.

Conclusions and Perspectives

Oral PF-04457845 treatment for 1.5 months at 0.3 mg/kg every three days shows benefits in different brain regions and in peripheral organs in ASMko mice resulting in:
  a. improved motor, memory, and emotional behavior;
  b. reduced sphingomyelin levels in hippocampus, cortex, cerebellum, liver and spleen; and
  c. reduced death and lysosomal size of Purkinje cells in the cerebellum;
  d. reduced inflammation as monitored by microglia number and morphology and by astrocyte associated intensity.

PF-04457845 treatment increased anandamide levels in brain but did not result in significant changes on CB1 expression in any of the brain areas analyzed in ASMko mice. PF-04457845 treatment improved body weight gain and significantly extended lifespan by 31% in ASMko mice.

The effects are not gender dependent, as they were equally observed in females and males. Oral PF-04457845 treatment for 1.5 months at 0.3 mg/kg every three days shows no effects in wt mice in any of the parameters analyzed.

While the benefits are clear, there is still a margin to further enhance the reduction of sphingomyelin levels and bring them closer to the levels observed in wt mice. Because much higher PF-04457845 doses than the one used here (up to 10 mg/kg) seem to be safe in rodents (Ahn et al., 2011) and are well tolerated in healthy humans (Li et al., 2011) we are performing scaled up, dose-response study to determine optimal dosing. We are also developing methods of monitoring fatty acid amide and/or ceramide in plasma and/or CSF as biomarkers for ASMD and FAAHi sensitivity.

Thus, activation of the CB1 cannabinoid receptor via the inhibition of FAAH provides a valid means for treating or preventing ASMD by inhibiting the pathological cellular accumulation of SM.

Example 6

Analysis of CB1 Expression in Human NPA Patients

Figure 21:
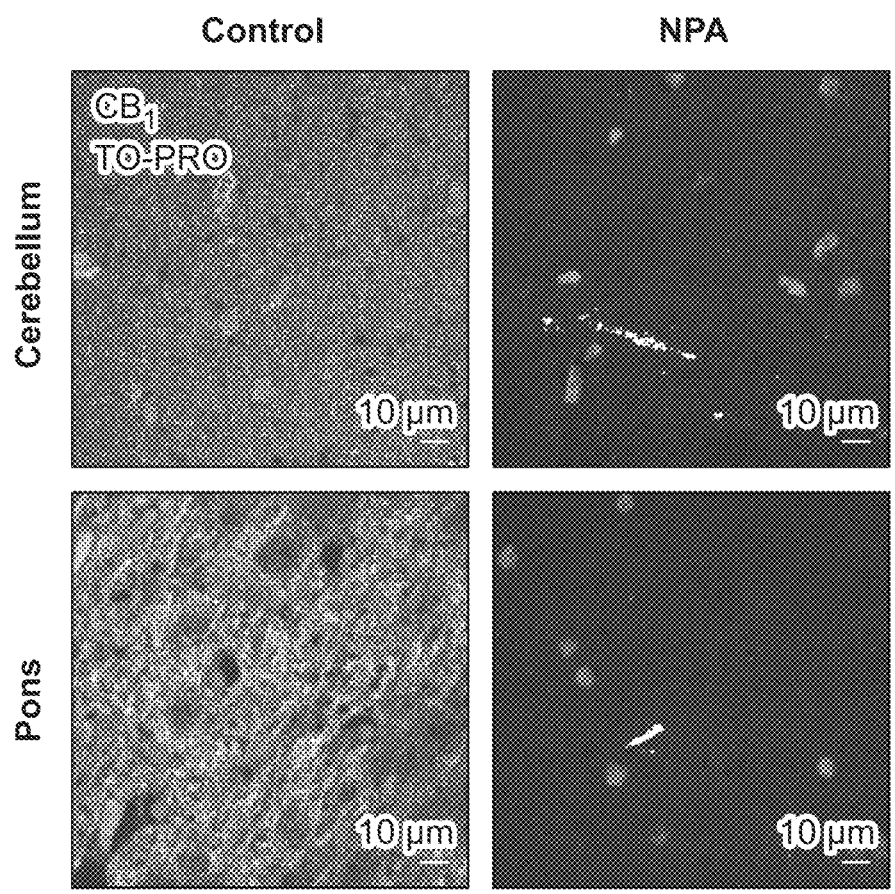
FIG. 21 shows that CB1 receptor levels are low in the Cerebellum and Pons of a human NPA patient compared to a control child, and the receptor expression is restricted to lysosome-like structures in the cell bodies.
Figure 22A:
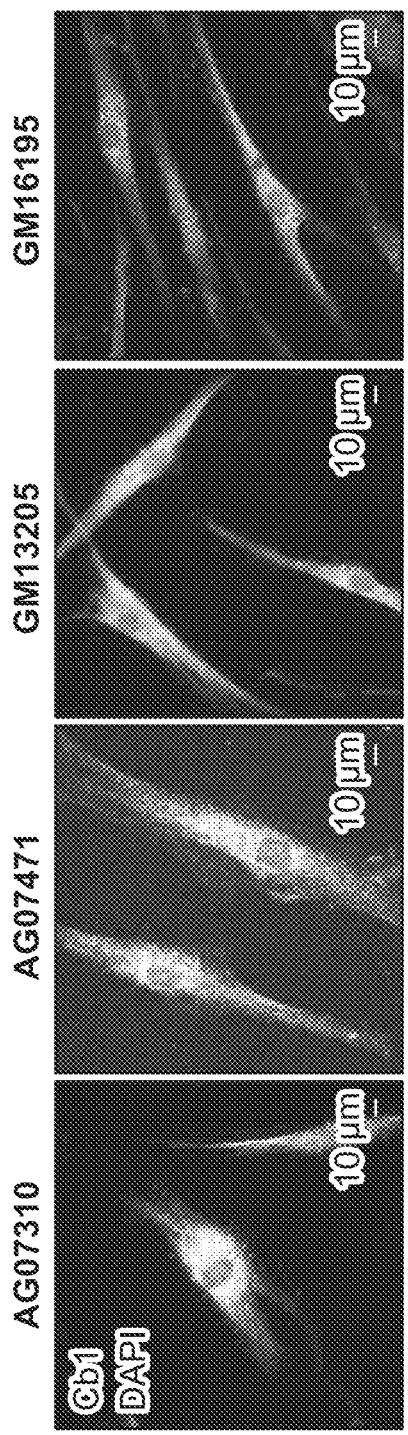
FIG. 22A shows representative images of control (AG07310 and AG07471) and NPA patient-derived (GM13205 and GM16195) fibroblasts stained for CB1 (green). Dapi in blue shows cell nuclei.
Figure 22B:
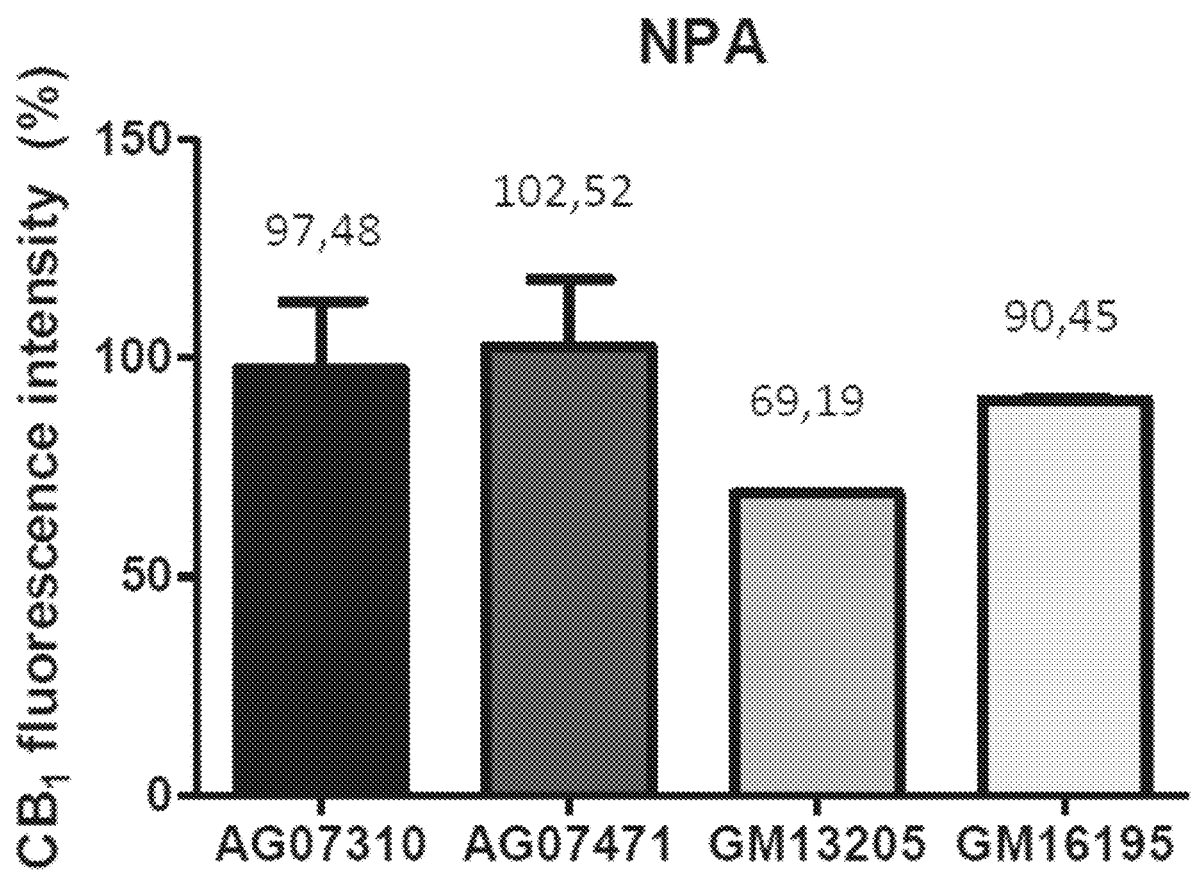
FIG. 22B graphs show mean CB1 fluorescence intensity %. Measurements in the control cell lines were done in two independent cultures each. The mean of these values was considered 100%.

Given the low expression of CB1 found in the brains of ASMko mice, which are a model of NPA, we sought to determine whether similar alteration occurs in patients. CB1 protein expression was analyzed in the brain tissue and in fibroblasts of NPA patients. CB1 levels were significantly reduced, and its distribution altered, in the cerebellum and Pons of an NPA patient (FIG. 21). CB1 levels were also reduced, although to a lesser extent, in fibroblasts from two other NPA patients (FIG. 22).

Example 7

Acute Toxicity Report

Given that the CB1 expression profiles observed in the AMSko mice were found to be present in the brains and cultured fibroblasts from NPA patients, we determined that a human clinical study assessing the efficacy of PF-04457845 for treating human NPA was merited.

To that end, a toxicity assessment of oral PF-04457845 treatment in AMSko mice was performed to determine the toxicity in liver and brain of single doses of PF-04457845 administered by oral gavage at different concentration.

Results

Mouse Distribution and Treatment

We divided wt and ASMko mice of 4.5 months of age in six experimental groups: ASMko control (n=3), ASMko low dose (n=3), ASMko intermediate dose (n=3), ASMko high dose (n=3), wt control (n=3), wt high dose (n=3). PF-04457845, provided as powder, was dissolved in 0.9% NaCl and administered to mice through oral gavage. Vehicle groups received same volume of 0.9% NaCl.

Doses have been calculated taking into account that used in the study conducted in healthy humans (Li et al., Br J Clin Pharmacol 2011, 73:706-716). These authors concluded that 0.5 mg of PF-04457845 once daily should be sufficient, well tolerated and provide maximal effects on FAAH activity and fatty acid amide elevation. Estimating an average weight of 60 kg for an adult human the daily dose equals to 0.0083 mg/kg. This dose was very similar to that used in our first 8 week-long treatment with PF-04457845 in ASMko mice, which according to the formulas to calculate equivalence between humans and mice (Nair and Jacob J Basic Clin Pharma 2016, 7:27-31) corresponded to a daily HED dose of 0.0072 mg/kg. For this toxicity study we agreed to take into account the human dose: 0.0083 mg/kg. Formula conversion to mouse dose: HED (mg/kg)=Mouse dose (mg/kg)× mouseKm/Human Km). According to the Km values in Nair and Jacob this results in: 0.0083=Mouse dose×(3/37):

Mouse dose=0.102 mg/kg.
 Therefore the final doses we have used in the mouse toxicity assessment were: Low dose: 0.1 mg/kg
 Intermediate dose×10=1 mg/kg
 High dose×50=5 mg/kg In-Life Observations and Sample Collection No evident adverse effects (abnormal behavior, weight loss, motor anomalies, skin alterations) were observed in wt or ASMko mice during the 48 hours following PF-04457845 administration at any of the doses.

After these 48 hours and immediately before termination we collected blood from mice and prepared serum by leaving blood samples 30 minutes for clotting at room temperature and by collecting the supernatant after centrifugation at 6000 rpm for 10 minutes. Following termination, mice were transcardially perfused with phosphate-buffered saline (PBS).

Brains and Livers were harvested and processed for biochemical, H&E and immunofluorescence analysis as previously indicated.

Lipid Analysis

Figure 26:
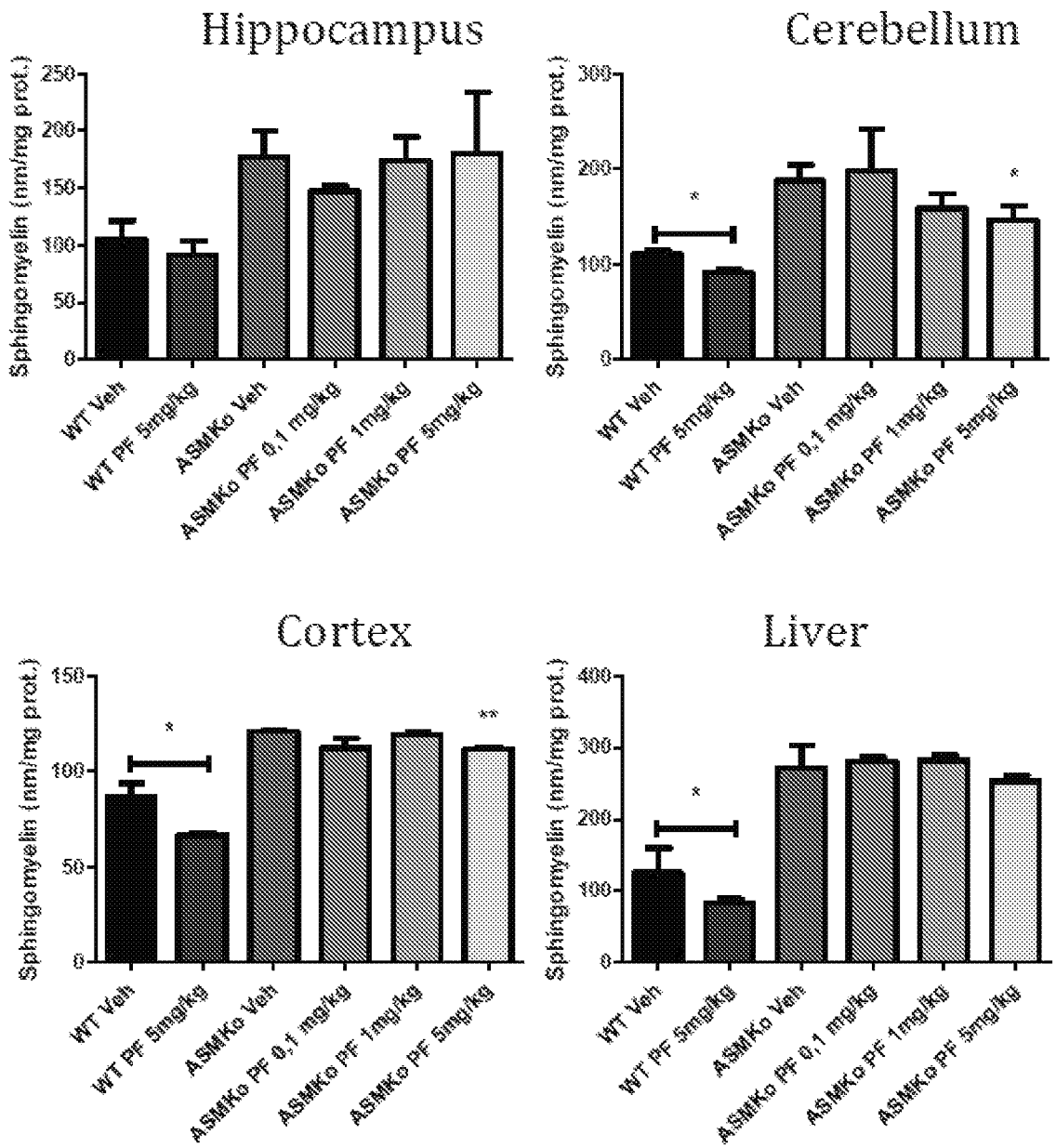
FIG. 26 shows mean±SEM sphingomyelin levels (in nmol/mg protein) in extracts from hippocampus, cortex, cerebellum and liver of wt and ASMko mice treated with PF-04457845 at the indicated doses or with vehicle (n=3; *p<0.05, **p<0.005, Student T-test).

Sphingomyelin levels were quantified by enzymatic assay in extracts from different brain areas (hippocampus, cerebellum and cortex) and from liver of wt and ASMko mice treated with PF-04457845 at 0.1 mg/kg, 1 mg/kg and 5 mg/kg or with vehicle (FIG. 26). The results confirmed the remarkable increase of sphingomyelin levels in the vehicle-treated ASMko mice with respect to wt at this advanced stage of the disease (168% in hippocampus, 170% in cerebellum, 139% in cortex and 216% in liver with respect to wt values considered 100%).

A single dose of 5 mg/kg PF reduced sphingomyelin levels by 13% in hippocampus, 17% in cerebellum, 23% in cortex and 34% in liver in wt mice. The reduction was statistically significant in all tissues except hippocampus. A single dose of 5 mg/kg PF-04457845 also reduced sphingomyelin levels by 21% in cerebellum, 8% in cortex and 6% in liver of ASMko mice. In the ASMko hippocampus the results with 5 mg/kg showed high variability. No statistically significant reduction of sphingomyelin was observed with 0.1 mg/kg or 1 mg/kg PF-04457845 although there was a tendency to reduction in some cases.

SM and ceramide levels were also monitored in the blood of wt and ASMko mice with and without PF-04457845 treatment as a readout of acute toxicity. We did not observe increases of either SM or ceramide in either group and, in fact, SM levels showed a moderate dose-dependent decrease in the ASMko mice and ceramide levels also decreased at the PF-04457845 doses of 1 and 5 mg/kg, but show high variability with a tendency to increase at 0.1 mg/kg (data not shown).

H&E Analysis

Figure 27A:
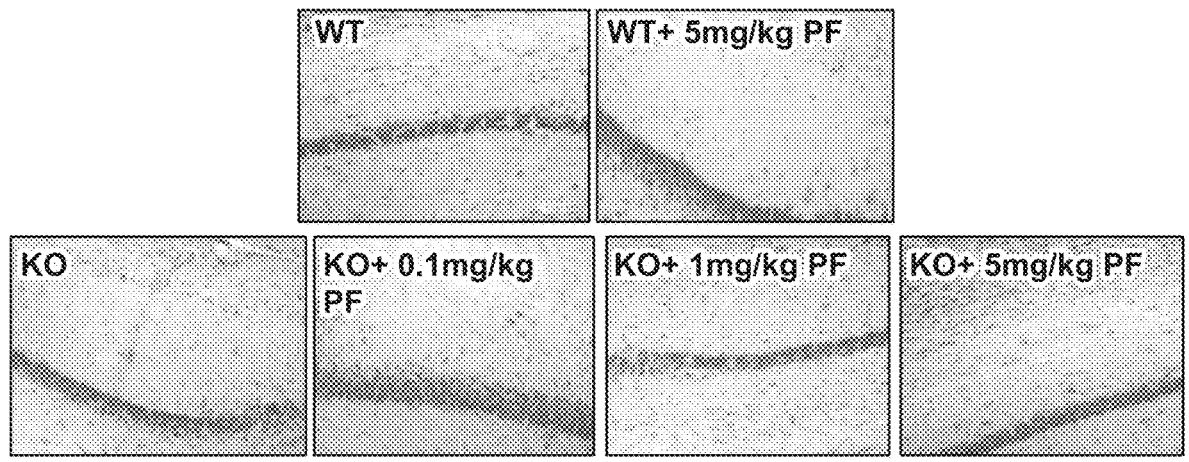
FIG. 27A shows staining of hippocampus.
Figure 27B:
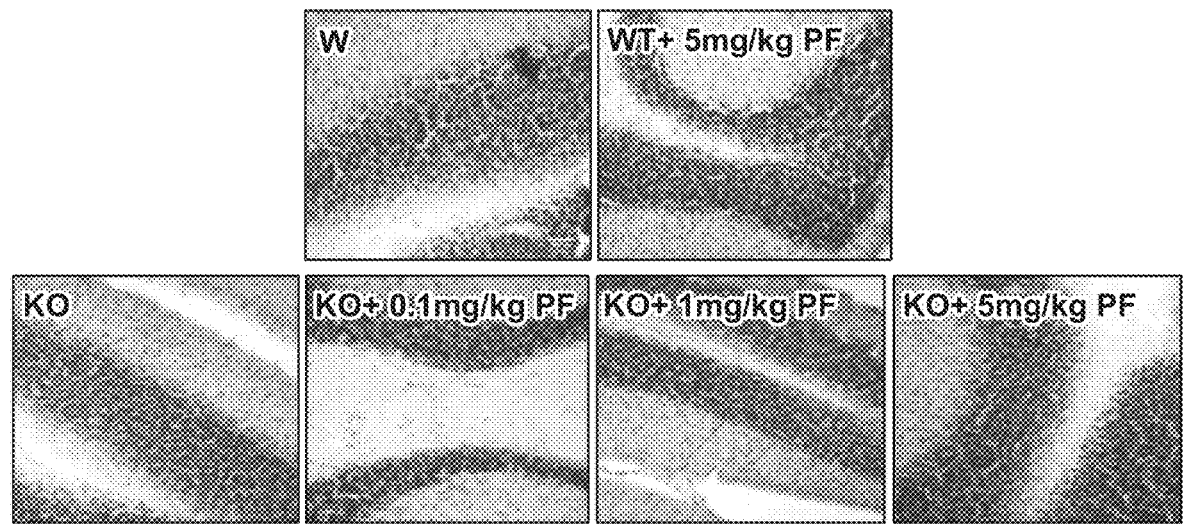
FIG. 27B shows staining of cerebellum.
Figure 27C:
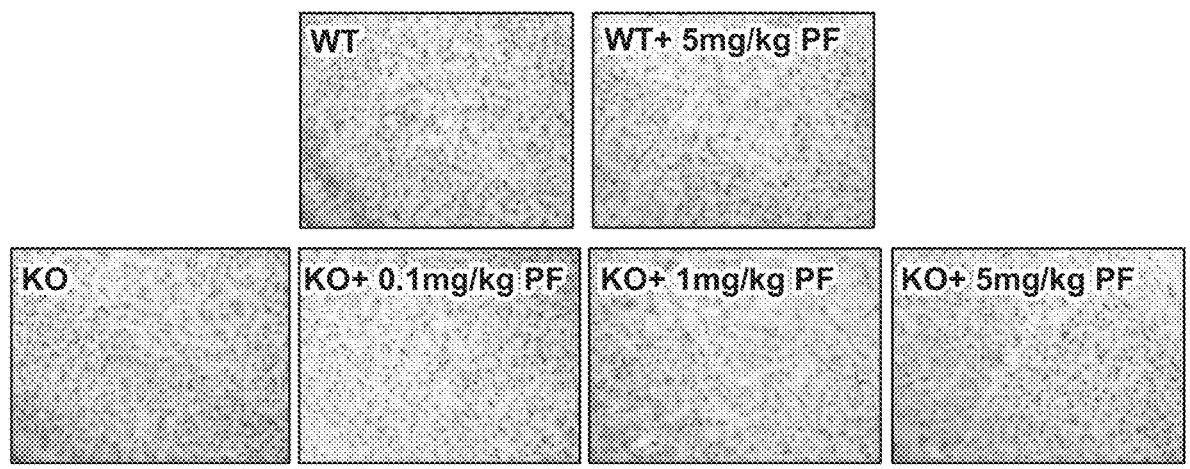
FIG. 27C shows staining of cortex.

Brain and liver tissue was stained with H&E to evaluate histopathological features. No significant differences were observed in any of the brain areas analyzed (hippocampus, cerebellum and cortex) between wt and ASMko vehicle-treated mice (FIGS. 27A-27C). PF-04457845 treatment did not cause significant changes in H&E staining in wt and ASMko mice at any of the doses (FIGS. 27A-27C).

Figure 28:
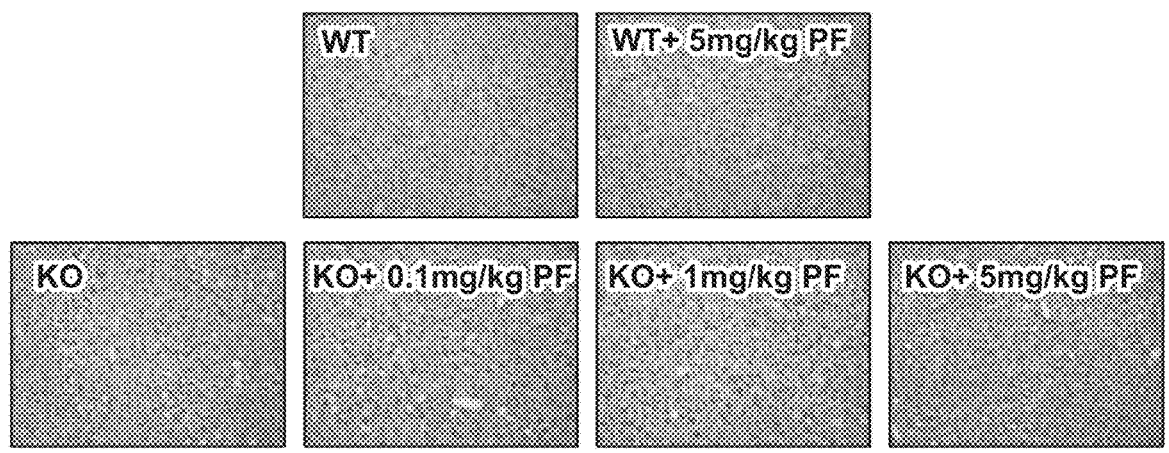
FIG. 28 shows representative images of H&E staining in the liver of wt and ASMko mice treated with PF-04457845 at the indicated doses or with vehicle.

In the liver foam cells showing white vacuoles indicative of lipid accumulation were evident in vehicle treated ASMko mice compared to wt (FIG. 28). PF-04457845 treatment did not significantly alter this pattern in the ASMko mice at any of the doses nor did it have effects in the wt mice (FIG. 28).

Inflammation Analysis

Figure 29A:
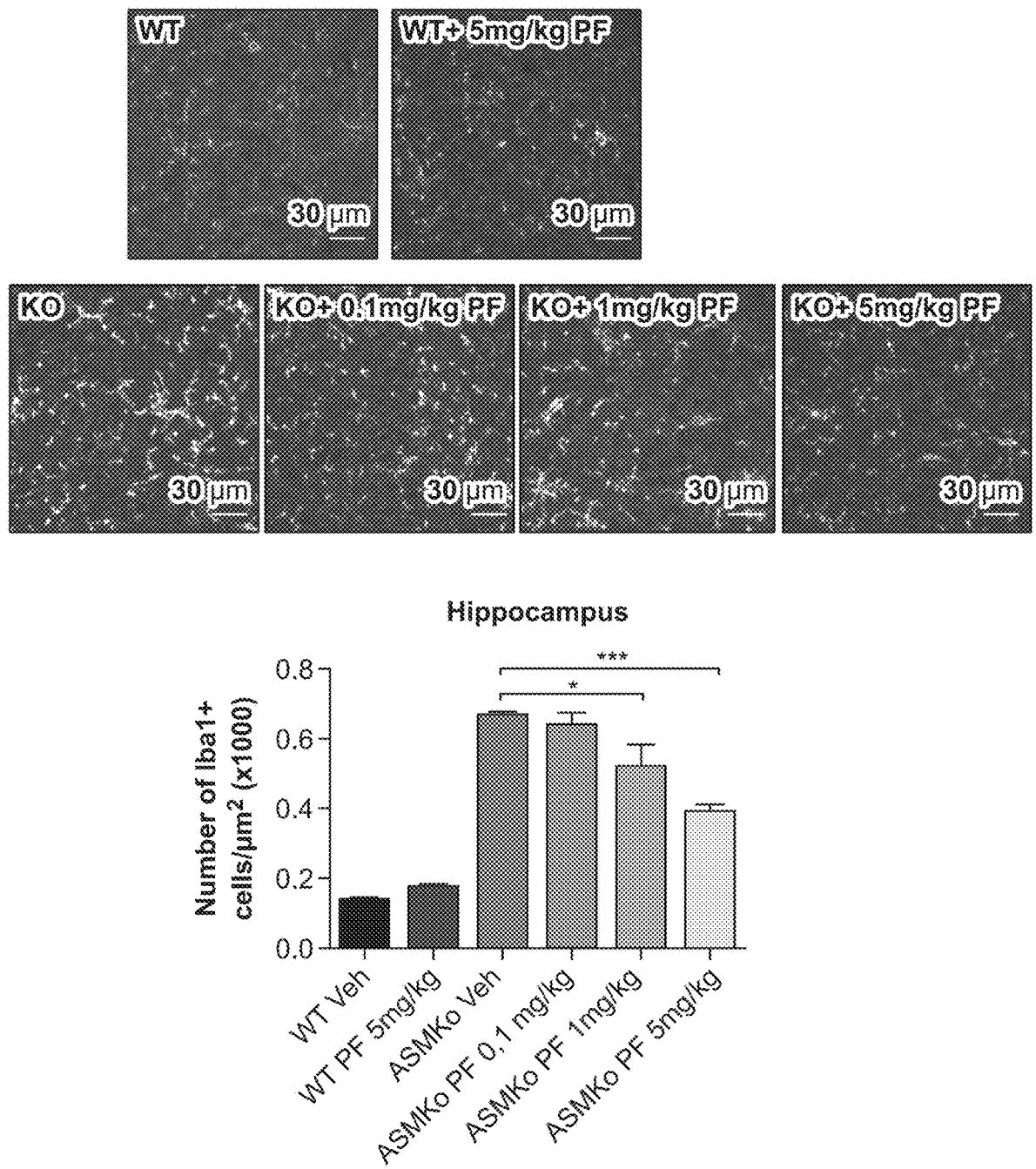
FIG. 29A-29C show iba1 expression in hippocampus, cerebellum, and cortex, respectively, of wt and ASMko mice treated with PF-04457845 at the indicated doses or with vehicle. Graphs shows mean±SEM number of iba-1 positive cells ((*p<0.05; ***p<0.001, Student T-test).
Figure 29B:
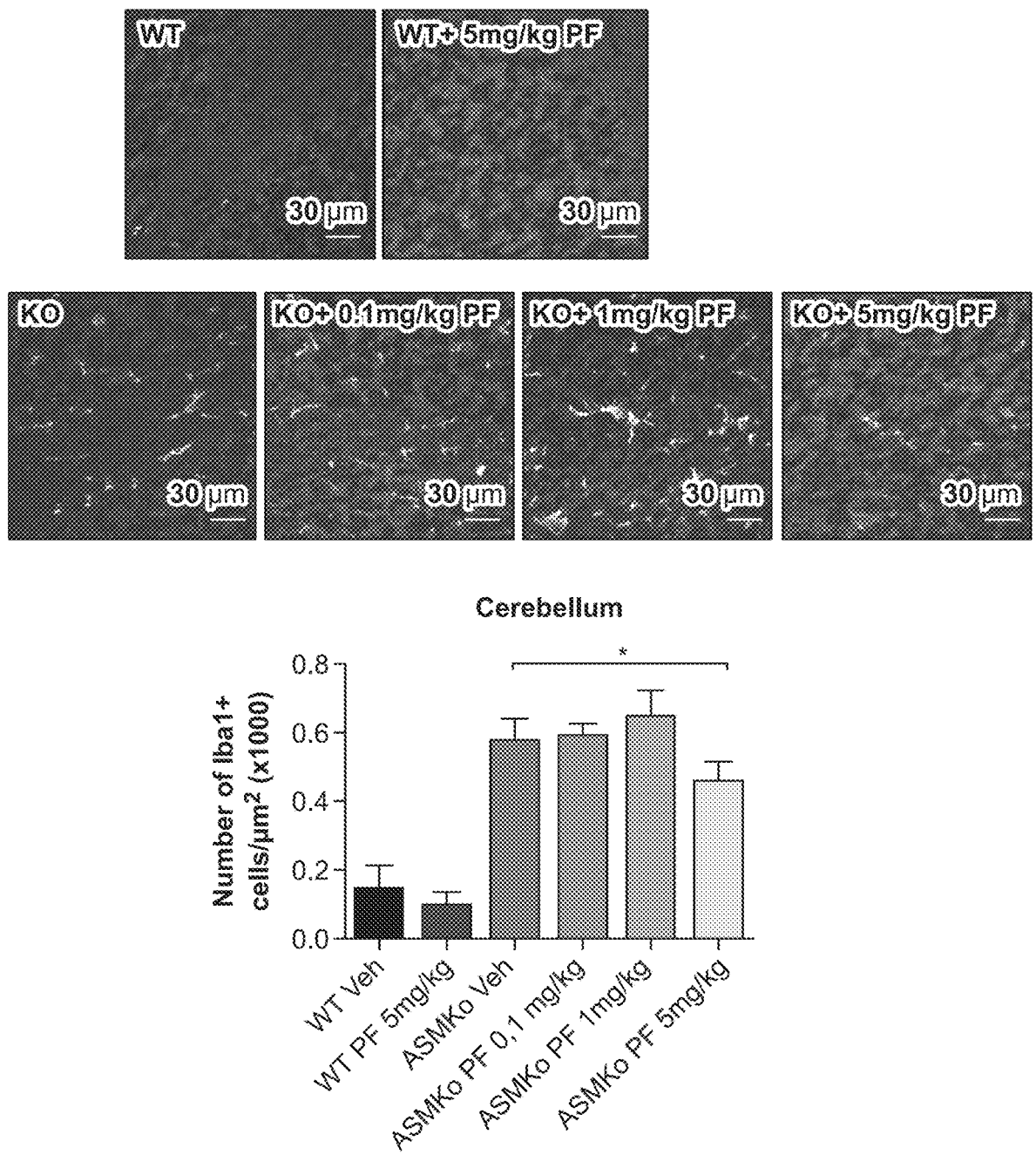
Figure 29C:
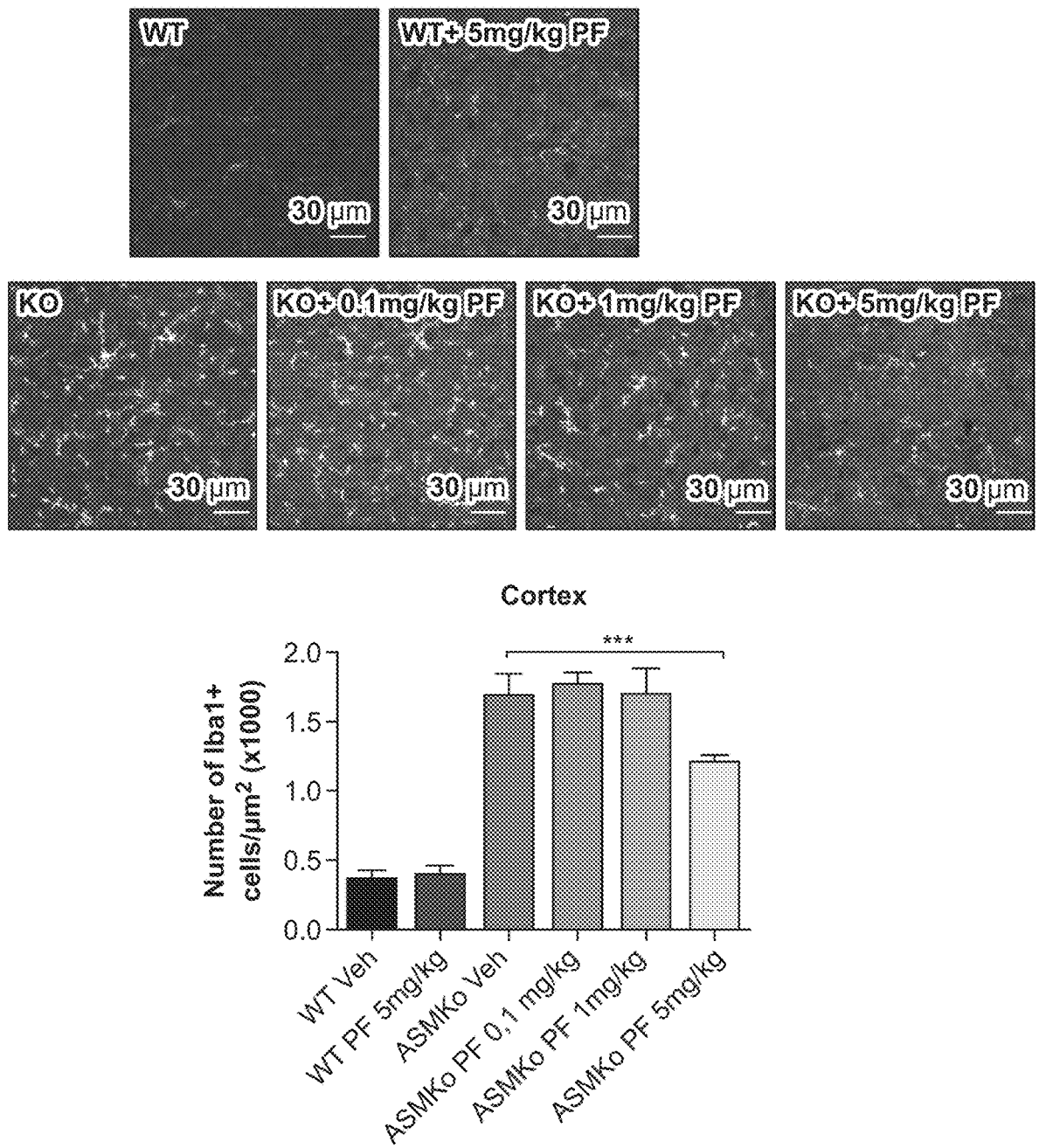

Inflammation was analyzed in different brain areas (hippocampus, cerebellum and cortex) by immunofluorescence against the microglia marker iba-1. Under inflammatory conditions the number of microglia increases. Confirming high inflammation in the brain of vehicle-treated ASMko mice, microglia numbers increased compared to wt mice in all areas (FIGS. 29A-29C). PF-04457845 treatment at 0.1 mg/kg did not significantly alter microglia numbers in the ASMko mice but 1 mg/kg and 5 mg/kg PF-04457845 doses remarkably reduced microglia numbers to levels similar to wt mice in all areas (FIGS. 29A-29C).

Figure 30:
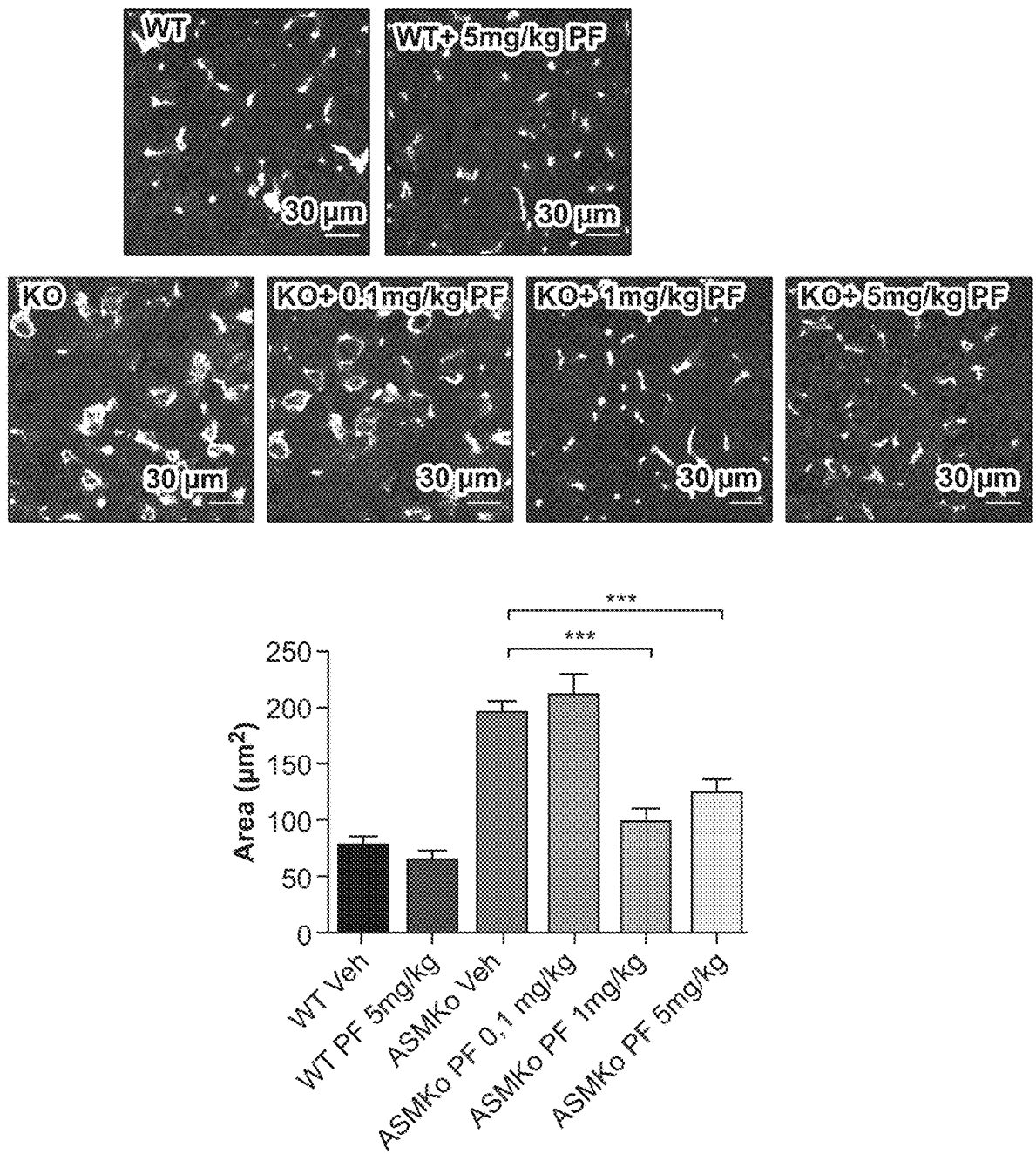
FIG. 30 shows representative images of immunofluorescence against the macrophage marker F4/80 in the liver of wt and ASMko mice treated with PF-04457845 at the indicated doses or with vehicle. Graph shows mean±SEM macrophage area (**p<0.001, Student T-test).

Inflammation was analyzed in the liver by immunofluorescence against the macrophage marker F4/80. Under inflammatory conditions macrophages acquire an amoeboid shape indicative of maximal activation. Confirming high inflammation in the liver of vehicle-treated ASMko mice, macrophages showed amoeboid morphology reflected in a drastic increase of their cell area compared to wt mice (FIG. 30). PF-04457845 treatment at 0.1 mg/kg did not significantly alter macrophage amoeboid morphology in the ASMko mice but 1 mg/kg and 5 mg/kg PF-04457845 doses remarkably reduced macrophage cell area to levels similar to wt mice (FIG. 30).

Conclusions

Administration of single doses of PF-04457845 at 0.1 mg/kg, 1 mg/kg and 5 mg/kg through oral gavage to 4.5 month-old ASMko and wt mice did not cause toxicity after 48 hours according to:
 1. Absence of significant in-life adverse effects;
 2. Absence of significant histopathological alterations in brain and liver as determined by H&E staining;
 3. Absence of further inflammation in brain and liver as determined by microglia number and macrophage morphology, respectively;

PF administration of single doses of PF-04457845 at 1 mg/kg and 5 mg/kg reduce inflammation in brain and liver of ASMko mice as evidenced by the reduced number of microglia and reduced cell area of macrophages.

PF administration induced mild sphingomyelin reduction in brain and liver tissue that was significant at the highest dose of 5 mg/kg. Sphingomyelin reduction was more pronounced in wt mice. The low levels of CB1 receptors, which mediate PF-04457845 action, in ASMko compared to wt mice may account for this difference.

Altogether these results support the safety of single doses of PF-04457845 at 0.1 mg/kg, 1 mg/kg and 5 mg/kg through oral gavage in ASMko mice even at advanced stages of the disease. In addition, doses of 1 mg/kg and 5 mg/kg PF-04457845 have positive impact in reducing inflammation and sphingomyelin levels in brain and liver.

Example 7

Preliminary Clinical Trial (n=1)

Based on the compelling safety and efficacy data from the ASMko mouse model, we submitted an expanded access request to the Food and Drug Administration for a single patient preliminary clinical trial to assess the effect of PF-04457845 administration to a single male pediatric ASMD patient. The FDA approved the trial, and it is presently ongoing. The patient received his first does of PF-04457845 (which is being administered via NG-tube delivery) nearly one year ago now, and the patient will continue to be monitored for improvement in ASMD-related symptoms and/or markers.

Although clinical trial data is not available to us yet, it is worth noting as per the normal standard of care for this patient, weekly or biweekly monitoring of liver enzymes alanine aminotransferase (ALT) and aspartate transaminase (AST) has been ongoing since before initiation of the trial and these analyses are ongoing. Elevated blood levels of AST and ALT are seen in 50%-75% of ASMD patients (McGovern M, et al., Orphanet J Rare Dis. 2017; 12: 41) and are indicative of liver damage caused by the progression of the disease. Notably, the patient's AST and ALT have both declined over the course of the last year (during which the PF-04457845 treatment has been ongoing), with the current values for each being approximately half of what they were at the onset of the monitoring, pre-treatment. Moreover, ALT/AST ratios appear stable. Thus, though preliminary, these data suggest that the treatment with PF-04457845 is being well tolerated without signs of liver toxicity and may even be resulting in an increase in liver function.

Example 8

CB1 Levels are Low in Other Lysosomal Storage Disorders

Given that many lysosomal storage diseases present with increases in SM levels, even though SM elevation is not necessarily the primary cause of these diseases, we sought to determine whether our observation regarding low CB1 expression might be a common thread tying together the mechanism of other lysosomal diseases with the mechanism of ASMD.

In addition to ASMD, SM levels are also high in NPC (as well as other lysosomal storage disorders), and ceramide (a precursor to SM) levels are elevated in MPS IIIA, suggesting SM levels may too be high, and these accumulations are accompanied by severe neurological involvement. Moreover, the etiology of these diseases is fairly well-defined, and validated mouse models are available. Thus, we analyzed CB1 expression levels in the brains of NPC (Npcnmf164) and MPS IIIA mice.

Figure 23:
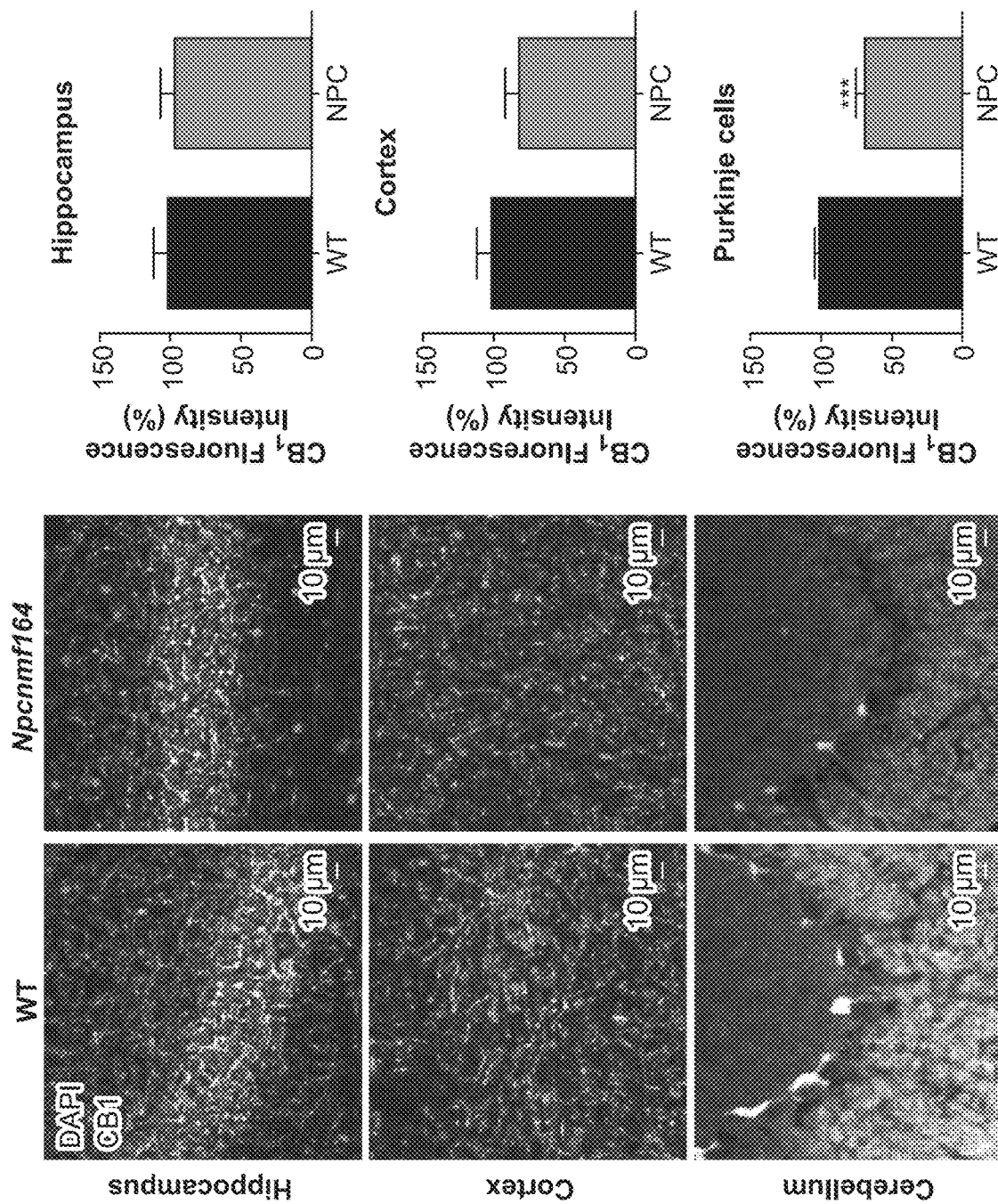
FIG. 23 shows CB1 levels are significantly reduced in Purkinje cells in the NPC mouse model (Npcnmf164) but not in hippocampus and cortex at 2.5 months of age.

CB1 levels were specifically reduced in the Purkinje cells of the cerebellum of the Npcnmf164 mice, which are mutant for NPC1 and mimic NPC (FIG. 23). CB1 was also reduced in the hippocampus and cerebellum of the mouse model for MPS IIIA (FIG. 24).

Figure 25:
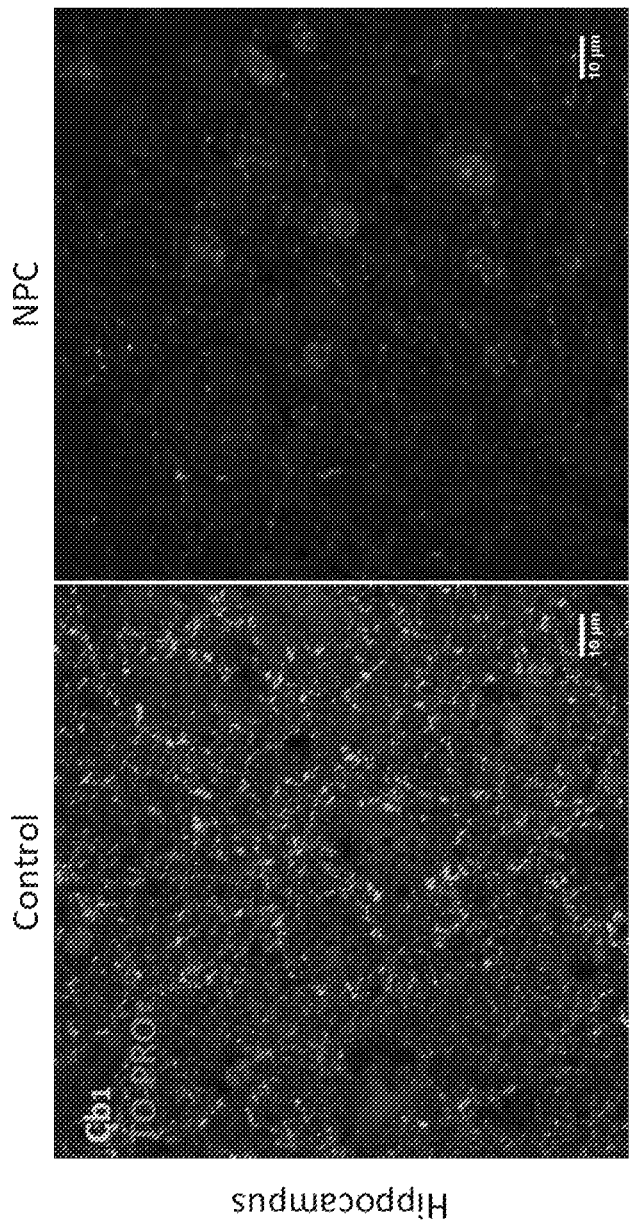
FIG. 25 shows that CB1 receptor levels are low in the hippocampus of a human NPC patient compared to a control child.

Importantly, these results are not merely artifacts of the mouse models used, as CB1 protein levels were also found diminished in the hippocampus of an NPC patient compared to an age matched non affected child (FIG. 25).

Thus, these data strongly support that lysosomal storage diseases that are caused by or that are accompanied with increases in cellular SM share a common down-regulation of the CB1 receptor. Given our results that CB1 expression is decreased in a dose dependent manner by the addition of sphingomyelin to cultured primary hippocampal neurons, we believe this mechanism will be shared by most if not all diseases that present with elevated SM levels. Moreover, we believe that all such diseases will likely be treatable to some extent by increasing or restoring native CB1 expression and or signaling, e.g., by providing exogenous cannabinoid receptor agonists such as anandamide or 2-AG or by indirectly increasing the levels of endogenous cannabinoid ligand such as anandamide or 2-AG by inhibiting their degradation (e.g., by inhibiting FAAH or Monoacylglycerol lipase, or "MAGL", the enzyme responsible for degrading 2-AG), or stimulating increases in their production (e.g., by activating the mGluR5 receptor, e.g., with CDPPB).

The various embodiments described above can be combined to provide further embodiments. All of the U.S. patents, U.S. patent application publications, U.S. patent application, foreign patents, foreign patent application and non-patent publications referred to in this specification and/ or listed in the Application Data Sheet are incorporated herein by reference, in their entirety. Aspects of the embodiments can be modified, if necessary to employ concepts of the various patents, application and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of treating a lysosomal storage disease or disorder in a subject, comprising: administering a fatty acid amide hydrolase (FAAHi) inhibitor to the subject, wherein the lysosomal storage disease or disorder is characterized by an abnormal accumulation of sphingomyelin in the subject's cells.

2. The method of claim 1, wherein the lysosomal storage disease is selected from Acid Sphingomyelinase Deficiency (ASND), Type A Niemann Pick disease (NPA), Type B Niemann Pick disease (NPB), Type AB Niemann Pick disease (NPA/B), Type C Niemann Pick disease (NPC), mucopolysaccharidosis type IIIA (MPS IIIA), Farber disease, Gaucher disease, Pompe disease, Fabry disease, and Sanfilippo disease.

3. The method of claim 1, wherein the FAAHi results in the activation of neutral sphingomyelinase.

4. The method of claim 1, wherein the FAAHi inhibitor results in activation of the CB1 cannabinoid receptor or increase of one or more cannabinoid levels in the subject.

5. The method of claim 4, wherein the one or more cannabinoid levels are increased by stimulating production of the cannabinoid, inhibiting degradation of the cannabinoid, or both.

6. The method of claim 1, wherein the FAAHi is administered to the subject as a pharmaceutical composition comprising the FAAHi and one or more pharmaceutically acceptable salts, excipients or vehicles.

7. The method of claim 1, wherein the method treats a loss of motor skills, cognitive decline, and/or systemic organ pathology in the subject.

8. The method of claim 1, wherein the method reduces inflammation or sphingomyelin levels in the subject.

9. The method of claim 8, wherein the method improves the subject's cognition, learning and/or memory.

10. The method of claim 8, wherein the method reduces a sphingomyelin level in an organ selected from the brain, liver, spleen, lung, heart, adrenal gland, articular cartilage, articular joint space, and bone marrow.

11. The method of claim 1, wherein the lifespan of the subject is increased as compared to the expected lifespan of an individual with the same lysosomal storage disease that has not been administered a FAAHi.

12. The method of claim 1, wherein the method further comprises administering one or more additional therapeutic agents to the subject, wherein the one or more additional therapeutic agents are selected from the group consisting of a recombinant acid sphingomyelinase (ASM), an autologous cell expressing a gene encoding a functional ASM enzyme, a recombinant virus expressing a gene encoding a functional ASM enzyme, a glucocorticoid, an HSP70 inhibitor, an inhibitor of histone deacetylase, an inhibitor of ganglioside production, an inhibitor of ceramide production, anandamide, 2-AG, CDPPB, and any combination thereof.

* * * * *

UNITED STATES PATENT AND TRADEMARK OFFICE
CERTIFICATE OF CORRECTION

PATENT NO. : 12,023,332 B2
APPLICATION NO. : 16/977772
DATED : July 2, 2024
INVENTOR(S) : Maria Dolores Ledesma et al.

It is certified that error appears in the above-identified patent and that said Letters Patent is hereby corrected as shown below:

In the Claims

At Column 36, Claim number 2, Line number 57, it is shown as "(ASND)". It needs to be --(ASMD)--.

At Column 36, Claim number 2, Line number 58, it is shown as "Type AB". It needs to be --Type A/B--.

Signed and Sealed this
Thirteenth Day of August, 2024

Katherine Kelly Vidal
*Director of the United States Patent and Trademark Office*